United States Patent
Chekmenev et al.

(10) Patent No.: US 11,016,152 B2
(45) Date of Patent: May 25, 2021

(54) METHOD FOR CREATING HYPERPOLARIZATION AT MICROTESLA MAGNETIC FIELDS

(71) Applicants: Vanderbilt University, Nashville, TN (US); Duke University, Durham, NC (US); The Board of Trustees of Southern Illinois University, Carbondale, IL (US)

(72) Inventors: Eduard Y. Chekmenev, Brentwood, TN (US); Danila A. Barskiy, Nashville, TN (US); Roman V. Shchepin, Nashville, TN (US); Warren S. Warren, Durham, NC (US); Thomas Theis, Durham, NC (US); Boyd Goodson, Carbondale, IL (US)

(73) Assignees: Vanderbilt University, Nashville, TN (US); Duke University, Durham, NC (US); The Board of Trustees of Southern Illinois University, Carbondale, IL (US)

( * ) Notice: Subject to any disclaimer, the term of this patent is extended or adjusted under 35 U.S.C. 154(b) by 2 days.

(21) Appl. No.: 16/607,701

(22) PCT Filed: May 12, 2018

(86) PCT No.: PCT/US2018/032485
§ 371 (c)(1),
(2) Date: Oct. 23, 2019

(87) PCT Pub. No.: WO2018/209334
PCT Pub. Date: Nov. 15, 2018

(65) Prior Publication Data
US 2020/0132788 A1 Apr. 30, 2020

Related U.S. Application Data

(60) Provisional application No. 62/505,721, filed on May 12, 2017.

(51) Int. Cl.
*G01R 33/28* (2006.01)
*G01R 33/44* (2006.01)

(52) U.S. Cl.
CPC ........ *G01R 33/282* (2013.01); *G01R 33/445* (2013.01)

(58) Field of Classification Search
USPC ....................................................... 324/309
See application file for complete search history.

(56) References Cited

U.S. PATENT DOCUMENTS 6,426,058 B1 7/2002 Pines et al.
2010/0092391 A1* 4/2010 Ross ................ G01R 33/5601
424/9.3

(Continued)

OTHER PUBLICATIONS

Albers et al., "Hyperpolarized 13C Lactate, Pyruvate, and Alanine: Noninvasive Biomarkers for Prostate Cancer Detection and Grading", Cancer Research, 68 (20), pp. 8607-8615, Oct. 2008.

(Continued)

*Primary Examiner* — Rodney E Fuller
(74) *Attorney, Agent, or Firm* — Michael Best & Friedrich LLP

(57) ABSTRACT

Provided are methods for nuclear spin polarization enhancement via signal amplification by reversible exchange at very low magnetic fields. The spin polarization is hyperpolarization of isotopically enriched heteronuclei by using a catalyst and parahydrogen to create a complex using iridium and applying magnetic fields in the microtesia range to transfer the spin order from parahydrogen to the complex.

19 Claims, 54 Drawing Sheets

(56) References Cited

U.S. PATENT DOCUMENTS

| | | |
|---|---|---|
| 2010/0219826 A1 | 9/2010 | Duckett et al. |
| 2016/0045907 A1 | 2/2016 | Chekmenev et al. |
| 2016/0169998 A1 | 6/2016 | Warren et al. |

OTHER PUBLICATIONS

Ardenkjaer-Larsen et al., "Dynamic Nuclear Polarization Polarizer for Sterile Use Intent", NMR in Biomedicine, 2011, 24, pp. 927-932.

Ardenkjaer-Larsen et al., "Facing and Overcoming Sensitivity Challenges in Biomolecular NMR Spectroscopy", Angew. Chem. Int. Ed. 2015, 54 (32), pp. 9162-9185.

Ardenkjaer-Larsen, "On the present and future of dissolution—DNP", Journal of Magnetic Resonance, 264, 2016, pp. 3-12.

Barskiy et al., "A simple analytical model for signal amplication by reversible exchange (SABRE) process", Phys. Chem. Chem. Phys. 2016, 18, pp. 89-93.

Barskiy et al., "NMR Hyperpolarization Techniques of Gases", Chemistry A European Journal Minireview, 2017, 23, pp. 725-751.

Barskiy et al., "Over 20%15N Hyperpolarization in Under One Minute for Metronidazole, an Antibiotic and Hypoxia Probe", Journal of the American Chemicla Society, 2016, 138 (26), pp. 8080-8083.

Bernatowicz et al., "Scalar Relaxtion of the Second Kind. A Potential Source of Information on the Dynamics of Molecular Movements. 4. Molecules with Collinear C—H and C—Br Bonds", the Journal of Physical Chemistry A, 2014, 118, pp. 4063-4070.

Bhattacharya et al., "Parahydrogen-induced polarization (PHIP) hyperpolarized MR receptor imaging in vivo: a pilot study of 13C imaging of atheroma in mice", NMR in Biomediceine, 2011, 24, pp. 1023-1028.

Bhattacharya et al., "Towards Hyperpolarized 13C-succinate imaging of brain cancer", Journal of Magnetic Resonance, 2007, 186, pp. 150-155.

Blum et al., "Ab initio molecular simulations with numeric atom-centered orbitals", Computer Physics Communications, 2009, 180 (11), pp. 2175-2196.

Bornet et al., "Boosting Dissolution Dynamic Nuclear Polarization by Cross Polarization", The Journal of Physical Chemistry Letters, 2013, 4, pp. 111-114.

Brindle, "Imaging Metabolism with Hyperpolarized 13C-Labeled Cell Substrates", Journal of the American Chemical Society, 2015, 137 (20), pp. 6418-6427.

Cai et al., "Efficient Transformation of Parahydrogen Spin Order into Heteronuclear Magnetization", The Journal of Physical Chemistry B, 2013, 117, pp. 1219-1224.

Carravetta et al., "Beyond the T1 limit: Singlet nuclear spin states in low magnetic fields", Physical Review Letters, 2004, vol. 92, No. 15, 153003-1-153003-4.

Carravetta et al., "Long-lived nuclear spin states in high-field solution NMR", J. Am. Chem. Soc. 2004, 126 (20), pp. 6228-6229.

Coffey et al., "Open-Source Automated Parahydrogen Hyperpolarizer for Molecular Imaging Using 13C Metabolic Contrast Agents", Analytical Chemistry, 2016, 88, pp. 8279-8288.

Colell et al., "Generalizing, Extending, and Maximizing Nitrogen-15 Hyperpolarization Induced by Parahydrogen in Reversible Exchange", The Journal of Physical Chemistry C, 2017, 121 (12), pp. 6626-6634.

Comment et al., "Hyperpolarized Magnetic Resonance as a Sensitive Detector of Metabolic Function", Biochemistry, 2014, 53, pp. 7333-7357.

Deng et al., "Calculation of Nuclear Spin-Spin Coupling Constants of Molecules with First and Second Row Atoms in Study of Basis Set Dependence", Journal of Chemical Theory and Computation, 2006, 2 (4), pp. 1028-1037.

DeVience et al., "In Spin-locking induced crossing: J-coupling spectroscopy at high and low fields", Poster at Experimental Nmr Conference, Pacific Grove, CA, 2013.

Dunning, "Gaussian basis sets for use in correlated molecular calculations I. The atoms boron through neon and hydrogen", J. Chem. Phys., 1989, 90 (2), pp. 1007-1023.

Eshuis et al., "Toward Nanomolar Detection by NMR Through SABRE Hyperpolarization", Journal of American Chemical Society, 2014, 136 (7), pp. 2695-2698.

Feng et al., "Storage of hydrogen spin polarization in long-lived 13C2 singlet order and implications for hyperpolarized magnetic resonance imaging", Journal of the American Chemical Society, 2013, 135 (26), pp. 9632-9635.

Goldman et al., "Conversion of a proton pair para order into 13C polarization by rf irradiation, for use in MRI", C.R. Physique 2005, 6, pp. 575-581.

Golman et al., "Parahydrogen-Induced Polarization in Imaging: Subsecond 13C Angiography", Magnetic Resonance in Medicine, 2001, 46, pp. 1-5.

Golman et al., "Real-time metabolic imaging", Proc. Natl. Acad. Science, vol. 103, No. 30, Jul. 2006, pp. 11270-11275.

Goodson, "Advances in Magnetic Resonance: Nuclear Magnetic Resonance of Laser-Polarized Noble Gases in Molecules, Materials, and Organisms", Journal of Magnetic Resonance, 2002, 155, pp. 157-216.

Green et al., "The theory and practice of hyperpolarization in magnetic resonance using parahydrogen", Progress in Nuclear Magnetic Resonance Spectroscopy, 2012, 67, pp. 1-48.

Hirsch et al., "Brute-Force Hyperpolarization for NMR and MRI", Journal of the American Chemical Society, 2015, 137, pp. 8428-8434.

Hövener et al., "Biocompatible Nuclear Hyperpolarization Using Signal Amplification by Reversible Exchange: Quantitative in Situ Spectroscopy and High-Field Imaging", Analytical Chemistry, 2014, 86 (3), pp. 1767-1774.

Jensen et al., "The Elephant in the Room of Density Functional Theory Calculations", The Journal of Physical Chemistry Letters, 2017, 8 (7), pp. 1449-1457.

Keshari et al., "Chemistry and biochemistry of 13C hyperpolarized magnetic resonance using dynamic nuclear polarization", Chem. Soc. Rev. 2014, 43 (5), pp. 1627-1659.

Kovtunov et al., "Parahydrogen-Induced Polarization in Heterogeneous Catalytic Processes", Top. Curr. Chem. 2013, 338, pp. 123-180.

Levitt et al., "Singlet Nuclear Magnetic Resonance", Ann. Rev. Phys. Chem. 2012, 63, pp. 89-105.

Lisitza et al., "Toward 13C Hyperpolarized biomarkers produced by thermal mixing with hyperpolarized 129Xe", The Journal of Chemical Physics, vol. 131, 2009, pp. 044508-1-044508-5.

Liu et al., "One-thousand-fold enhancement of high field liquid nuclear magnetic resonance signals at room temperature", Nature Chemistry, 2017, vol. 9, 2017, pp. 676-680.

Logan et al., "Hyperpolarization of Nitrogen-15 Schiff Bases by Reversible Exchange Catalysis with para-Hydrogen", Chem. Eur. J. 2016, 22 (31), pp. 10777-10781.

Mewis et al., "Strategies for the Hyperpolarization of Acetonitrile and Related Ligands by Sabre", the Journal of Physical Chemistry B, 2015, 119(4), pp. 1416-1424.

Nikolaou et al., "Near-unity nuclear polarization with an open-source 129Xe hyperpolarizer for NMR and MRI", Proc. Natl. Acad. Sci., 2013, 110, pp. 14150-14155.

Nonaka et al., "Design of a 15N Molecular Unit to Achieve Long Retention of Hyperpolarized Spin State", Science Reports, 2017, 7, 6 pages.

Olaru et al., "Creating a hyperpolarised pseudo singlet state through polarisation transfer from parahydrogen under SABRE", Chem. Commun. 2016, 52 (50), pp. 7842-7845.

Perdew et al., "Generalized Gradient Approximation Made Simple", Physical Review Letters, vol. 77, No. 18, Oct. 1996, pp. 3865-3868.

Pravdivtsev et al., "Enhancing NMR of insensitive nuclei by transfer of SABRE spin hyperpolarization", Chemical Physics Letters, 661, 2016, pp. 77-82.

Pravdivtsev et al., "Transfer of SABRE-derived hyperpolarization to spin-½ heteronuclei", RSC Advances, vol. 5., 2015, pp. 63615-63623.

(56) References Cited

OTHER PUBLICATIONS

Rayner et al., "Delivering strong 1H nuclear hyperpolarization levels and long magnetic lifetimes through signal amplification by reversible exchange", Proc. Natl. Acad. Sci., 2017, 114 (16), pp. E3188-E3194.
Rovedo et al., "Molecular MRI in the Earth's Magnetic Field Using Continuous Hyperpolarization of a Biomolecule in Water", The Journal of Physical Chemistry B, 120 (25), 2016, pp. 5670-5677.
Roy et al., "A Hyperpolarizable 1H Magnetic Resonance Probe for Signal Detection 15 Minutes after Spin Polarization Storage", Angew. Chem. Int. Ed., 128 (50), 2016, pp. 15871-15874.
Roy et al., "Long-lived states to sustain Sabre hyperpolarised magnetisation", Phys. Chem. Chem. Phys., 18 (36), 2016, pp. 24905-24911.
Shchepin et al., "15N Hyperpolarization of Imidazole-15N2 for Magnetic Resonance pH Sensing via SABRE SHEATH", ACS Sensors, vol. 1, 2016, pp. 640-644.
Shchepin et al., "Efficient Synthesis of Nicotinamide-1-15N for Ultrafast NMR Hyperpolarization Using Parahydrogen", Bioconjugate Chemistry, 2016, 27 (4), pp. 878-882.
Shi et al., "Aqueous NMR Signal Enhancement by Reversible Exchange in a Single Step Using Water-Soluble Catalysts", The Journal of Physical Chemistry C, 2016, 120 (22), pp. 12149-12156.
Spannring et al., "A New Ir-NHC Catalyst for Signal Amplification by Reversible Exchange in D2O", Chem. Eur. J. 2016, 22 (27), pp. 9277-9282.
Stevanato et al., "A Nuclear Singlet Lifetime of More than One Hour in Room-Temperature Solution", Angew. Chem. Int. Ed. 2015, 54 (12), pp. 3740-3743.
Tayler et al., "Singlet nuclear magnetic resonance of nearly-equivalent spins", Phys. Chem. Chem. Phys., 2011, 13, pp. 5556-5560.
Tee et al., "Sampling Hyperpolarized Molecules Utilizing a 1 Tesla Permanent Magnetic Field", Scientific Reports, 2016, 6, 6 pages.
Theis et al., "Composite and shaped pulses for efficient and robust pumping of disconnected eigenstates in magnetic resonance", The Journal of Chemical Physics, vol. 140, 2014, p. 014201-1.
Theis et al., "Direct and cost-efficient hyperpolarization of long-lived nuclear spin states on universal 15N2-diazirine molecular tags", Sci. Adv., 2016, 2 (3), e1501438.
Theis et al., "LIGHT-SABRE enables efficient in-magnet catalytic hyperpolarization", Journal of Magnetic Resonnance, 2014, 248, pp. 23-26.
Theis et al., "Microtesla SABRE Enables 10% Nitrogen-15 Nuclear Spin Polarization", Journal of the American Chemical Society, 2015, 137 (4), pp. 1404-1407.
Tkatchenko et al., "Accurate Molecular Van Der Waals Interactions from Ground-State Electron Density and Free-Atom Reference Data", Physical Review Letters, 2009, 102 (7), pp. 073005-1-073005-4.
Vasos et al., "Long-lived states to sustain hyperpolarized magnetization", Proc. Natl. Acad. Sci., vol. 106, No. 44, 2009, pp. 18469-18473.
Walker et al., "Spin-exchange optical pumping of noble-gas nuclei", Reviews of Modern Physics, vol. 69, No. 2, pp. 629-642.
Warren et al., "Increasing Hyperpolarized Spin Lifetimes Through True Singlet Eigenstates", Science, vol. 323, Mar. 2009, pp. 1711-1714.
Zacharias et al., "Real-Time Molecular Imaging of Tricarboxylic Acid Cycle Metabolism in Vivo by Hyperpolarized 1-13C Diethyl Succinate", Journal of the American Chemical Society, vol. 134, 2012, pp. 934-943.
Zeng et al., "Achieving 1% NMR polarization in water in less than 1 min using SABRE", Journal of Magnetic Resonance, vol. 246, 2014, pp. 119-121.
Zheng et al., "A method for imaging and spectroscopy using γ-rays and magnetic resonance", Nature, vol. 537, 2016, pp. 652-655.
International Search Report and Written Opinion for Application No. PCT/US18/32485 dated Aug. 1, 2018 (9 pages).
Adams et al., "Reversible interactions with para-hydrogen enhance NMR sensitivity by polarization transfer", Science 2009, 323 (5922), 1708-11.
Ardenkjr-Larsen et al., "Increase in signal-to-noise ratio of >10,000 times in liquid-state" Nmr. Proc. Natl. Acad. Sci. USA 2003, 100 (18), 10158-10163.
Barskiy et al., "The Feasibility of Formation and Kinetics of NMR Signal Amplification by Reversible Exchange (SABRE) at High Magnetic Field (9.4 T)", Journal of American Chemical Society, vol. 136, 2014, pp. 3322-3325.
Bowers et al., "Transformation of Symmetrization Order to Nuclear-Spin Magnetization by Chemical-Reaction and Nuclear-Magnetic-Resonance", Phys. Rev. Lett. 1986, 57 (21), 2645-2648.
Cowley et al., "Iridium N-Heterocyclic Carbene Complexes as Efficient Catalysts for Magnetization Transfer from para-Hydrogen", J. Am. Chem. Soc. 2011, 133 (16), 6134-6137.
Day et al., "Detecting Tumor Response to Treatment Using Hyperpolarized C-13 Magnetic Resonance Imaging and Spectroscop," Nat. Med. (2007) 13, 1382-1387.
Eisenschmid et al., Para Hydrogen Induced Polarization in Hydrogenation Reactions, J. Am. Chem. Soc. 1987, 109 (26), 8089-8091.
Kurhanewicz et al., "Analysis of cancer metabolism by imaging hyperpolarized nuclei: prospects for translation to clinical research", Neoplasia 2011, 13 (2), 81-97.
Nelson et al., "Metabolic imaging of patients with prostate cancer using hyperpolarized [1-(1)(3)C]pyruvate", Sci. Trans!. Med. 2013, 5 (198), 198ra108.
Nikolaou et al., "NMR Hyperpolarization Techniques for Biomedicine", Chem. Eur. J. 2015, 21 (8), 3156-3166.
Shchepin et al., "Hyperpolarization of "Neat" Liquids by NMR Signal Amplification by Reversible Exchange", J. Chem. Phys. Lett. 2015, 6 (10), 1961-1967.
Shi et al., "Heterogeneous Solution NMR Signal Amplification by Reversible Exchange", Angew. Chem. Int. Ed. 2014, 53 (29), 7495-7498.
Shi et al., "Nanoscale Catalysts for NMR Signal Enhancement by Reversible Exchange", J. Phys. Chem. C 2015, 119 (13), 7525-7533.
Truong et al., "15N Hyperpolarization by Reversible Exchange Using SABRE-SHEATH", J. Phys. Chem. C 2015, 119 (16), 8786-8797.
Truong et al., "Irreversible Catalyst Activation Enables Hyperpolarization and Water Solubility for NMR Signal Amplification by Reversible Exchange", J. Phys. Chem. B 2014, 118 (48), 13882-13889.
Vazquez-Serrano et al., "The search for new hydrogenation catalyst motifs based on N-heterocyclic carbene ligands", Inorg. Chim. Acta 2006, 359 (9), 2786-2797.
Zhivonitko et al., "Strong 31P nuclear spin hyperpolarization produced via reversible chemical interaction with parahydrogen" Chem. Commun. 2015, 51 (13), 2506-2509.

\* cited by examiner

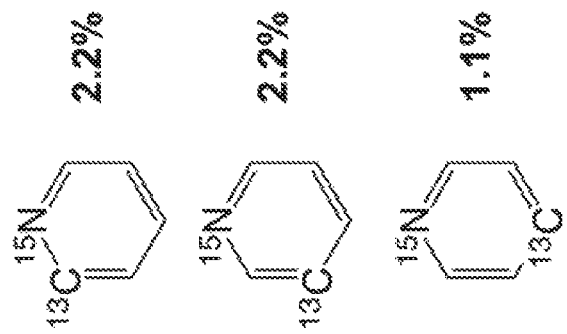
FIG. 1B
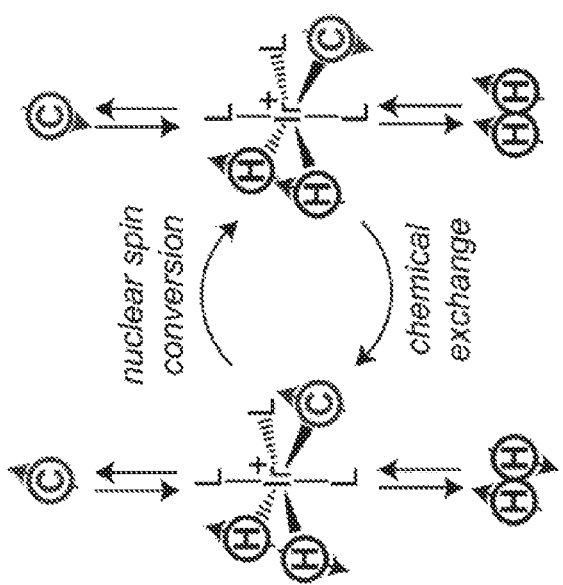
FIG. 1A
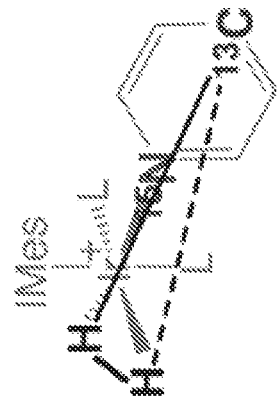
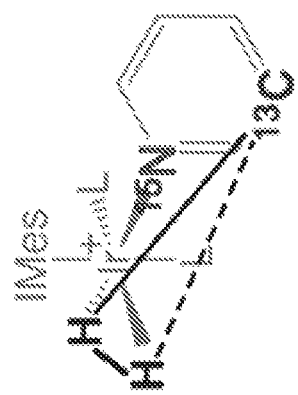
FIG. 1C
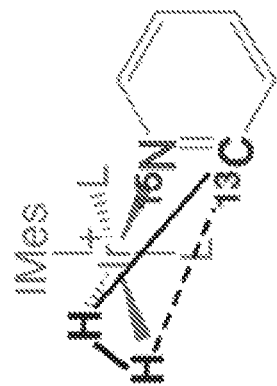

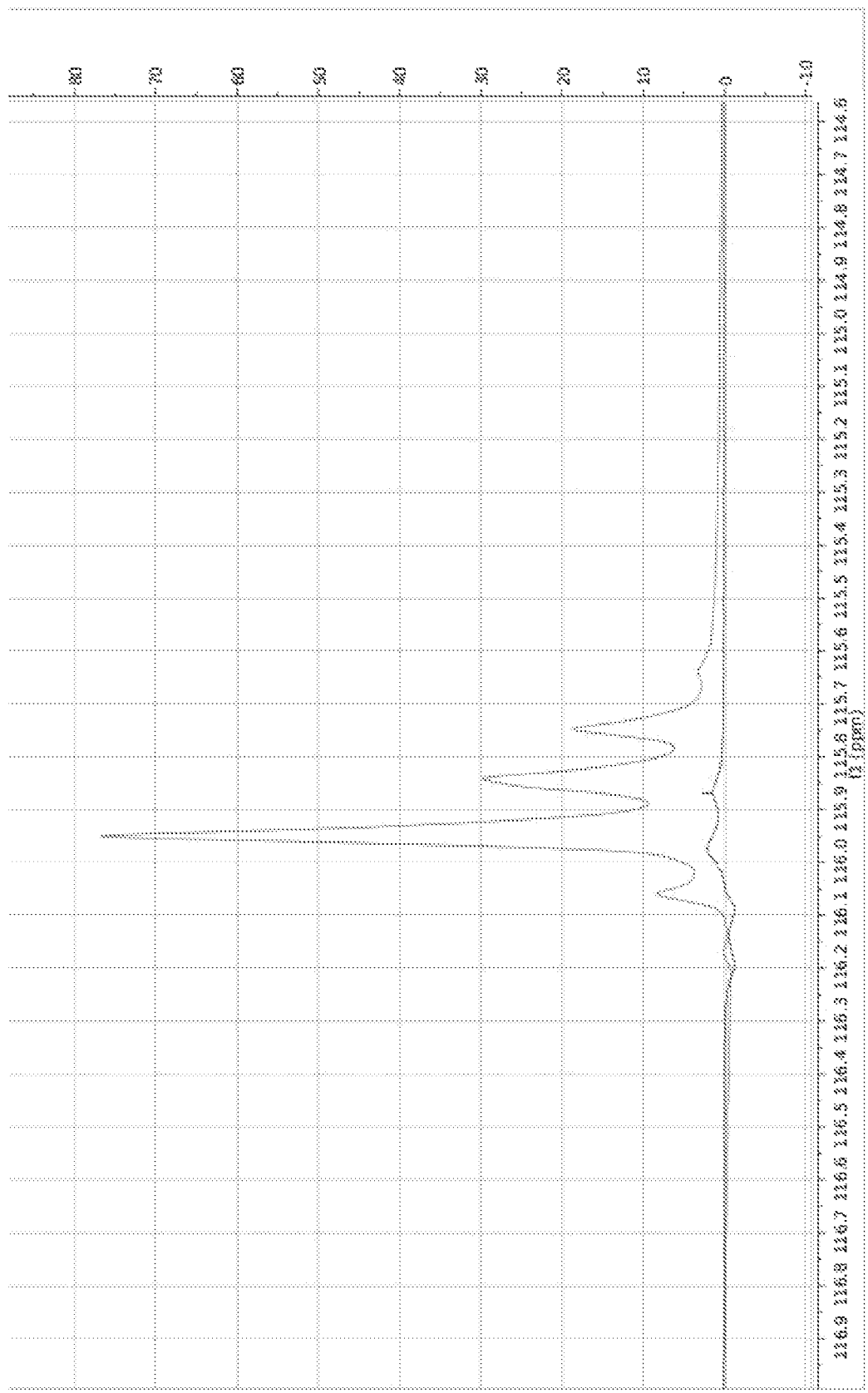

direct (from hydrides) transfer relayed (via $^{15}N$) transfer

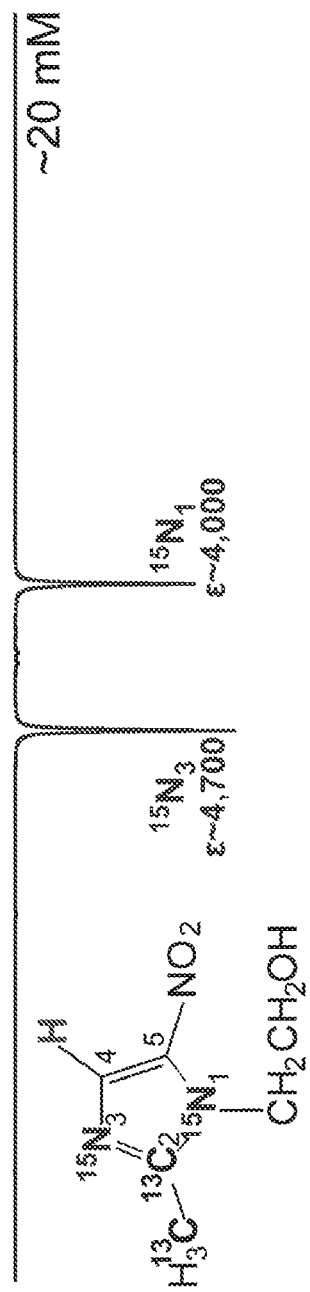
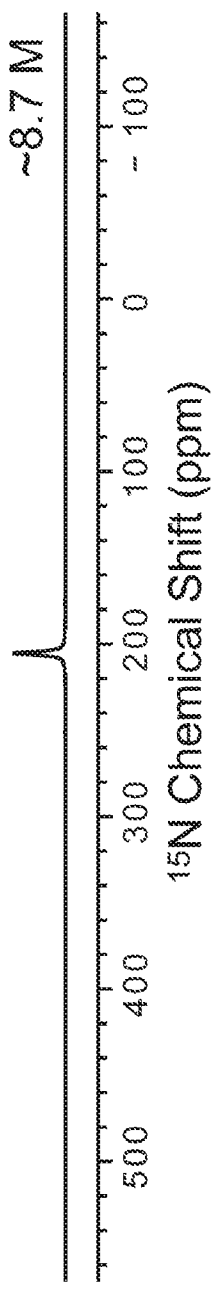
FIG. 16A
FIG. 16B

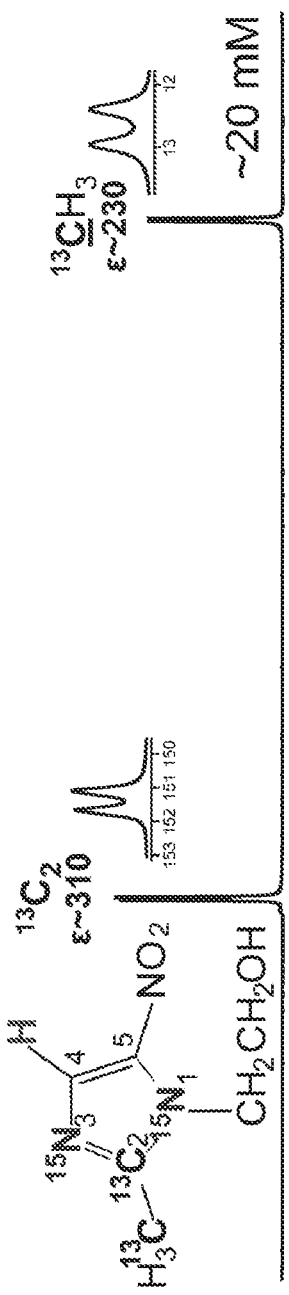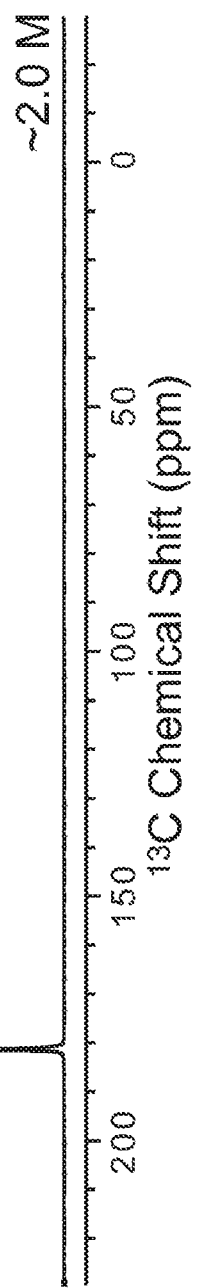
FIG. 16C
FIG. 16D

FIG. 18A
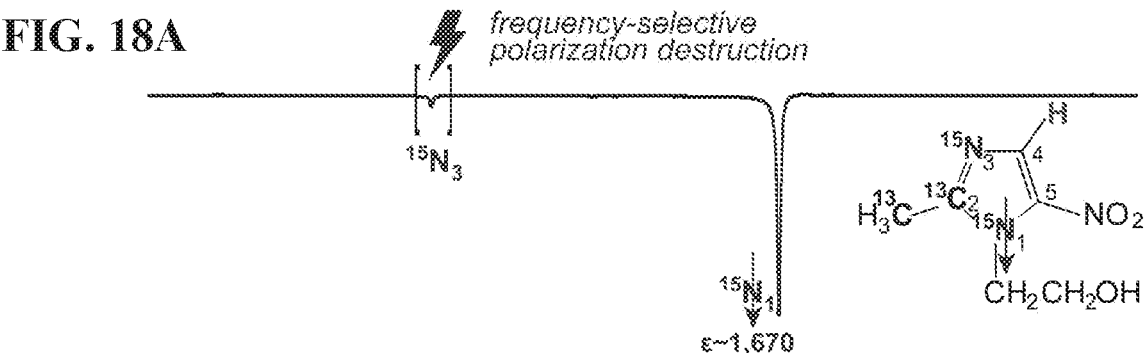
FIG. 18B
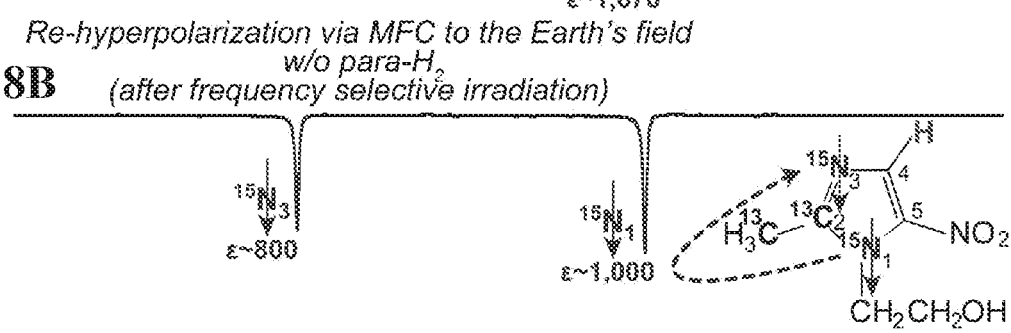
FIG. 18C *Hyperpolarization at the Earth's field with para-H₂ (control)*
FIG. 18D
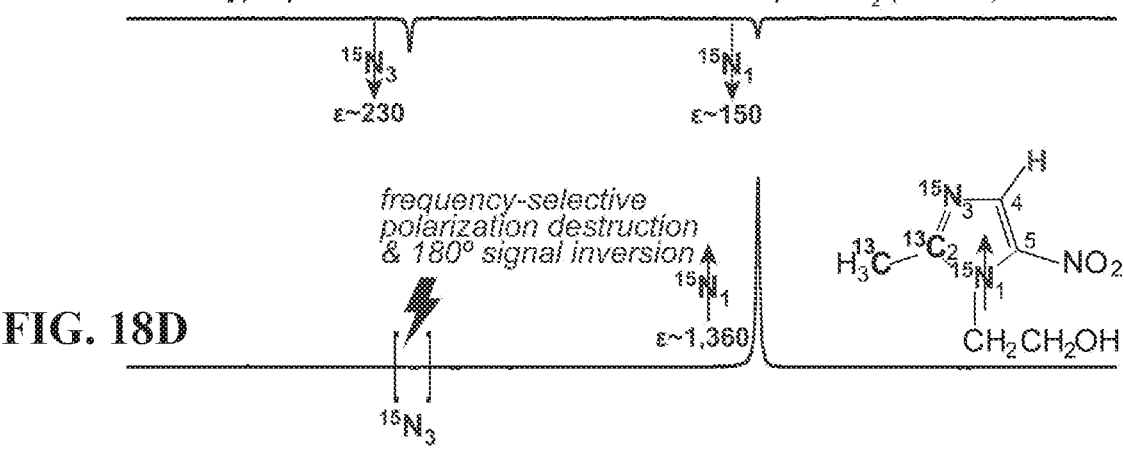
FIG. 18E
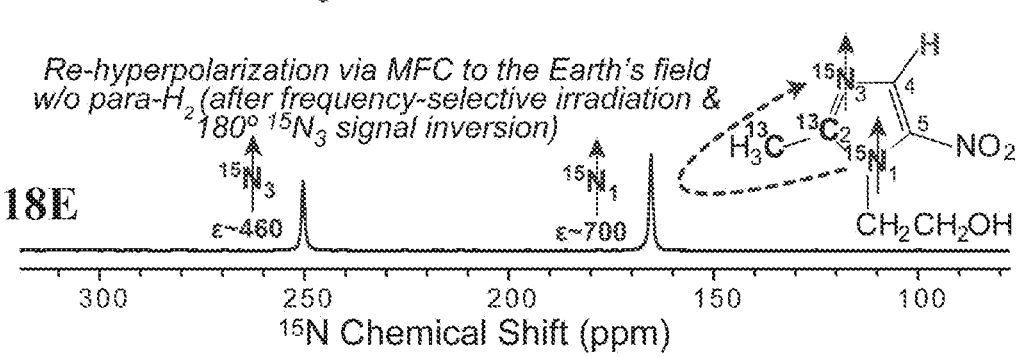
FIG. 18

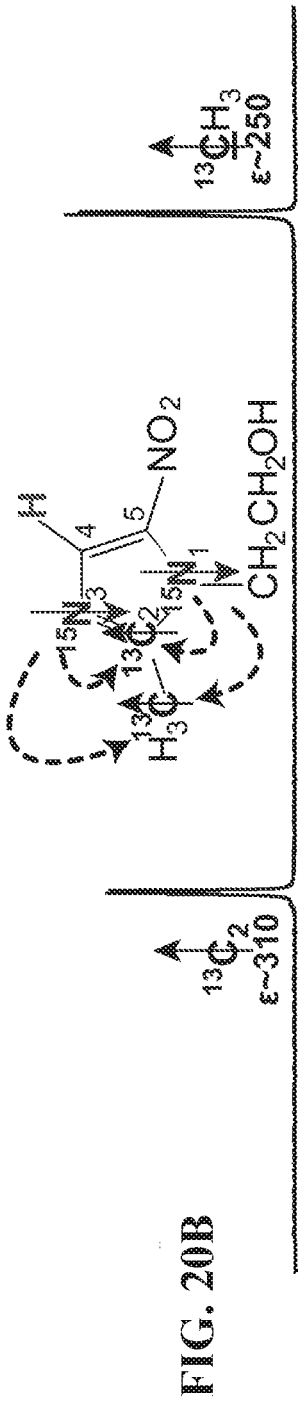
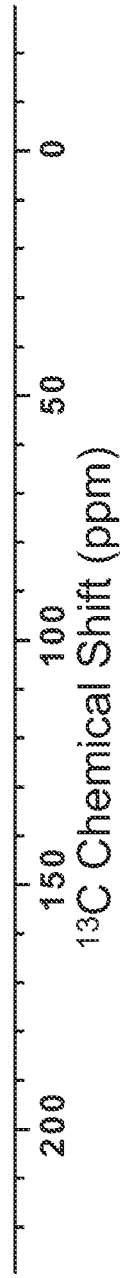
FIG. 20A
FIG. 20B
FIG. 20C
FIG. 20

FIG. 22A
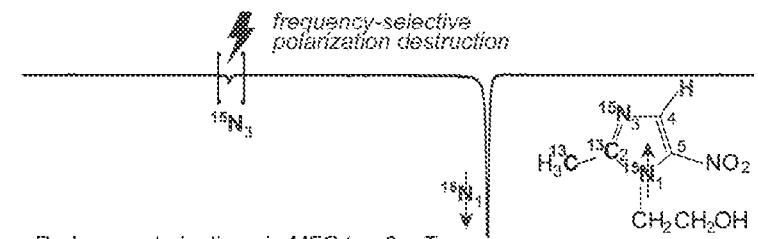
FIG. 22B
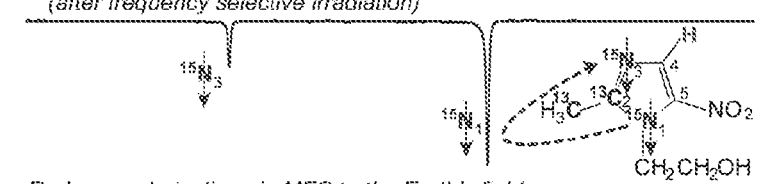
FIG. 22C
FIG. 22D
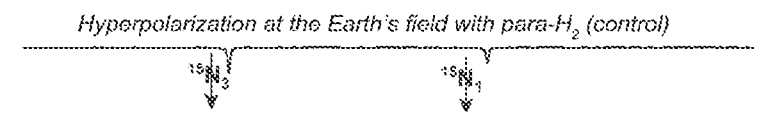
FIG. 22E
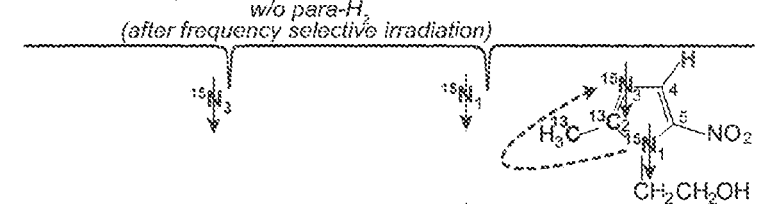
FIG. 22F
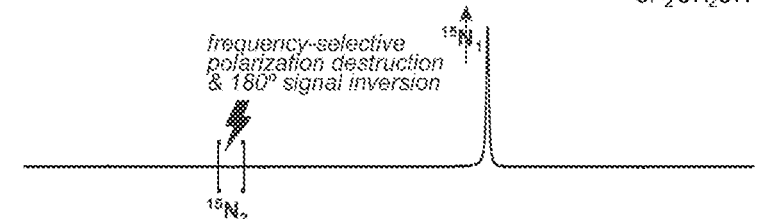
FIG. 22G
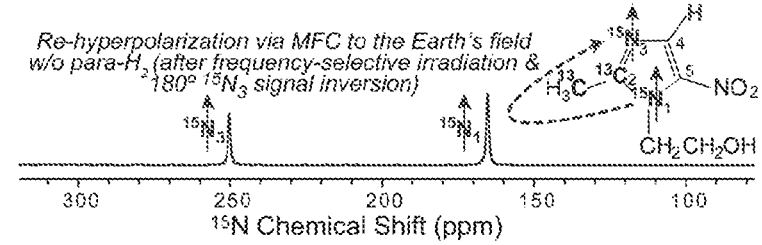
FIG. 22

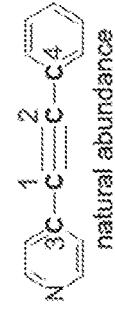
FIG. 23A  FIG. 23B  FIG. 23C  FIG. 23D
FIG. 23

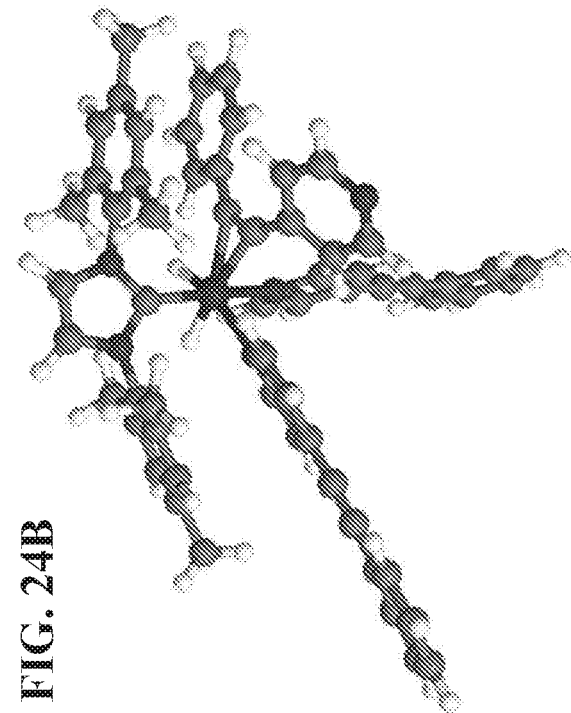
FIG. 24A
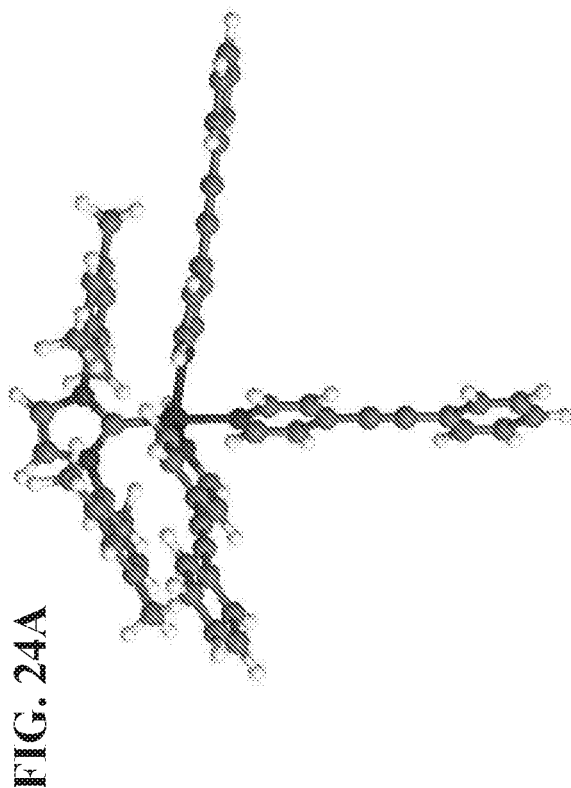
FIG. 24B
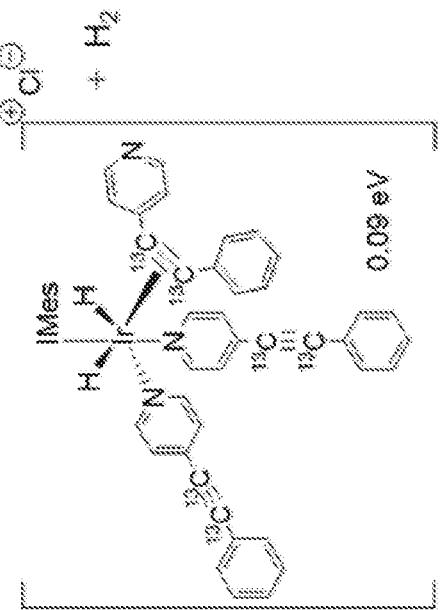
FIG. 24
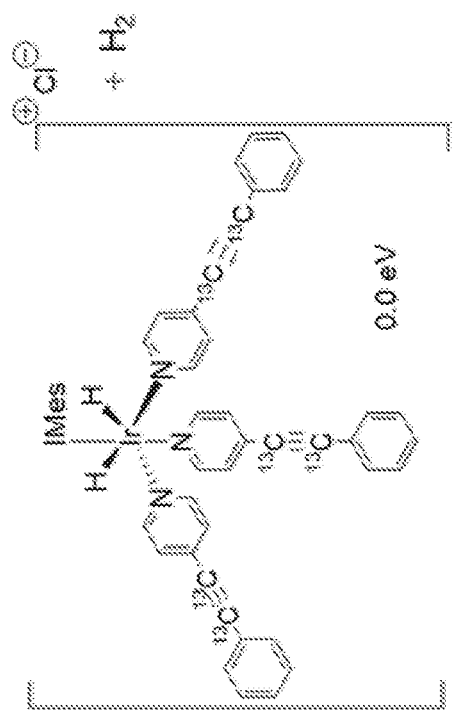

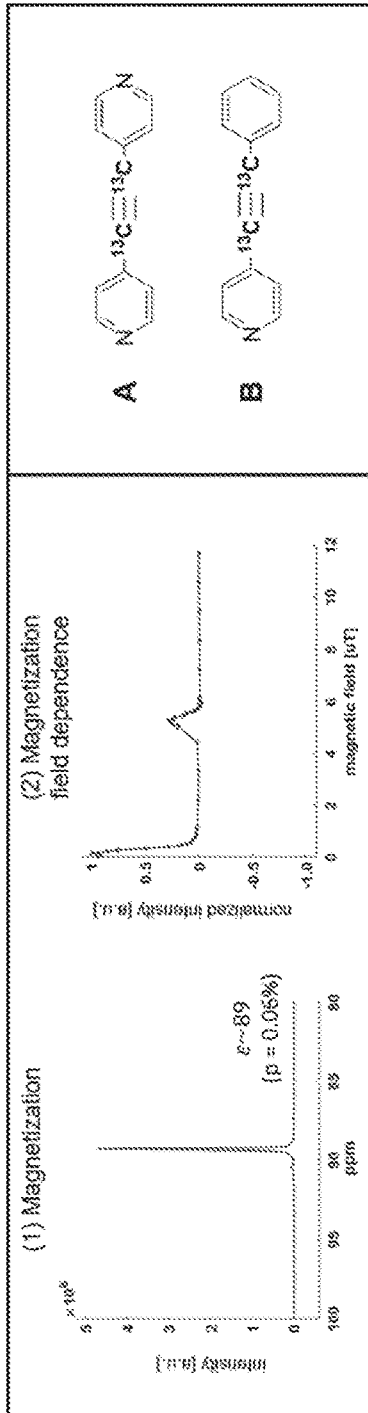
FIG. 25A
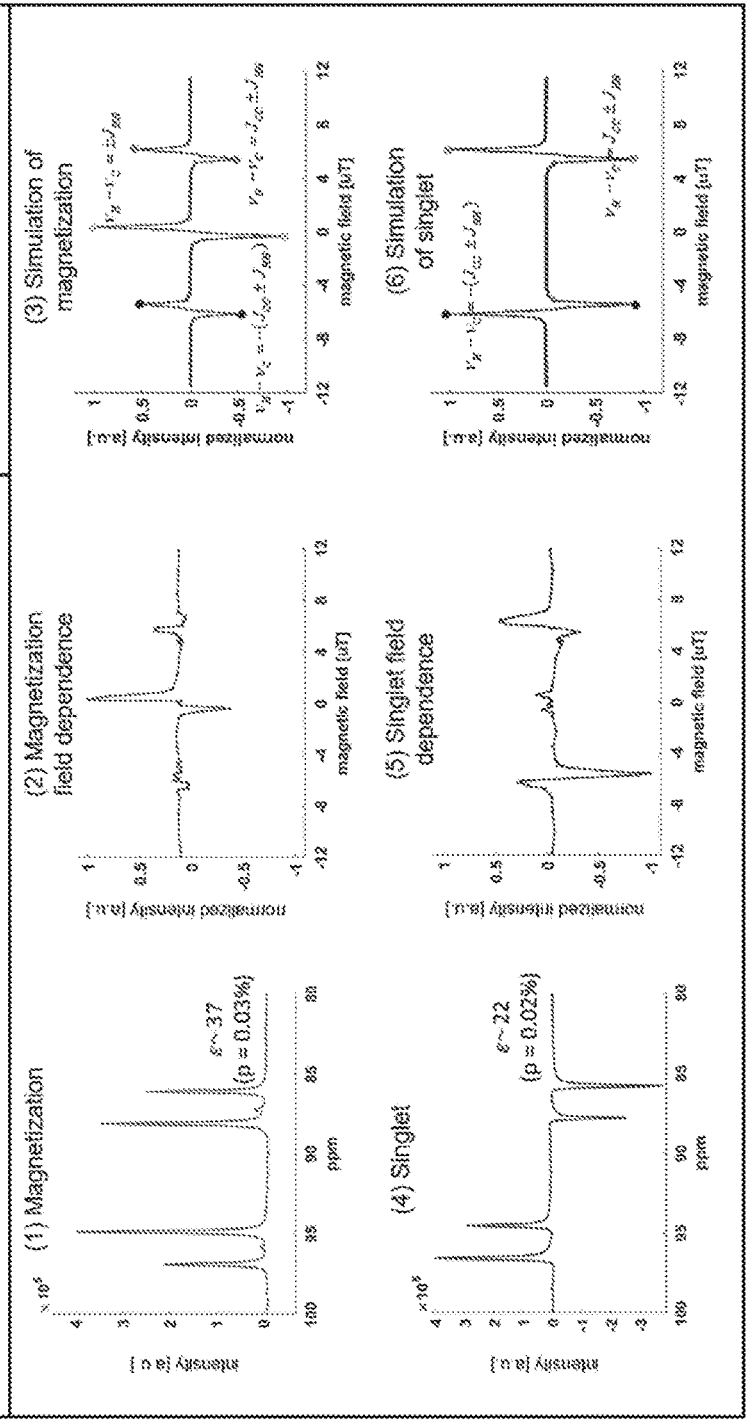
FIG. 25B
FIG. 25

Activation

Equilibria and Energies of interest:

US 11,016,152 B2

METHOD FOR CREATING HYPERPOLARIZATION AT MICROTESLA MAGNETIC FIELDS

CROSS REFERENCE TO RELATED APPLICATIONS

This application is the U.S. national stage entry, under 35 U.S.C. § 371, of International Application Number PCT/US2018/032485, filed May 12, 2018, which claims priority to U.S. Provisional Application No. 62/505,721, filed May 12, 2017, the entire contents of each of which are herein incorporated by reference.

STATEMENT OF GOVERNMENT INTEREST

This invention was made with government support under Awards Nos. CHE-1058727, CHE-1363008, CHE-1416268 and CHE-1416432, each awarded by the National Science Foundation, Award Nos. 1R21EB018014, 1R21EB020323, and 1R21CA220137, each awarded by the National Institutes of Health, and Award Nos. W81XWH-12-1-0159/BC112431, W81XWH-15-1-0271 and W81XWH-15-1-0272, each awarded by the Department of Defense. The Government has certain rights in the invention.

TECHNICAL FIELD

The present disclosure relates to methods for nuclear spin polarization enhancement at very low magnetic fields (e.g., significantly lower than magnetic field of Earth of ~50 microTesla) via signal amplification by reversible exchange.

BACKGROUND

Nuclear magnetic resonance (NMR) and magnetic resonance imaging (MRI) sensitivity can be enhanced through hyperpolarization by temporarily increasing the relatively low nuclear spin polarization ($P=10^{-6}$–$10^{-5}$)—in some cases approaching unity—effectively providing $10^4$–$10^5$-fold NMR signal enhancement. Despite the short-lived nature of hyperpolarized (HP) spin states, with typical lifetimes on the order of seconds for $^1H$ or minutes for heteronuclei (e.g., $^{15}N$, $^{13}C$), the considerable sensitivity gain has led to many biomedical applications where a given HP compound serves as injectable or inhalable contrast agent.

Current hyperpolarization methods for preparation of HP contrast agents include dissolution dynamic nuclear polarization (d-DNP). However, d-DNP is expensive, complex and not easily scalable. Another route to address the NMR/MRI sensitivity problem is the use of parahydrogen (abbreviated here asp-$H_2$ or para-$H_2$) as the hyperpolarization source, as is done in a family of techniques referred to collectively as Parahydrogen-Induced Polarization (PHIP). In traditional PHIP, molecular precursors with unsaturated chemical bonds are hydrogenated via molecular addition of para-$H_2$, thereby transferring the nuclear spin order to the molecular products. HP $^{13}C$ molecules produced by this approach have been efficiently used as HP contrast agents in vivo.

In a more recent technique known as Signal Amplification by Reversible Exchange (SABRE), spin order may be transferred from para-$H_2$ to target molecules during the lifetime of transient molecular complexes without permanent chemical change. SABRE generally uses an organometallic catalyst to transiently co-locate para-$H_2$ and the target substrate molecule in a low-symmetry complex in solution. In low field (e.g., 5-7 mT), net spin order can be transferred from the para-$H_2$ to the spins of the substrate via scalar couplings. SABRE derived proton hyperpolarization can be transferred to heteronuclei, but the associated efficiency is low. Accordingly, there exists a need for improved methods of hyperpolarization of heteronuclei.

SUMMARY

The present disclosure provides methods of hyperpolarizing heteronuclei, comprising: (a) combining a plurality of molecules of parahydrogen, a plurality of molecules of a catalyst, and a plurality of molecules of a compound, where the compound includes a heteronucleus and another atom that exists naturally as either a quadrupolar or a non-quadrupolar isotope, where the heteronucleus in at least 50% of the plurality of molecules of the compound is a hyperpolarizable heteronucleus, and where the plurality of molecules of the compound have been modified so as to isotopically enrich the other atom with the non-quadrupolar isotope, and where the parahydrogen, the compound and the catalyst associate to form a complex; and (b) applying a magnetic field with a strength of less than 50 µT to the complex, thereby transferring the spin order from the parahydrogen to the hyperpolarizable heteronucleus associated with the complex.

Other aspects of the present disclosure include methods of performing NMR experiments, methods of obtaining MRI images, and other methods of in vivo imaging.

BRIEF DESCRIPTION OF THE DRAWINGS

FIG. 1A: Schematic diagram of the SABRE process: coherent transfer of spin order from parahydrogen-derived hydride protons to $^{13}C$ heteronuclei. FIG. 1B: Molecular structure of $^{15}N$-labeled pyridine with naturally abundant $^{13}C$ (percentage of $^{13}C$ in the corresponding position is shown). FIG. 1C: Most-probable $^{15}N$-pyridine-bound structures of the complex with relevant AA'B spin systems responsible for the polarization transfer. L denotes ligand, and C denotes a HP $^{13}C$ spin within a ligand.

FIGS. 4A and 4B show $^{13}C$ NMR single-scan spectra of acetonitrile-1-$^{13}C$,$^{14}N$ and acetonitrile-1-$^{13}C$,$^{15}N$ hyperpolarized using SABRE-SHEATH and measured at 8.45 T. FIG. 4A: A comparison of acetonitrile-1-$^{13}C$,$^{15}N$ (red) and acetonitrile-$^{13}C$,$^{15N}$ (blue) using the same experimental conditions (100 mM of acetonitrile, 5 mM of catalyst, 30 mM of pyridine used as a co-substrate). FIG. 4B: $^{13}C$ NMR spectrum of hyperpolarized acetonitrile-1-$^{13}$C,$^{15}$N (sample composition ~0.6 mM of acetonitrile-1-$^{13}$C,$^{15}$N, 0.2 mM of catalyst, 0.4 mM of pyridine used as a co-substrate).

FIG. 8A: $^{19}$F 2D gradient echo (GRE) imaging using ~100 mM HP substrate; FIG. 8B: corresponding $^{19}$F 2D GRE image using ~100 mM thermally polarized substrate; FIG. 8C: schematic of experimental MRI setup; both images were acquired using a 4.7 T small-animal ~30 cm bore MRI scanner (proton channel) equipped with a surface RF coil tuned to ~188.4 MHz and the following acquisition parameters: field of view (FOV): 128×128 mm$^2$; imaging matrix: 256×256 pixels; TR/TE=12/6 ms; scan time: ~3 s; frequency encoding bandwidth=50 kHz. FIG. 8D: HP $^{19}$F MR spectra demonstrating pH sensing, before (red) and after (blue) addition of concentrated HCl to ~100 mM HP substrate.

FIG. 14A: Thermally polarized spectrum provided for signal referencing. FIG. 14B: NMR spectrum of SABRE-hyperpolarized solution (at ~6 mT) after cessation of para-H$_2$ bubbling (FIG. 12A). FIG. 14C: NMR spectrum of SABRE-hyperpolarized (at ~6 mT) solution after frequency-selective RF irradiation leading to selective destruction of Ha hyperpolarization; FIG. 14D: the corresponding NMR spectrum after the sample prepared in c) was re-hyperpolarized at ~6 mT without para-H$_2$ bubbling (FIG. 12B). The overall signal intensity of the spectrum shown in FIG. 14D decreased compared to that in spectrum FIG. 14C due to relaxation processes leading to polarization decay during the additional ~6 s required for sample shuttling. The total shuttling time (after cessation of para-H$_2$ bubbling) for spectrum d is >10 s, i.e. more than 3*T$_1$ of hydrides, and significantly shorter than Ti of aromatic protons (19±1 s), and therefore, it was concluded that the residual polarization of hydrides cannot serve as a source of re-polarization in spectrum in spectrum d.

FIGS. 16A-16G show NMR spectra of metronidazole-$^{15}$N$_2$-$^{13}$C$_2$ hyperpolarized using SABRE-SHEATH setup (FIG. 13A). FIG. 16A: HP $^{15}$N NMR spectrum, FIG. 16B: $^{15}$N spectrum from a thermally polarized reference sample, FIG. 16C: HP $^{13}$C NMR spectrum, FIG. 16D: $^{13}$C spectrum from a thermally polarized reference sample, FIG. 16E: HP $^1$H NMR spectrum (polarization at ~6 mT), FIG. 16F: $^1$H spectrum from a thermally-polarized sample, FIG. 16G: HP $^1$H NMR spectrum (polarization at <1 µT), All spectra were recorded using Bruker Avance III 9.4 T NMR spectrometer.

FIGS. 17E and 17F: SABRE relevant spin-spin couplings for direct polarization transfer.

FIG. 18 shows $^{15}$N NMR spectra of HP metronidazole-$^{15}$N$_2$-$^{13}$C$_2$. FIG. 18A: after SABRE-SHEATH hyperpolarization at µT field, cessation of para-H$_2$ bubbling, and HP sample transfer to the 9.4 T NMR spectrometer followed by frequency-selective polarization destruction of $^{15}$N$_3$ site. FIG. 18B: the spectrum obtained via the procedure described in FIG. 18A followed by magnetic field cycling (MFC) to the Earth's magnetic field and then back to the 9.4 T NMR spectrometer; FIG. 18C: after SABRE hyperpolarization at the Earth's magnetic field, cessation of para-H$_2$ bubbling, and HP sample transfer to the 9.4 T NMR spectrometer; FIG. 18D: the spectrum obtained by the procedure described in FIG. 18A followed by 180° phase inversion of the $^{15}$N polarization; and FIG. 18E: the spectrum attained by the procedure described in FIG. 18D, followed by magnetic field cycling (MFC) to the Earth's magnetic field and then returned to the 9.4 T NMR spectrometer. See FIG. 13B for details. All NMR spectra are acquired using 90° excitation RF pulse after the respective manipulations.

FIG. 19A: after SABRE-SHEATH hyperpolarization at µT magnetic field, cessation of para-H$_2$ bubbling, and HP sample transfer into 9.4 T NMR spectrometer followed by frequency-selective polarization destruction of $^{15}$N$_1$ site; FIG. 19B: the sample produced by the procedure described in FIG. 19A followed by the magnetic field cycling (MFC) to the Earth's magnetic field (ca. 50 µT) and then back in the 9.4 T NMR spectrometer; FIG. 19C: the sample produced by the procedure described in FIG. 19A followed by 180° phase inversion of $^{15}$N polarization; FIG. 19D: the sample produced by the procedure described in FIG. 19C followed by the magnetic field cycling (MFC) to the Earth's magnetic field (ca. 50 µT) and then back in the 9.4 T NMR spectrometer. All NMR spectra are acquired using 90° excitation RF pulse after the respective manipulations.

FIG. 20 shows $^{13}$C NMR spectra of HP metronidazole-$^{15}$N$_2$-$^{13}$C$_2$. FIG. 20A: spectrum obtained After SABRE-SHEATH hyperpolarization at µT magnetic field, followed by cessation of para-H$_2$ bubbling, and sample transfer to the 9.4 T NMR spectrometer, followed by $^1$H and $^{13}$C polarization destruction (via applying a series of 90° RF pulses to $^{13}$C spins and $^1$H decoupling to $^1$H spins); FIG. 20B: the spectrum obtained by the procedure described in FIG. 42A but followed by magnetic field cycling (MFC) to the µT regime (i.e. within a magnetic shield) and then after the sample was returned to the 9.4 T NMR spectrometer. FIG. 20C: the spectrum obtained by the procedure described in FIG. 20A but followed by magnetic field cycling (MFC) to the Earth's magnetic field prior to return to the 9.4 T NMR spectrometer. All NMR spectra shown were acquired using a 90° excitation RF pulse after the respective manipulations described herein.

FIG. 21A: NMR spectrum of SABRE-hyperpolarized solution after cessation of para-H$_2$ bubbling. FIG. 21B: Thermally polarized spectrum provided for signal referencing. FIG. 21C: NMR spectrum of SABRE-hyperpolarized (at ~6 mT) solution after frequency-selective RF irradiation leading to selective destruction of Hc hyperpolarization; FIG. 21D: the corresponding NMR spectrum after the sample prepared in FIG. 21C was re-hyperpolarized at ~6 mT without para-H$_2$ bubbling. FIG. 21E: NMR spectrum of SABRE-hyperpolarized (at ~6 mT) solution after frequency-selective RF irradiation leading to selective destruction of Hb hyperpolarization. FIG. 21F: the corresponding NMR spectrum after the sample was re-hyperpolarized at ~6 mT without para-H$_2$ bubbling.

FIG. 22 shows $^{15}$N NMR spectra of HP metronidazole-$^{15}$N$_2$-$^{13}$C$_2$: FIG. 22A: after SABRE-SHEATH hyperpolarization at µT field, cessation of para-H$_2$ bubbling, and the HP sample transfer in 9.4 T NMR spectrometer followed by frequency-selective polarization destruction of $^{15}$N$_3$ site; FIG. 22B: the sample produced by the procedure described in (a) followed by the magnetic field cycling (MFC) to the fringe field of ~6 mT and then back in the 9.4 T NMR spectrometer; FIG. 22C: the sample produced by the procedure described in FIG. 44A followed by the magnetic field cycling (MFC) to the Earth's magnetic field and then back in the 9.4 T NMR spectrometer; FIG. 22D: after SABRE hyperpolarization at the Earth's magnetic field, cessation of para-H$_2$ bubbling, and the HP sample transfer in 9.4 T NMR spectrometer; FIG. 22E: the sample produced by the procedure described in FIG. 22A followed by the magnetic field cycling (MFC) to µT field and then back in the 9.4 T NMR spectrometer; FIG. 22F: the sample produced by the procedure described in FIG. 22A followed by 180° phase inversion of $^{15}$N polarization; FIG. 22G: the sample produced by the procedure described in FIG. 22F followed by the magnetic field cycling (MFC) to the Earth's magnetic field and then back in the 9.4 T NMR spectrometer. All NMR spectra are acquired using 90° excitation RF pulse after the manipulation described herein.

FIG. 23 shows $^{13}$C spectra of naturally abundant (FIGS. 23A and 23B) and $^{13}$C labelled (FIGS. 23C and 23D) substrates used in experiments. FIGS. 23A and 23C show results for the symmetrically substituted 1,2-2 pyridyl acetylene. FIGS. 23B and 23D are from the asymmetrically substituted 1-phenyl-2-(4-pyridyl) acetylene. For the naturally abundant substrates the bridge carbons on the pyridyl rings (3, 4 in FIG. 23A, 3 in FIG. 23B) show significant enhancement, while the one on the benzene ring (4 in FIG. 23B) is only slightly hyperpolarized. The $^{13}$C-$^{13}$C coupling, $J_{CC}$, read from the line-splitting in panel D is 185 Hz.

FIG. 24 shows two possible polarization transfer catalysts (PTC's). Top: 3D models obtained after energy minimization in the all electron code FHI-aims. Bottom: Structural formulas of the PTCs for clarity. FIG. 24A shows the substrate is bound to all Ir binding sites via nitrogen. FIG. 24B shows one of the molecules' triple bond binds to the iridium catalyst, which has a higher energy than the structure in FIG. 24A. DFT calculations reveal that the energy difference between the two proposed complexes is relatively small (0.09 eV).

FIG. 25 shows field dependent hyperpolarization for the two substrates. FIG. 25A shows (1) a hyperpolarized magnetization spectrum hyperpolarized at 0.17 µT (and acquired at 8.45 T) for the symmetric substrate and (2) its field dependence in the µT range. FIG. 25B shows the experimental and simulated results of creating magnetization and singlet order for the asymmetric substrate, as function of magnetic field; (1) Magnetization spectrum hyperpolarized at 0.28 µT. (2) Experimental and (3) simulated field dependence for magnetization. (4) Singlet spectrum hyperpolarized at 6.2 μT. (5) Experimental and (6) simulated field dependence for singlet order. In FIG. 25B panels (3) and (6), the highlighted points are the local maxima for polarization transfer labeled by analytically derived resonance conditions from careful inspection of the nuclear-spin Hamiltonian.

DETAILED DESCRIPTION

Figure 2A:
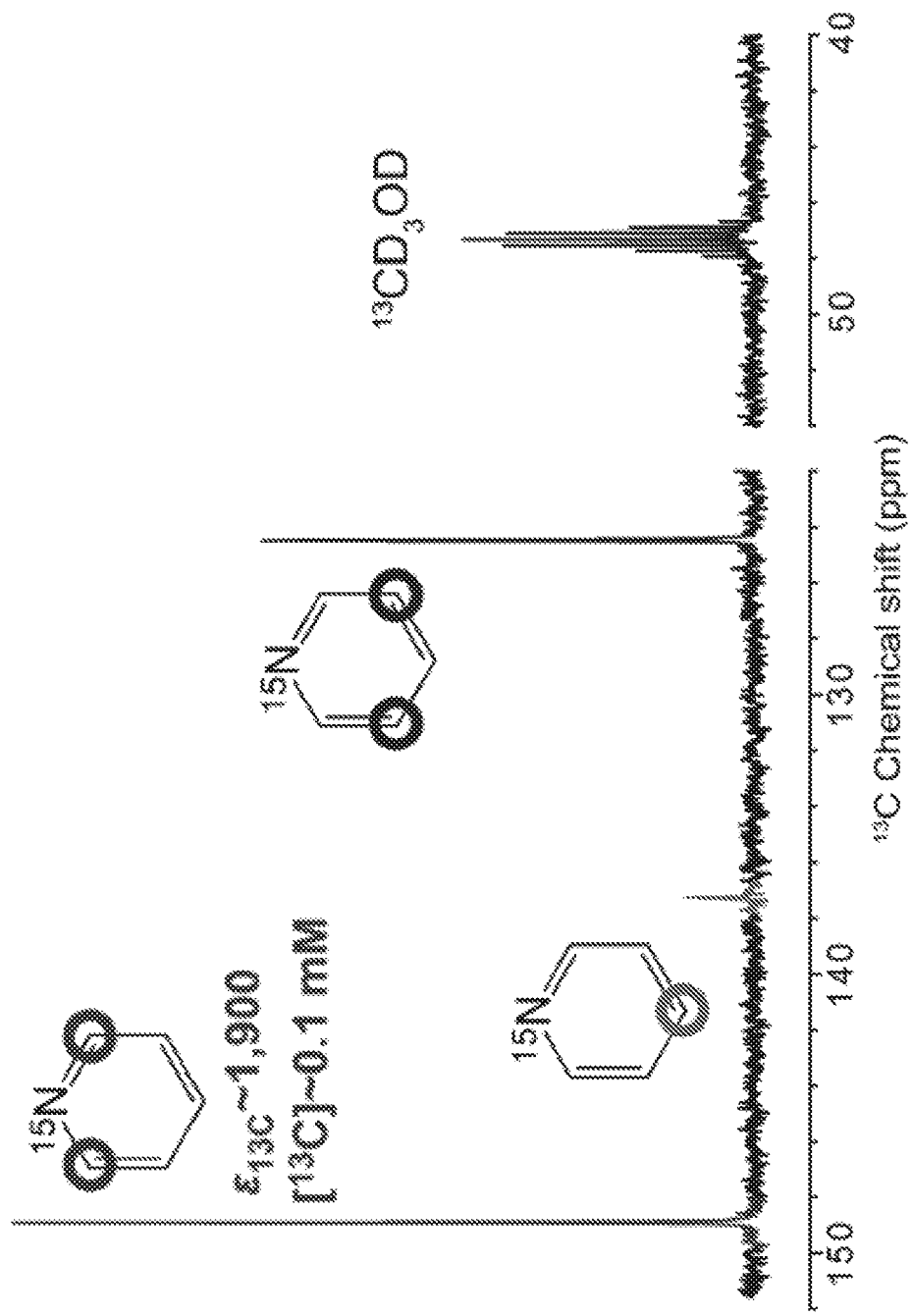
FIG. 2A: Proton-decoupled $^{13}C$ NMR spectrum of SABRE-hyperpolarized 5 mM $^{15}N$-pyridine (left) at $^{13}C$ natural abundance; a $^{13}C$ NMR spectrum of thermally polarized $CD_3OD$ is shown (right) for comparison.

The present disclosure relates to methods of directly transferring para-$H_2$ polarization to heteronuclei without the need of rf irradiation or pulses. This hyperpolarization strategy may be referred to as SABRE-SHEATH (SABRE in SHield Enables Alignment Transfer to Heteronuclei). Various aspects of the SABRE-SHEATH methods are described in U.S. patent application Ser. No. 14/925,507 to Warren et al. ("METHOD FOR CREATING HYPERPOLARIZATION AT MICROTESLA MAGNETIC FIELDS," filed Oct. 28, 2015), which is herein incorporated by reference in its entirety.

In some aspects, the present disclosure provides improvements over existing methods of hyperpolarization of heteronuclei. For example, the disclosed methods demonstrate that the absence of quadrupolar nuclei may facilitate efficient $^{13}C$ hyperpolarization via reversible exchange with parahydrogen, and that spin relays may enable efficient long-range heteronuclear signal amplification by reversible exchange.

The advantages of the disclosed method promote the broad applicability of SABRE-SHEATH in biophysical and biomedical imaging experiments, allowing this technique to be useful, for example, in minimally invasive biomedical applications.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrases "at least one of A, B, . . . and N" or "at least one of A, B, . . . N, or combinations thereof" are defined in the broadest sense to mean one or more elements selected from the group comprising A, B, . . . and N, that is to say, any combination of one or more of the elements A, B, . . . or N including any one element alone or in combination with one or more of the other elements which may also include, in combination, additional elements not listed.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The term "heterogeneous catalyst," as used herein, means a catalyst that is in a separate phase from the reactants. For example, the heterogeneous catalyst used in the methods described herein may be a heterogeneous catalyst in U.S. patent application Ser. No. 14/801,541, the contents of which are incorporated herein in their entirety. The heterogeneous transition metal catalyst described herein may also be in U.S. patent application Ser. No. 14/801,541.

The term "homogeneous catalyst," as used herein, means a catalyst that is in the same phase as the reactants. For example, the homogeneous catalyst used in the methods described herein may be a homogeneous catalyst in U.S. patent application Ser. No. 14/801,554, the contents of which are incorporated herein in their entirety. The homogeneous transition metal catalyst described herein may also be in U.S. patent application Ser. No. 14/801,554.

The term "isotopically enriched," as used herein with reference to any particular isotope of any particular atom of a compound, means that in a composition comprising a plurality of molecules of the compound, the amount (e.g., fraction, ration or percentage) of the plurality of molecules having the particular isotope at the particular atom is substantially greater than the natural abundance of the particular isotope, due to synthetic enrichment of the particular atom with the particular isotope. For example, a composition comprising a compound with an isotopically enriched $^{15}N$ atom at a particular location includes a plurality of molecules of the compound where, as a result of synthetic enrichment, the percentage of the plurality of molecules having $^{15}N$ at that location is greater than about 1% (the natural abundance of $^{15}N$ is substantially less than 1%), and in many cases is substantially greater than about 1%. Similarly, a composition comprising a compound with an isotopically enriched deuterium (D) atom at one or more particular locations includes a plurality of molecules of the compound, where as a result of synthetic enrichment, the percentage of the plurality of molecules having D at each of the one or more particular locations is greater than about 1% (the natural abundance of D is substantially less than 1%), and in many cases is substantially greater than about 1%. In some cases, a composition comprising a compound with an isotopically enriched atom at a particular location may include a plurality of molecules of the compound, where the amount of the plurality of molecules having the isotope at the location may be at least about two-or-more-fold greater than the natural abundance of the isotope, including but not limited to at least about two-fold, at least about three-fold, at least about four-fold, at least about five-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, and at least about 200-fold, among others. In some cases, a composition comprising a compound with an isotopically enriched atom at a particular location also may include a plurality of molecules of the compound where, as a result of synthetic enrichment, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, of the plurality of molecules have the isotope at the location.

The term "natural abundance," as used herein with reference to any particular isotope of an element, refers to the abundance of the isotope as naturally found on the planet Earth. For example, the natural abundance of $^{15}N$ on the planet Earth is generally regarded to be about 0.37% (i.e., substantially less than about 1%), while the natural abundance of deuterium (D) on the planet Earth is generally regarded to be about 0.015% (i.e., substantially less than about 1%).

2. Methods of Hyperpolarizing Heteronuclei

In some aspects, the present disclosure provides methods of hyperpolarizing heteronuclei, comprising:

(a) combining a plurality of molecules of parahydrogen, a plurality of molecules of a catalyst, and a plurality of molecules of a compound, where the compound includes a heteronucleus and another atom that exists naturally as either a quadrupolar or a non-quadrupolar isotope, where the heteronucleus in at least 50% of the plurality of molecules of the compound is a hyperpolarizable heteronucleus, and where the plurality of molecules of the compound have been modified so as to isotopically enrich the other atom with the non-quadrupolar isotope, and where the parahydrogen, the compound and the catalyst associate to form a complex; and (b) applying a magnetic field with a strength of less than 50 µT to the complex, thereby transferring the spin order from the parahydrogen to the hyperpolarizable heteronucleus associated with the complex.

In general, the present methods may be used to hyperpolarize the heteronuclei of a plurality of molecules of a compound, in order to enhance the NMR measurements of such heteronuclei in the compound. The compound may include a heteronucleus and another atom. Typically in the present method, the parahydrogen, the compound, and the catalyst are mixed, such that they associate to form a complex. In some embodiments, as a result of the forming a complex, the parahydrogen, the heteronucleus, and the other atom are in the same hyperpolarization/coupling network within the complex.

In some embodiments, the compound is a contrast agent for an in vivo imaging technique. Example of suitable contrast agents may include, but are not limited to, metronidazole, other nitroimidazole-based antibiotics and synthetic derivatives, imidazole as a pH sensor, nicotinamide, DNA bases, synthetic DNA bases and their derivatives, polypeptides and proteins.

Suitable hyperpolarizable heteronuclei may include, but are not limited to $^{13}C$, $^{15}N$, $^{19}F$, $^{9}Si$, $^{31}P$, $^{129}Xe$, $^{7}Li$, $^{89}Y$, $^{107}Ag$, and $^{109}Ag$. In some embodiments, the hyperpolarizable heteronucleus is $^{13}C$. In some embodiments, the hyperpolarizable heteronucleus is $^{19}F$. In some embodiments, the hyperpolarizable heteronucleus is $^{15}N$, $^{29}Si$, $^{31}P$, $^{129}Xe$, $^{7}Li$, $^{89}Y$, $^{107}Ag$ or $^{199}Ag$.

In some embodiments, the heteronucleus in at least 50% of the plurality of molecules of the compound is a hyperpolarizable heteronucleus. For example, in some embodiments, the heteronucleus in at least 55%, at least 60%, at least 65%, at least 70%, at least 75%, at least 80%, at least 85%, at least 90%, at least 95%, at least 97%, at least 98%, or even at least 99% of the plurality of molecules of the compound is a hyperpolarizable heteronucleus.

The other atom may exist naturally as either a quadrupolar or a non-quadrupolar isotope. In some embodiments, the methods of the present disclosure may include modifying the plurality of molecules of the compound so as to isotopically enrich the other atom with the non-quadrupolar isotope. In some embodiments, the non-quadrupolar isotope of the other atom has a nuclear spin of 0 or ½. In some embodiments, the other atom is a nitrogen atom, and the plurality of molecules of the compound have been modified so as to isotopically enrich the nitrogen atom with $^{15}N$.

In some embodiments, the other atom is a hydrogen atom, and the plurality of molecules of the compound have been modified so as to isotopically enrich the hydrogen atom with $^{1}H$.

In some embodiments, the spin order is transferred during a temporary association of parahydrogen, the compound, and the catalyst while maintaining the chemical identity of the compound.

In some embodiments, the magnetic field is determined by matching the resonance frequency of parahydrogen with the resonance frequency of at least one hyperpolarizable nucleus of the compound.

In some embodiments, the magnetic field has a strength of from about 0.1 to about 20 μT, including but not limited to a range from about 0.1 to about 15 μT, from about 0.1 to about 10 μT, from about 0.1 to about 5 μT, from about 0.1 to about 2 μT, from about 0.1 to about 1 μT, or from about 0.1 to about 0.5 μT. In some embodiments, the magnetic field has a strength of less than 20 μT. In some embodiments, the magnetic field has a strength of about 0.1 to about 1 μT.

The catalyst used in the present method may be a heterogeneous or a homogeneous catalyst. In some embodiments, the catalyst is a heterogeneous catalyst. In some embodiments, the catalyst is a homogeneous catalyst. In some embodiments, the catalyst comprises a transition metal. For example, in some embodiments, the catalyst comprises a transition metal, and the transition metal in the complex coordinates with the other atom. In particular embodiments, the transition metal is iridium.

The catalyst may be activated prior to forming the complex. For example, the pre-activation catalyst may be selected from the group consisting of [IrCl(COD)(IMes)], [IrCl(IDEG)(COD)], [IrCl(CODDA)-IMes], [IrCl(COD)(SIMes)], among others.

The catalyst may be homogeneous or heterogeneous, wherein the catalyst accommodates the simultaneous exchange of para-$H_2$ and heteronuclear spin center(s), and wherein the condition of spin-spin (weak or strong J) coupling between para-$H_2$ derived protons and heteronuclear spin center(s) is maintained.

The heteronucleus may be a first heteronucleus and the compound further may include a second heteronucleus, where the second heteronucleus in at least 50% of the plurality of molecules of the compound is a hyperpolarizable heteronucleus, wherein when the first and second heteronuclei are both hyperpolarizable, the first and second heteronuclei are a J-coupled pair; wherein upon applying the magnetic field with a strength of less than 50 $_FIT$ to the complex, the spin order from the parahydrogen is transferred to the J-coupled pair, thereby inducing a hyperpolarized long-lived spin state.

3. Examples

Various experimental procedures for SABRE studies and measurements may be carried out as described in U.S. patent application Ser. No. 14/925,507 (incorporated herein by reference in its entirety), including: SABRE catalyst and sample preparation, experimental SABRE setup (for example, at 9.4 T), calculations of NMR polarization enhancements (for example, at 9.4 T), and SABRE-SHEATH neat liquid experiments.

Example 1. The Absence of Quadrupolar Nuclei Facilitates Efficient $^{13}C$ Hyperpolarization Via Reversible Exchange with Parahydrogen Nuclear spin hyperpolarization techniques are revolutionizing the field of $^{13}C$ molecular MRI. While dissolution Dynamic Nuclear Polarization (d-DNP) is currently the leading technique, it is generally slow (requiring ~1 h) and costly (~$USD10^6$). As a consequence of carbon's central place in biochemistry, tremendous progress using $^{13}C$ d-DNP bioimaging has been demonstrated to date including a number of clinical trials. Despite numerous attempts to develop alternatives to d-DNP, the competing methods have faced significant translational challenges. Efficient hyperpolarization of $^{15}N$, $^{31}P$, and other heteronuclei using Signal Amplification By Reversible Exchange (SABRE) has been reported in 2015, but extension of this technique to $^{13}C$ has proven to be challenging. In some embodiments, disclosed herein is efficient hyperpolarization of $^{13}C$ nuclei using micro-Tesla SABRE. Up to ca. 6,700-fold enhancement of nuclear spin polarization at 8.45 T is achieved in seconds, corresponding to $P_{13C}$~4.4% using 50% parahydrogen ($P_{13C}$>14% would be feasible using more potent ~100% parahydrogen). Importantly, the $^{13}C$ polarization achieved via SABRE strongly depends not only upon spin-lattice relaxation, but also upon the presence of $^{15}N$ (I=½) versus quadrupolar $^{14}N$ (I=1) spins in the site binding the hexacoordinate Ir atom of the catalytic complex. It is shown that different $^{13}$C nuclei in the test molecular frameworks—pyridine & acetonitrile—can be hyperpolarized, including $^{13}$C sites up to 5 chemical bonds away from the exchangeable hydrides. The presented approach is highly scalable, and can be applied to a rapidly growing number of biomolecules amendable to micro-Tesla SABRE.

Hyperpolarization techniques temporarily increase nuclear spin polarization (typically ~$10^{-5}$-$10^{-6}$ at equilibrium Boltzmann distribution even when using high-field magnets) up to the order of unity. This dramatic enhancement of nuclear spin polarization and resulting magnetic resonance signals opens new horizons for NMR spectroscopy and MRI imaging. Importantly, hyperpolarization technologies have enabled a wide range of new biomedical applications, which are now key drivers of hyperpolarization technique developments. Most importantly, in vivo molecular imaging of $^{13}$C metabolites at millimolar concentrations is now possible. Carbon has an undisputable central role in biochemistry, and $^{13}$C-based hyperpolarized (HP) contrast agents have been successfully employed for metabolic imaging during health and disease—including detection of abnormal metabolism of cancer and monitoring treatment response. This field has rapidly progressed from proof-of-principle studies to the first clinical trials.

Dissolution Dynamic Nuclear Polarization (d-DNP) is currently the leading hyperpolarization technique for production of a wide range of HP $^{13}$C contrast agents. However, this technique has several shortcomings for widespread biomedical use. In particular, the clinical-scale device is costly, and has sophisticated siting requirements. Moreover, d-DNP hyperpolarization takes ~1 h, although recent progress enables acceleration of the process.

Several alternative techniques for $^{13}$C hyperpolarization have been developed that address the shortcomings of d-DNP. So far, only parahydrogen-induced polarization (PHIP) has demonstrated the ability to produce HP $^{13}$C contrast agents for in vivo use, but PHIP is restricted to a handful of molecular frameworks (requiring sophisticated spin labeling strategies, e.g. deuteration, in addition to $^{13}$C enrichment) of unsaturated precursors for parahydrogen addition.

A PHIP variant that lifts these restrictions is Signal Amplification by Reversible Exchange (SABRE). SABRE was first introduced by Duckett and Green in 2009. It relies on the reversible exchange of parahydrogen (p-H$_2$) and the to-be-hyperpolarized substrate on a metal complex. Generally, following hyperpolarization of p-H$_2$-nascent proton spins, polarization transfer can be employed to heteronuclear low-gamma (e.g. $^{13}$C and $^{15}$N) sites using radio-frequency (RF) pulse sequences. Storing polarization on heteronuclear sites carries advantages of significantly longer lifetime with relaxation decay time constants of up to 20 minutes. However, coherent polarization transfer without RF pulses, i.e. using the matching static magnetic field, has proven to be significantly more efficient, and significantly less instrumentationally demanding. Indeed, the original $^1$H SABRE demonstration has led to achieving P$_H$ in excess of 10% at matching fields on the order of a few milliTesla. The matching static magnetic field for heteronuclei (e.g. $^{15}$N and $^{31}$P) that yields maximal SABRE enhancement is in the micro-Tesla range. This approach (termed SABRE in SHield Enables Alignment Transfer to Heteronuclei or SABRE-SHEATH) is very efficient; it has already achieved Pisa in excess of 20% within a minute, and has been expanded to pH and hypoxia sensors, among others. $^{15}$N SABRE-SHEATH employs long-range $^1$H-$^{15}$N spin-spin couplings between p-H$_2$-derived hydride protons and the $^{15}$N spins of the target substrate, enabling coherent transfer of spin order in micro-Tesla magnetic fields. While $^{15}$N-based HP contrast agents will likely find their use in biomedical applications, efficient and direct $^{13}$C SABRE hyperpolarization has not been demonstrated to date despite multiple efforts and significant interest.

In some embodiments, disclosed herein is efficient $^{13}$C hyperpolarization of pyridine (Py) using the SABRE-SHEATH approach (FIG. 1), where polarization coherently transfers from nascent p-H$_2$ protons to $^{13}$C nuclei at matching micro-Tesla magnetic fields. Py was chosen for the present work given that it is the most studied model compound for SABRE. $^{13}$C SABRE-SHEATH experiments were performed using the most efficient SABRE catalyst Ir-IMes (using the established Ir catalyst precursor [IrCl(COD)(IMes)]; IMes=1,3-bis(2,4,6-trimethylphenyl)-imidazol-2-ylidene; COD=cyclooctadiene), and the corresponding active hexacoordinate complex is shown in FIG. 1A. $^{15}$N-labeled pyridine (Py-$^{15}$N) was employed, providing a convenient means of studying hyperpolarization of three $^{13}$C sites at the natural abundance level of $^{13}$C (FIG. 1B). FIG. 1C shows the chemical structures of the most probable complexes relevant for coherent SABRE-SHEATH polarization transfer in the three-spin system described by us previously in the context of $^{15}$N SABRE-SHEATH. This approach allowed us to probe $^{13}$C SABRE-SHEATH polarization transfer via 3-, 4-, and 5-bond spin-spin couplings $J_{1H-13C}$, respectively.

Indeed, proton-decoupled $^{13}$C spectra (FIG. 2A) of HP Py-$^{15}$N exhibit $^{13}$C signal enhancements up to ~1,900 fold at 9.4 T, corresponding to P$_{13C}$~1.5%. Qualitatively, the $^{13}$C signal enhancement was the most efficient for the ortho-position, followed by the meta- and para-$^{13}$C positions—corresponding to 3-, 4-, and 5-bond $^1$H-$^{13}$C spin-spin couplings, respectively. This trend is in qualitative agreement with previous $^{15}$N SABRE-SHEATH studies, which have shown that the polarization efficiency was better when spin order was transferred via two-bond heteronuclear spin-spin coupling compared to that for four- and five-bond heteronuclear spin-spin couplings. We note that the $^{13}$C enhancement (reflecting the efficiency of $^{13}$C SABRE-SHEATH) was maximized with respect to the flow rate of p-H$_2$ at ~7 atm p-H$_2$ pressure (FIG. 2B), and optimized with respect to temperature and micro-Tesla magnetic field of SABRE-SHEATH polarization transfer, FIGS. 2F and 2G, respectively. While these feasibility results are promising, the achieved P$_{13C}$ value is roughly 3-fold lower than the corresponding P$_{15N}$ value obtained via $^{15}$N SABRE-SHEATH under similar conditions. This difference can be explained in part by very short HP $^{13}$C T$_1$'s at both the Earth's field and high (9.4 T) magnetic field of 5-8 s (FIGS. 2D and 2E), values that are approximately 3-5-fold lower than those of $^{15}$N sites at similar conditions. Consequently, the P$_{13C}$ losses during the ~6-second-long sample transfer (from the SABRE-SHEATH shield into the detection coil of the 9.4 T NMR magnet) are significant compared to the relatively small P$_{15N}$ relaxation losses during sample transfer. If these losses were mitigated by hyperpolarization of longer-lived $^{13}$C sites, the observable P$_{13C}$ would likely be increased by several folds. We emphasize that the $^{13}$C T$_1$'s in the studied system are likely limited due (i) to the strong (ca. 160-180 Hz) $^1J_{1H-13C}$ couplings (Table 1) and (ii) dipolar interactions with directly bound protons (and potentially large $^{13}$C CSA at high magnetic field), rather than being limited by the interactions with the catalyst, as in the case of $^{15}$N.

Figure 3:
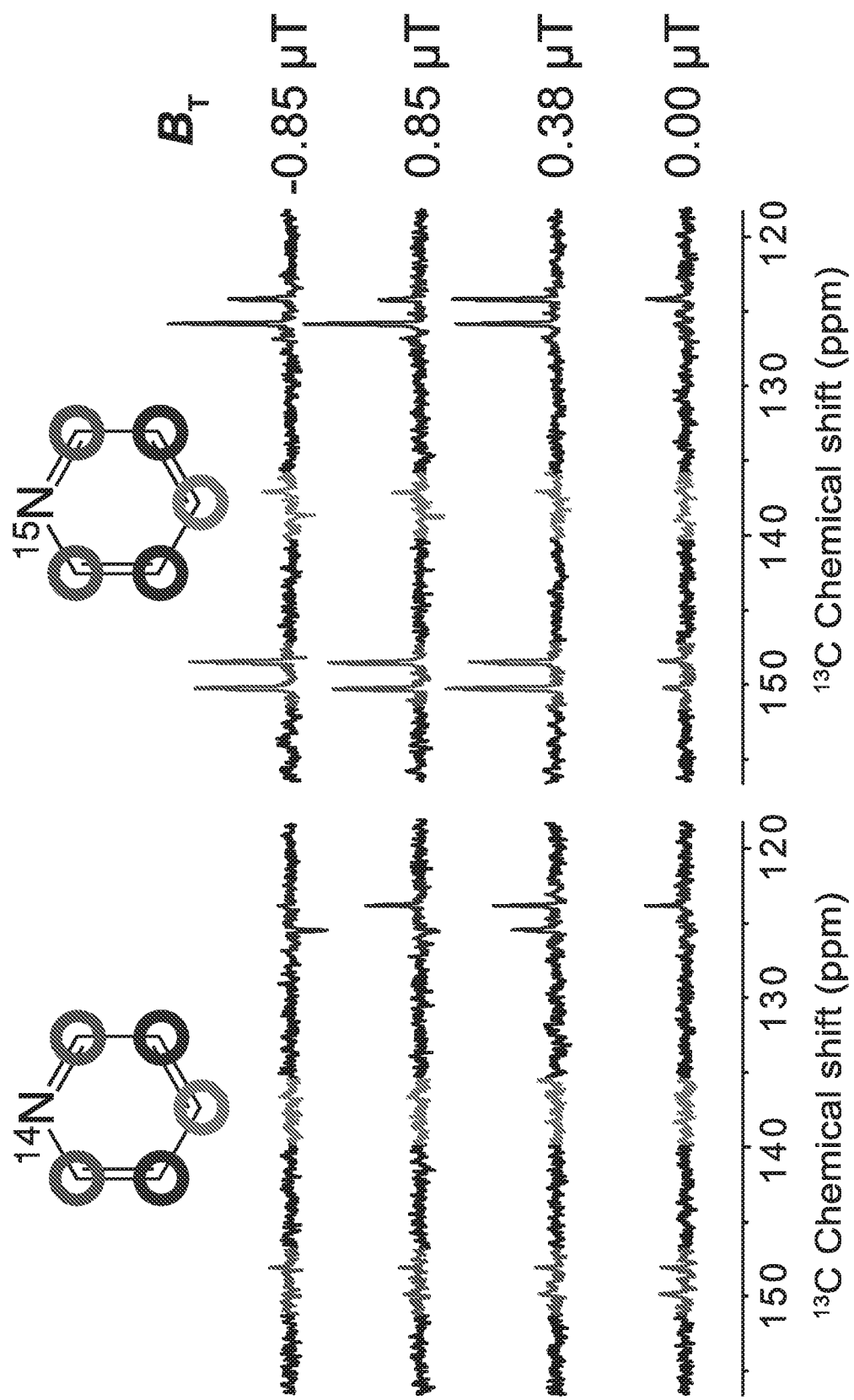
FIG. 3: Proton-coupled $^{13}C$ NMR spectra of SABRE-SHEATH hyperpolarized Py samples with Py-$^{14}N$ and Py-$^{15}N$ at various static transfer magnetic fields.

Finally, and most importantly, it was found that the efficiency of $^{13}$C SABRE-SHEATH hyperpolarization is heavily modulated by the presence of $^{15}$N versus $^{14}$N nuclei at the nitrogen sites. FIG. 3 clearly demonstrates that the presence of a quadrupolar nucleus $^{14}$N (with as opposed to the spin I=½ $^{15}$N nucleus) leads to significantly reduced efficiency of $^{13}$C SABRE-SHEATH. We note that the simple tuning of the micro-Tesla field could not improve the lost efficiency of SABRE-SHEATH hyperpolarization when $^{14}$N is present (FIG. 3). Moreover, the intensity of the HP $^{13}$C NMR signal in ortho-positions is reduced the most. Since the ortho-position is the nearest to the N atom, we conclude that the quadrupolar $^{14}$N relaxation effectively acts as an efficient hyperpolarization sink in case of molecules containing $^{14}$N nuclei. We point out that this efficient quadrupolar relaxation, i.e., scalar relaxation of the second kind, is likely limited to the micro-Tesla hyperpolarization regime, because the corresponding efforts to perform $^{13}$C SABRE in the milli-Tesla regime using Py-$^{15}$N and Py-$^{14}$N (natural abundance material) do not exhibit a disproportionate $P_{13C}$ drop for ortho-carbon position compared to the that of para- and meta-carbon positions. However, $^{13}$C SABRE hyperpolarization in milli-Tesla range is less efficient than SABRE-SHEATH in the micro-Tesla regime, and the produced HP $^{13}$C resonances are anti-phase—a feature that is disadvantageous in the context of most imaging applications. These conclusions are further substantiated by the additional series of experiments performed using acetonitrile-1-$^{13}$C,$^{14}$N and acetonitrile-1-$^{13}$C,$^{15}$N as SABRE substrates (SI). These experiments show the same trends: (i) significantly lower $P_{13C}$ when $^{14}$N-labeled substrate is employed (FIG. 4), and (ii) when $^{13}$C sites have longer Ti, $P_{13C}$ can be significantly increased. Specifically, FIG. 4 shows a spectrum of $^{13}$C hyperpolarized acetonitrile-1-$^{13}$C,$^{15}$N with $P_{13C}$ 4.8% using 50% p-H$_2$. If near 100% p-H$_2$ is employed, the polarization yields could be effectively tripled to $P_{13C}$~14.4%.

Although we have previously reported $^{13}$C SABRE-SHEATH hyperpolarization, the pioneering work yielded very low $^{13}$C signal enhancement (<100 at 9.4 T) and $P_{13C}$ (<0.1%) compared to those reported here for the following reasons: (i) hyperpolarization at sub-optimal µT field (FIG. 2G), (ii) non-optimized temperature, (iii) the use of very high (and sub-optimal) substrate and catalyst concentrations.

To summarize, efficient $^{13}$C hyperpolarization using SABRE-SHEATH is described herein, which relies on p-H$_2$ in chemical exchange as the source of spin order. $P_{13C}$ values of up to ~1.5% are produced in seconds, and significantly greater $P_{13C}$ can be potentially obtained for $^{13}$C sites with greater Ti values (typically the case for $^{13}$C sites without directly attached protons). The presence of spin-½ $^{15}$N nuclei (to eliminate $^{13}$C polarization losses due to efficient $^{14}$N quadrupolar relaxation of the second kind) is required for efficient $^{13}$C hyperpolarization for Py. Recent demonstrations of heterogeneous and aqueous SABRE hyperpolarization are highly synergistic with the results reported here, as they potentially pave the way to ultra-fast production of pure and aqueous HP $^{13}$C contrast agents for biomedical use.

Ir-IMes catalyst was synthesized as previously described. Pyridine-$^{15}$N (Py-$^{15}$N) (Sigma-Aldrich-Isotec, 486183) was used as received to prepare a series of Py-$^{15}$N solutions (or Py-$^{14}$N for control experiments) in CD$_3$OD. An initial solution containing ~100 mM substrate and ~5 mM catalyst precursor was used for magnetic field and temperature studies (FIGS. 2F and 2G) as well as for a comparison of Py-$^{15}$N with Py-$^{14}$N (FIG. 3). Otherwise, a diluted solution containing 5 mM substrate and 0.25 mM catalyst was used.

The details of the experimental setup and catalyst activation protocols have been previously described in great detail. P-H$_2$ with ~80% para-fraction was produced using a home-built p-H$_2$ generator, and ~7 atm p-H$_2$ pressure was employed for the $^{13}$C SABRE-SHEATH experiments. A 9.4 T Bruker Avance III NMR spectrometer was used for all NMR spectra acquisitions. The values for $^{13}$C signal enhancement and $P_{13C}$ were calculated by comparison of HP signals of Py and a thermally polarized NMR signal reference from the solvent.

Experimental Procedures

To an Eppendorf safe-lock tube, pyridine-$^{15}$N (or pyridine-$^{14}$N) (0.10 M final concentration) and non-activated iridium catalyst ([IrCl(COD)(IMes)], 0.005 M final concentration) and methanol-d$_4$ were added. The tube with stock solution was flushed with Argon and vortexed. In order to achieve lower tracer and catalyst concentration, a part of the stock solution was transferred via Ranin XLS pipet to another Argon-flushed Eppendorf safe-lock tube and methanol-d$_4$ was added. Two subsequent dilutions were performed, respectively resulting in a solution with 5 times lower concentrations (20 mM substrate and 1 mM catalyst) and 20 times lower concentrations (5 mM substrate and 0.25 mM catalyst) compared to those of the initial solution.

The stock solution was transferred via a Ranin XLS pipet into an Argon-filled medium-walled NMR sample tube (5 mm medium wall precision, 3.43 mm ID, 9 in. long, Wilmad Glass, P/N 503-PS-9) equipped with the Teflon tube extension (0.25 in. OD, 3⁄16 in. ID), which was approximately 7 cm long. The tube was attached to the previously described setup through a Wye push-to-connect adapter. The SABRE sample was activated by bubbling parahydrogen at 20 sccm for ~30 min, slowly building the pressure from 1 atm to ~7 atm of parahydrogen (~50% para-fraction or ~80% para-fraction). The parahydrogen flow rate was controlled by a mass flow controller (Sierra Instruments, Monterey, Calif., model number C100L-DD-OV1-SV1-PV2-V1-S0-C0).

The SABRE-SHEATH hyperpolarization procedure was conducted similarly to that described earlier. The sample solution was bubbled with parahydrogen (~50% or 80% para-fraction) at 90 sccm for ~30 s, at ~7 atm inside the magnetic shield. The Earth's magnetic field was attenuated using a three-layered mu-metal shield (6 in. ID & 15 in. in length, part number ZG-206, Magnetic Shield Corp., Bensenville, Ill.), which was degaussed before use. The magnetic field was created using a custom-built solenoid coil and a power supply (GPRS series, GW INSTEK). After stopping parahydrogen bubbling the sample was quickly transferred from the shield to the Earth's magnetic field followed by sample insertion in the bore of 9.4 T magnet and acquisition of the proton-decoupled $^{13}$C NMR spectrum. Typical sample transfer time (from cessation of p-H$_2$ gas to $^{13}$C detection in 9.4 T magnet) was approximately 6 seconds. The $^{13}$C NMR peaks' integrals were normalized with respect to a $^{13}$C NMR signal of the solvent CD$_3$OD.

$^{13}$C SABRE-SHEATH Enhancement Factor Calculation

The $^{13}$C SABRE-SHEATH signal enhancement for the data in FIG. 2A was calculated by comparing the integral signal intensities of the corresponding $^{13}$C NMR peaks of the spectra of the hyperpolarized sample with the thermally polarized $^{13}$C NMR peak of the solvent (CD$_3$OD). The $^{13}$C SABRE-SHEATH enhancement was calculated by comparing the integrated signal intensity of the hyperpolarized NMR peak of the $^{13}$C site in the ortho-position obtained from the hyperpolarized sample in a 5-mm medium-walled NMR tube at 5 mM concentration of pyridine-$^{15}$N, and referencing it to the $^{13}$C NMR signal from a thermally polarized solvent, $CD_3OD$ (~24.6 M). The following formula was used for calculation of $^{13}C$ signal enhancements:

$$\varepsilon = (S_{HP}/S_{REF}) \times ([REF]/[HP]),$$

where $S_{HP}$ is the absolute integral calculated for the hyperpolarized signal, $S_{REF}$ is the corresponding integrated signal from the reference compound, and [REF] and [HP] are respectively the concentrations of the reference (~24.6 M) and hyperpolarized (0.005 M) samples (taking into account the $^{13}C$ natural abundance factor). For the data presented in FIG. 2B, the $^{13}C$ signal enhancement was calculated as follows (where 2 is the number of equivalent carbons for ortho-position of pyridine):

$$\varepsilon = (0.77)/(1) \times (24.62/(2 \times 0.005)) \sim 1,900.$$

The $^{13}C$ polarization percentage (% P) was calculated as follows (where % $P_{thermal} = 8.1 \times 10^{-4}$% is the equilibrium thermal $^{13}C$ polarization at room temperature and 9.4 TP:

$$\% P = \varepsilon \times \% P_{thermal} = 1,900 \times 8.1 \times 10^{-4}\% \approx 1.5\%$$

$^{13}C$ spin-lattice relaxation exponential decay constant of $^{15}N$- and $^{14}N$-Py forms

TABLE 1

$^{13}C$ $T_1$ relaxation time constants measured at 9.4 T using an inversion-recovery sequence for 300 mM substrate solutions in $CD_3OD$ (in the absence of SABRE catalyst).

| $^{13}C$ site position | Pyridine-$^{15}N$ | Pyridine-$^{14}N$ |
|---|---|---|
| Ortho | 14.4 ± 0.5 s | 10.2 ± 0.6 s |
| Meta | 13.2 ± 0.4 s | 11.5 ± 0.5 s |
| Para | 5.8 ± 0.8 s | 5.4 ± 0.9 s |

Figure 2C:
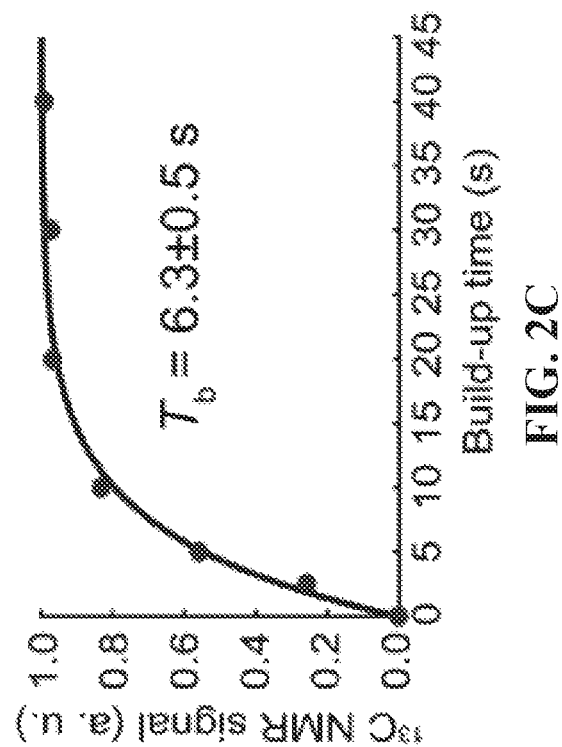
FIG. 2C: $^{13}C$ signal build-up curve at ~0.4 µT showing the BC NMR signal dependence on the p-$H_2$ bubbling time.
Figure 2B:
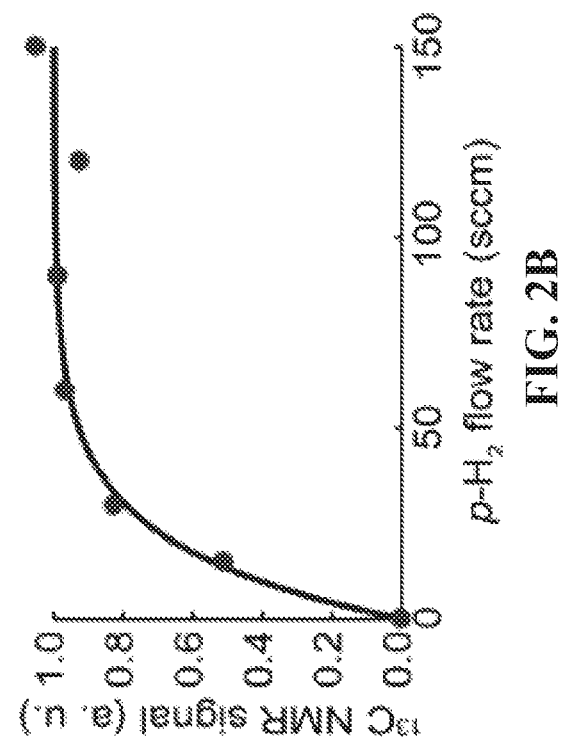
FIG. 2B: $^{13}C$ NMR signal dependence as a function of p-$H_2$ flow rate using a constant duration of p-$H_2$ bubbling of 30 s.
Figure 2E:
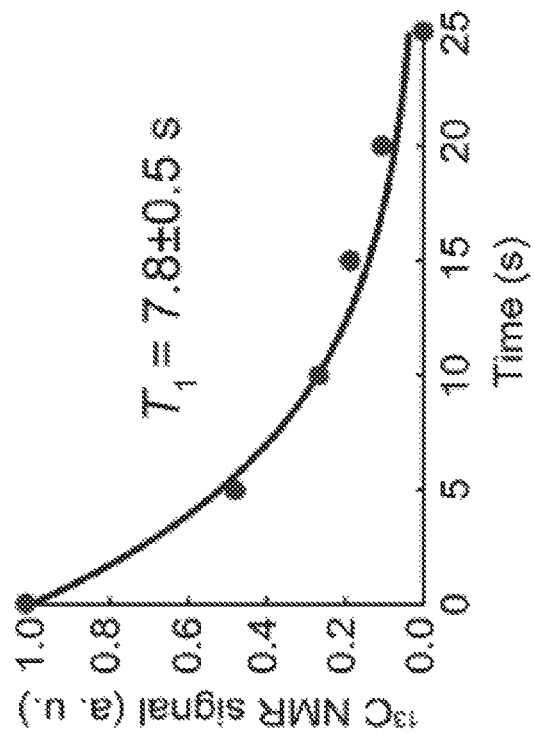
FIG. 2E: HP $^{13}C$ Ti relaxation measurement at high magnetic field (9.4 T) (see SI for details)
Figure 2D:
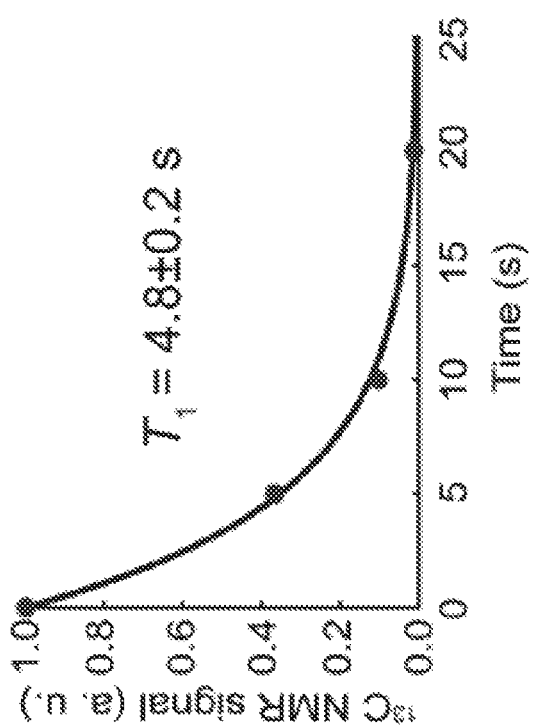
FIG. 2D: HP $^{13}C$ $T_1$ relaxation measurement in the Earth's magnetic field (see SI for details).
Figure 2G:
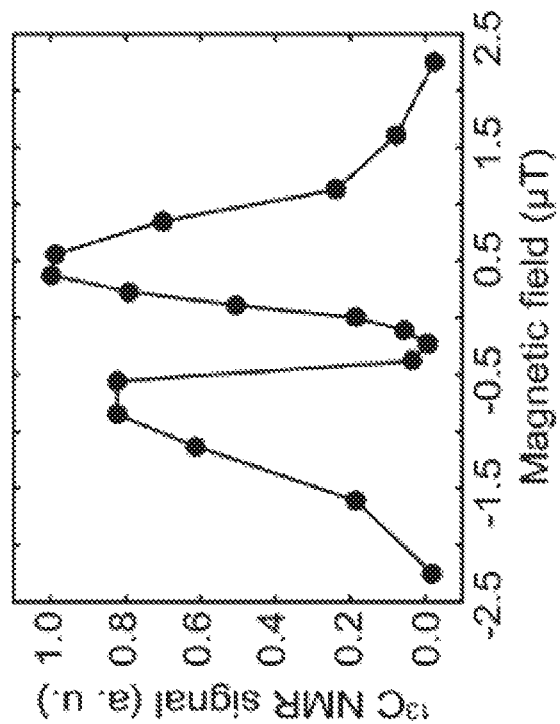
FIG. 2G: Magnetic field dependence of the $^{13}C$ SABRE-SHEATH NMR signal (note that absorptive $^{13}C$ signals are observed in all cases).
Figure 2F:
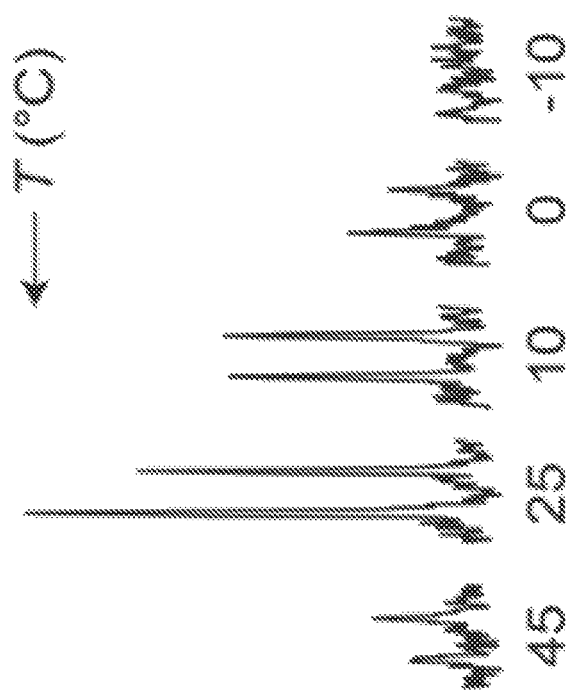
FIG. 2F: Temperature dependence of the proton-coupled $^{13}C$ SABRE-SHEATH NMR signal of ortho-$^{13}C$ spins of Py-$^{15}N$.

Hyperpolarized $^{13}C$ NMR Signal Build-Up and Decay Measurements $^{13}C$ NMR signal build-up curve (FIG. 2C) was measured by varying p-$H_2$ bubbling time through the NMR tube containing catalyst and substrate solution in the magnetic shield. The signal was recorded in 9.4 T NMR spectrometer for each experiment (for each timing of hyperpolarization) corresponding to an individual data point. Following a time period of hyperpolarization, p-$H_2$ flow was ceased, the sample was quickly removed from the magnetic shield chamber and inserted inside 9.4 T NMR spectrometer for $^{13}C$ detection using ~90-degree excitation pulse.

Earth's field $T_1$ of $^{13}C$ nuclei of pyridine-$^{15}N$ (FIG. 2D) was measured using the following procedure. p-$H_2$ was bubbled through the solution in the magnetic shield for 30 s. Then the flow rate was stopped and the NMR tube was stored for a varied amount of time in the Earth's field. Then the sample was quickly (~5 s) transferred to the high magnetic field (9.4 T) for a $^{13}C$ signal detection. One data point was acquired for each experiment, and the data was plotted as a $^{13}C$ signal dependence on the decay delay at the Earth's magnetic field.

$^{13}C$ Ti at high field, 9.4 T (FIG. 2E), was measured on a single HP sample, by using a series of $^{13}C$ NMR acquisitions employing a small angle (~10°) excitation RF pulses after polarization build-up and sample transfer to the high field (9.4 T).

Additional SABRE-SHEATH experiments with acetonitrile-1-$^{13}C$,$^{14}N$ and acetonitrile-1-$^{13}C$,$^{15}N$.

Figure 4B:
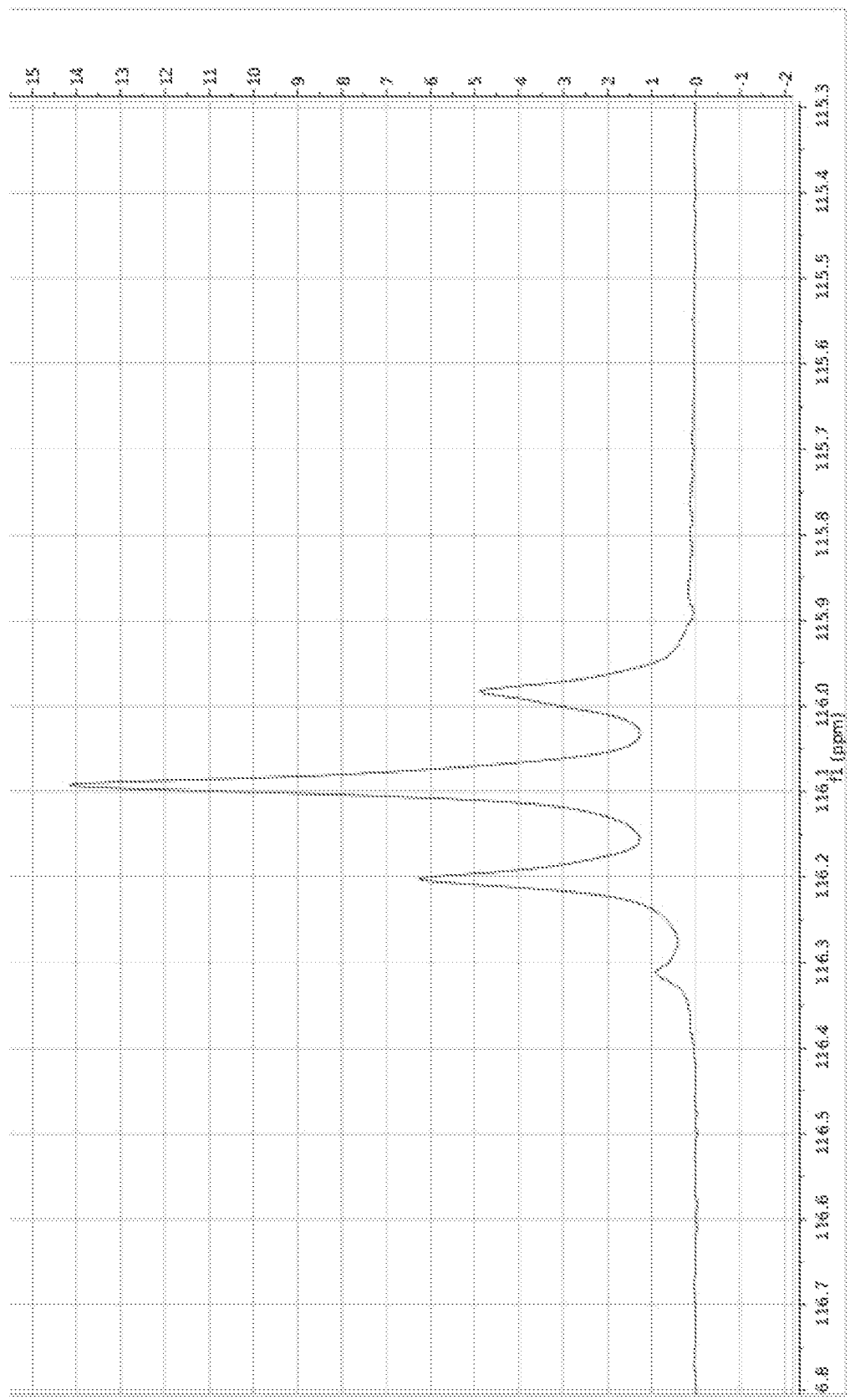
Figure 5A:
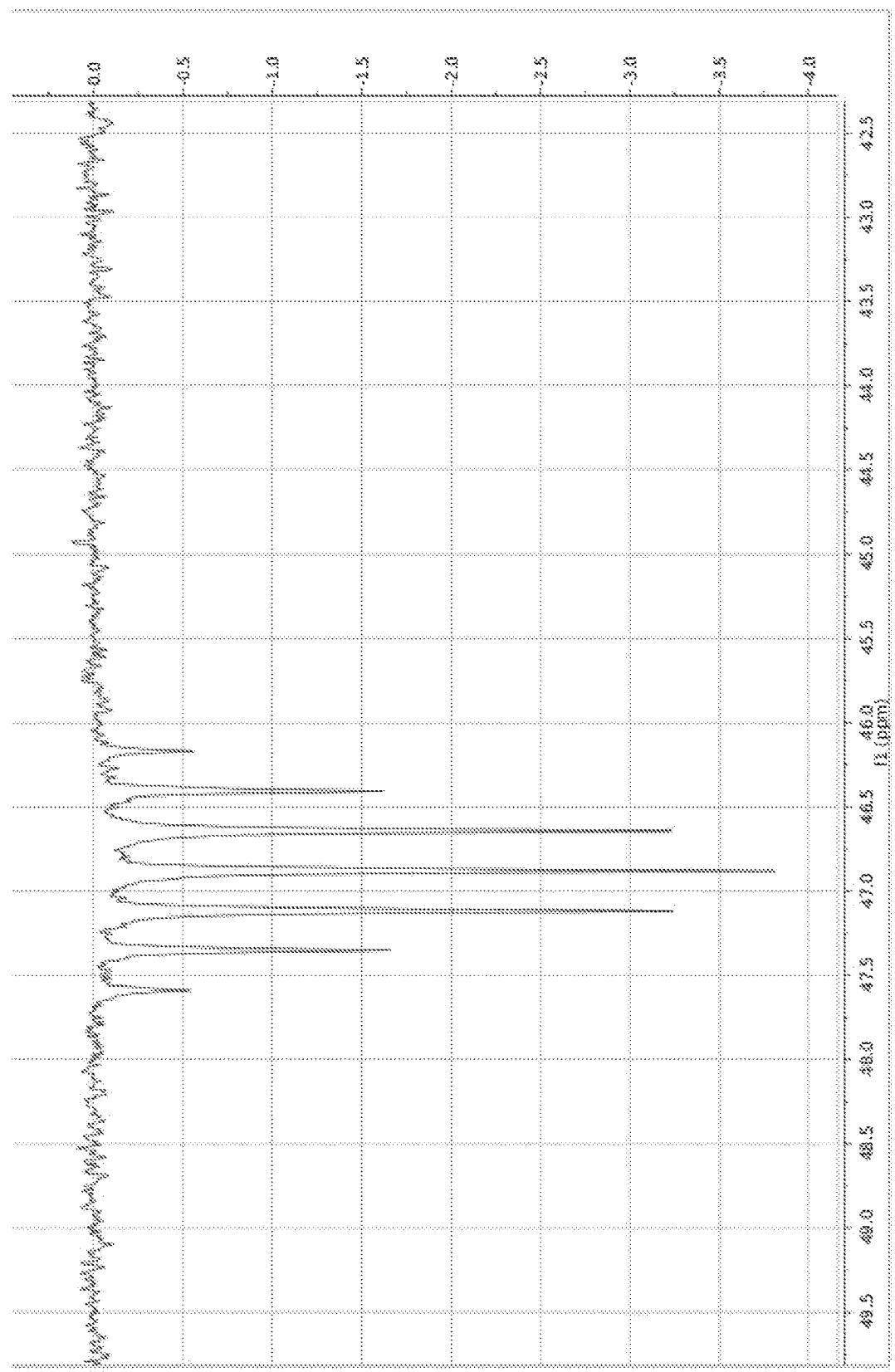
FIG. 5A: $^{13}$C NMR spectrum of signal reference sample (neat CD$_3$OD) recorded at 8.45 T, 8 scans, thermally polarized sample.
Figure 5B:
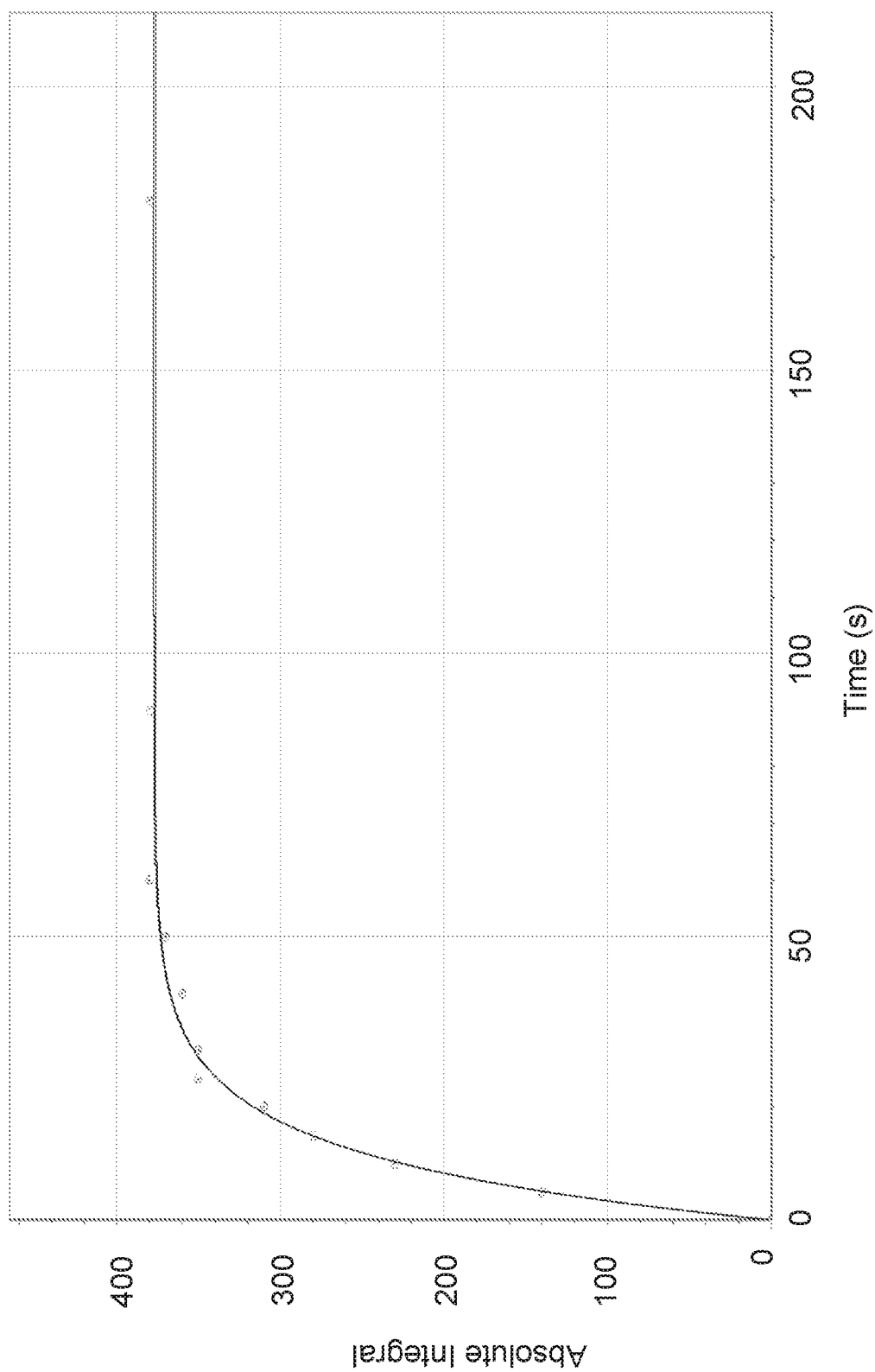
FIG. 5B: $^{13}$C SABRE-SHEATH hyperpolarization build-up of acetonitrile-1-$^{13}$C,$^{15}$N (sample composition 0.05 mM catalyst, 12 mM pyridine, 4 mM acetonitrile-$^{13}$C,$^{15}$N; pyridine used as a co-substrate) at ~0.74 µT static magnetic field. The effective build-up constant is ~11 s.

SABRE-SHEATH experiments performed with acetonitrile-1-$^{13}C$,$^{14}N$ and acetonitrile-1-$^{13}C$,$^{15}N$ showed the same trends as experiments with pyridine-$^{14}N$ and pyridine-$^{15}N$. Namely, signal enhancement was significantly higher for doubly labeled substrate acetonitrile-1-$^{13}C$,$^{15}N$ ($\varepsilon$~230) than that for acetonitrile-$^{13}C$,$^{14}N$ ($\varepsilon$~20), see FIG. 4A, when using 50% parahydrogen. Furthermore, a subsequent dilution and optimization of the sample composition allowed us to achieve much higher $^{13}C$ NMR signal enhancements (4-6,700, corresponding to $P_{13C}$ of ~4.8% when using 50% parahydrogen), see FIG. 4B. This is mostly due to longer $^{13}C$ relaxation time at micro-Tesla magnetic field corresponding to the signal build-up time of ~11 s (measured using the same experimental protocol as described in chapter 4 at ~0.74 μT, FIG. 5). $T_1$ of $^{13}C$ site in acetonitrile-1-$^{13}C$,$^{15}N$ is ~39 s at 8.45 T (vs. $^{13}C$ $T_1$ of ~14 s in pyridine-$^{15N}$ at similar magnetic field of 9.4 T), which is also in line with much higher signal enhancements obtained for acetonitrile compared to those for pyridine (FIG. 4B). The $T_1$ of $^{15}N$ site in acetonitrile-1-$^{13}C$,$^{15}N$ is 97 s.

Example 2 Toward Hyperpolarized $^{19}F$ Molecular Imaging Via Reversible Exchange with Parahydrogen Fluorine-19 has high NMR detection sensitivity—similar to that of protons, owing to its large gyromagnetic ratio and high natural abundance (100%). Unlike protons, however, fluorine-19 ($^{19}F$) has a negligible occurrence in biological objects, as well as a more sensitive chemical shift. As a result, in vivo $^{19}F$ NMR spectroscopy and MR imaging offer advantages of negligible background signal and sensitive reporting of the local molecular environment. In some embodiments, disclosed herein is NMR hyperpolarization of $^{19}F$ nuclei using reversible exchange reactions with parahydrogen gas as the source of nuclear spin order. NMR signals of 3-fluoropyridine were enhanced by ~100 fold, corresponding to 0.3% $^{19}F$ nuclear spin polarization (at 9.4 T) using ca. 50% parahydrogen. While future optimization efforts will likely significantly increase the hyperpolarization levels, the utility of $^{19}F$ hyperpolarization for high-resolution hyperpolarized $^{19}F$ imaging and hyperpolarized $^{19}F$ pH sensing is already demonstrated.

The $^{19}F$ nucleus has a gyromagnetic ratio of 94% of that of proton, and a natural abundance of 100%. As a result, $^{19}F$ NMR has a detection sensitivity that is comparable to that of protons, which is the highest among stable isotopes. However, $^{19}F$ has almost no biological occurrence, giving rise to negligible background MR signal. Moreover, the $^{19}F$ chemical shift can be exquisitely sensitive to the local molecular environment, and unlike the case for low-frequency heteronuclei, it can be relatively easy to adapt clinical scanners for $^{19}F$ detection in commercial MR scanners. The use of $^{19}F$ exogenous contrast agents has recently fueled the development of a wide range of biomedical applications, including inhalable perfluorinated carbon compounds for pulmonary imaging, perfluoropolyether for stem cell tracking, and others. $^{19}F$ detection of thermally spin-polarized contrast agents at millimolar levels is feasible. These detection limits can be further reduced by 3 to 5 orders of magnitude using hyperpolarization. Biomedical applications of HP contrast agents and their potential to revolutionize molecular imaging are the primary drivers of the hyperpolarization technique development. So far, most approaches have focused on hyperpolarization of low-gamma nuclei (e.g., $^{13}C$, $^{129}Xe$, $^{15}N$, etc.). These hyperpolarized (HP) compounds can be used to probe metabolism (e.g. elevated lactate metabolism in cancer using HP $^{13}C$-pyruvate, pH, etc.), function (e.g. lung ventilation and diffusion), and others.

Hyperpolarization of high-gamma nuclei including $^{1}H$ and $^{19}F$ has seen a modest interest in the context of biomedical MR applications, because fluorine and proton sites frequently have short spin-lattice relaxation times ($T_1$) and correspondingly short lifetimes of the HP state. $^{19}F$ nuclei (with $T_1$~4.2 s-4.6 s) of perfluorinated compounds were hyperpolarized by parahydrogen induced polarization technique by Plaumann and co-workers. However, recent developments in the field of long-lived spin states have the potential to significantly extend the lifetime of HP states in general—including HP states of high-gamma nuclei. Therefore, HP fluorine contrast agents may offer the best of many worlds: naturally high detection sensitivity, enhanced with NMR hyperpolarization, potentially enabling highly spectrally-sensitive detection at sub-millimolar range all without interference from background signals.

It was demonstrated that Signal Amplification By Reversible Exchange (SABRE) can be extended to hyperpolarization of heteronuclei (e.g. $^{15}N$) by performing SABRE in micro-Tesla magnetic fields. This was introduced as SABRE in SHield Enables Alignment Transfer to Heteronuclei (SABRE-SHEATH). SABRE-SHEATH has since been applied to a wide range of $^{15}N$ labeled molecules including an array with high biological relevance. The hyperpolarization process is efficient, allowing one to achieve $^{15}N$ polarization ($P_{15N}$) values exceeding 20% in less than a minute. This technique employs chemical exchange of a to-be-hyperpolarized compound and parahydrogen gas (para-$H_2$). In the transient polarization transfer complexes nuclear spin order is transferred spontaneously from para-$H_2$ to spins in the target molecule when the static magnetic field is chosen appropriately. A metal catalyst is used to drive this reversible process. To date, Iridium hexacoordinate complexes with equatorial exchangeable ligands (FIG. 6) are the most efficient SABRE and SABRE-SHEATH catalysts.

In some embodiments, disclosed herein is the hyperpolarization of $^{19}F$, extending SABRE-SHEATH hyperpolarization to other heteronuclei. In addition, the present disclosure demonstrates the feasibility and utility of $^{19}F$ SABRE-SHEATH for molecular imaging as well as $^{19}F$ pH sensing.

Figure 9A:
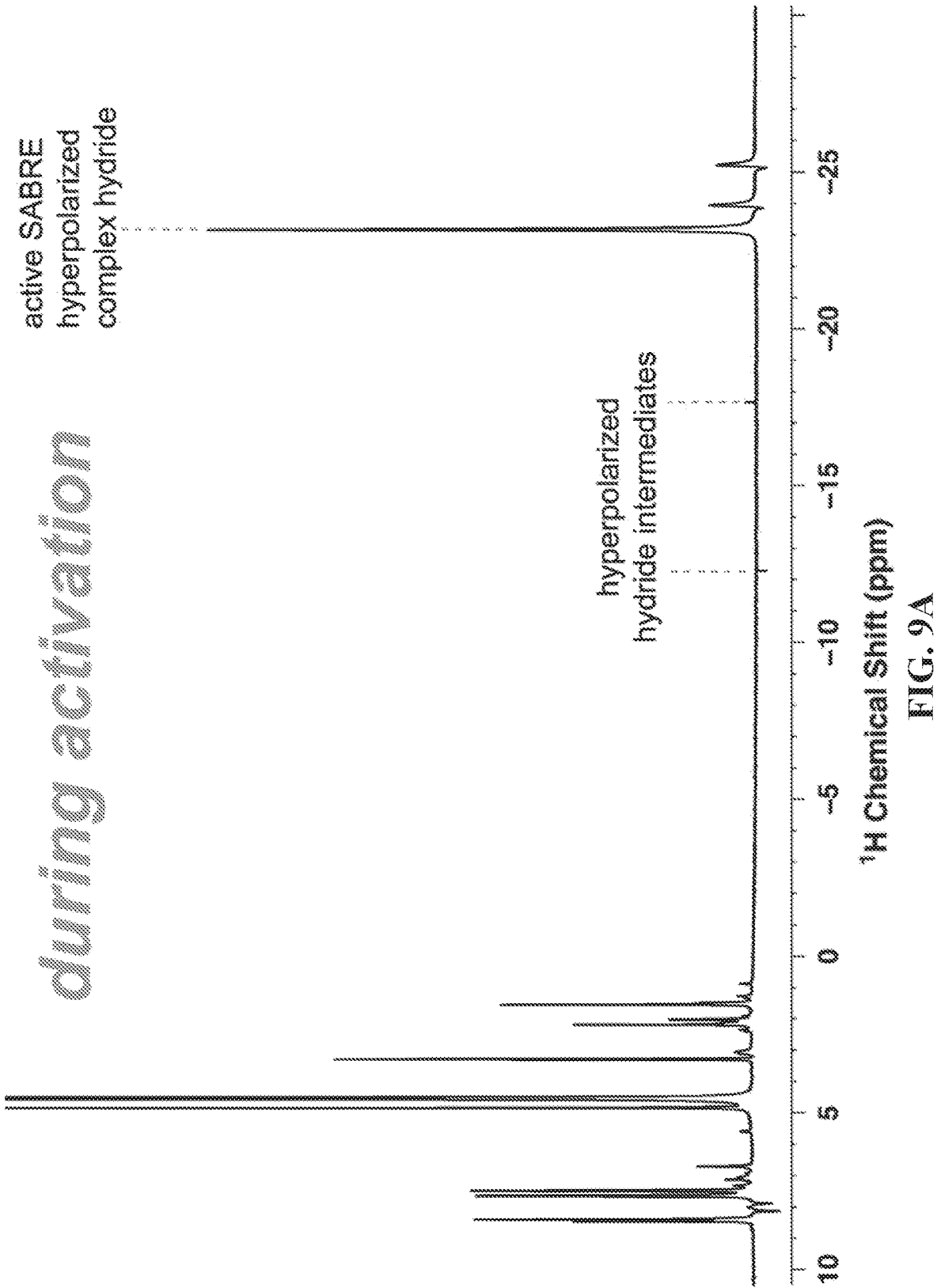
FIGS. 9A and 9B show $^1$H NMR spectra of 3-$^{19}$F-Py during (FIG. 9A) and after (FIG. 9B) SABRE catalyst precursor activation. All spectra were acquired in CD$_3$OD with ~50 sccm parahydrogen flow (~50% para-fraction, ~6 atm) using a 9.4 T high-resolution Bruker Avarice III NMR spectrometer. Note the appearance of characteristic hyperpolarized hydride intermediates at ca. (−)12 ppm and ca. (−)18 ppm. Once the catalyst is fully activated (i.e. converted into the hexacoordinate complex shown in FIG. 6B, the NMR peaks corresponding to intermediates disappear, and only the main hydride peaks ca. (−)23 ppm are present, corresponding to the SABRE-active hyperpolarized hydride resonance lines.
Figure 9B:
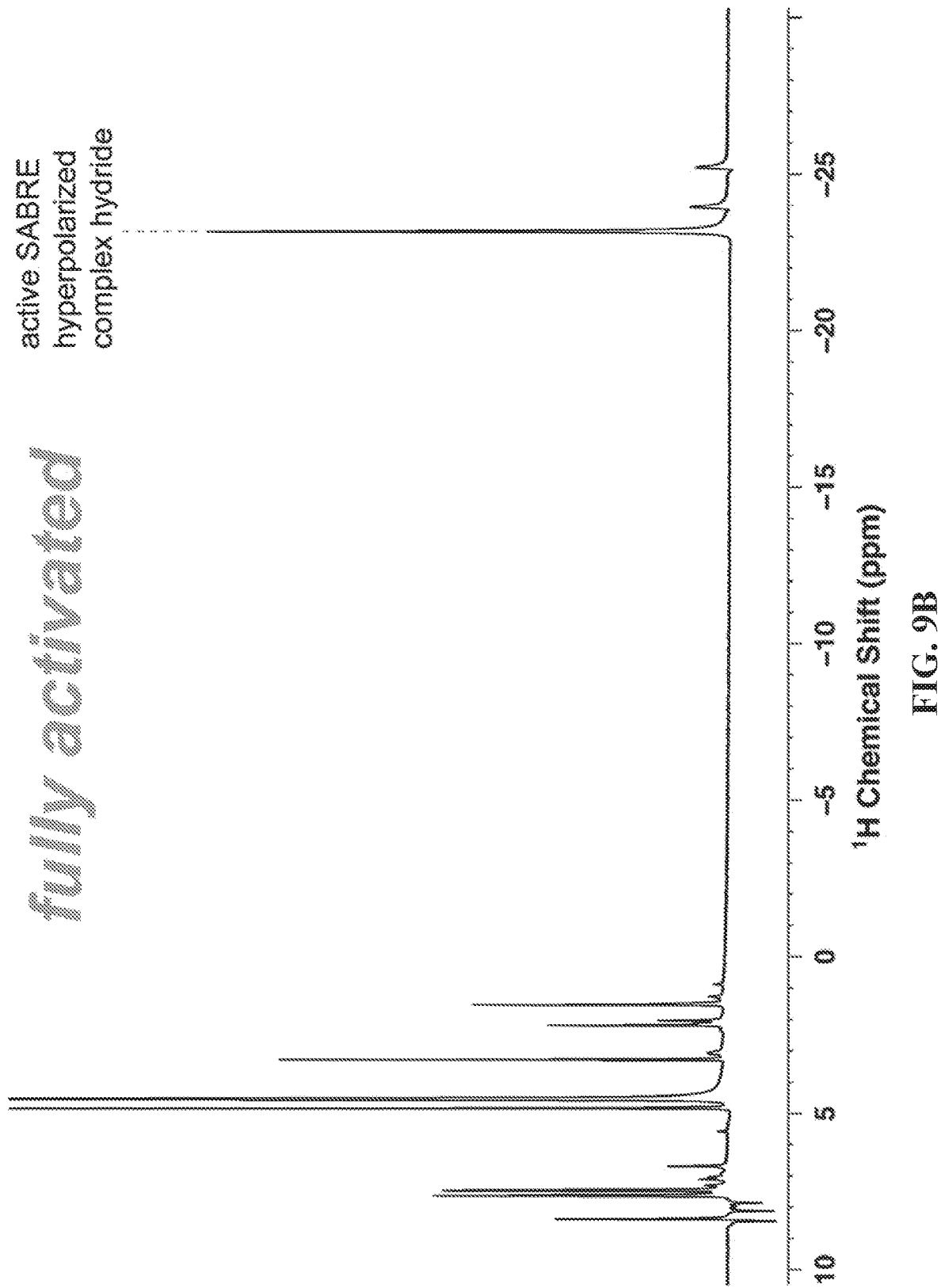
Figure 10:
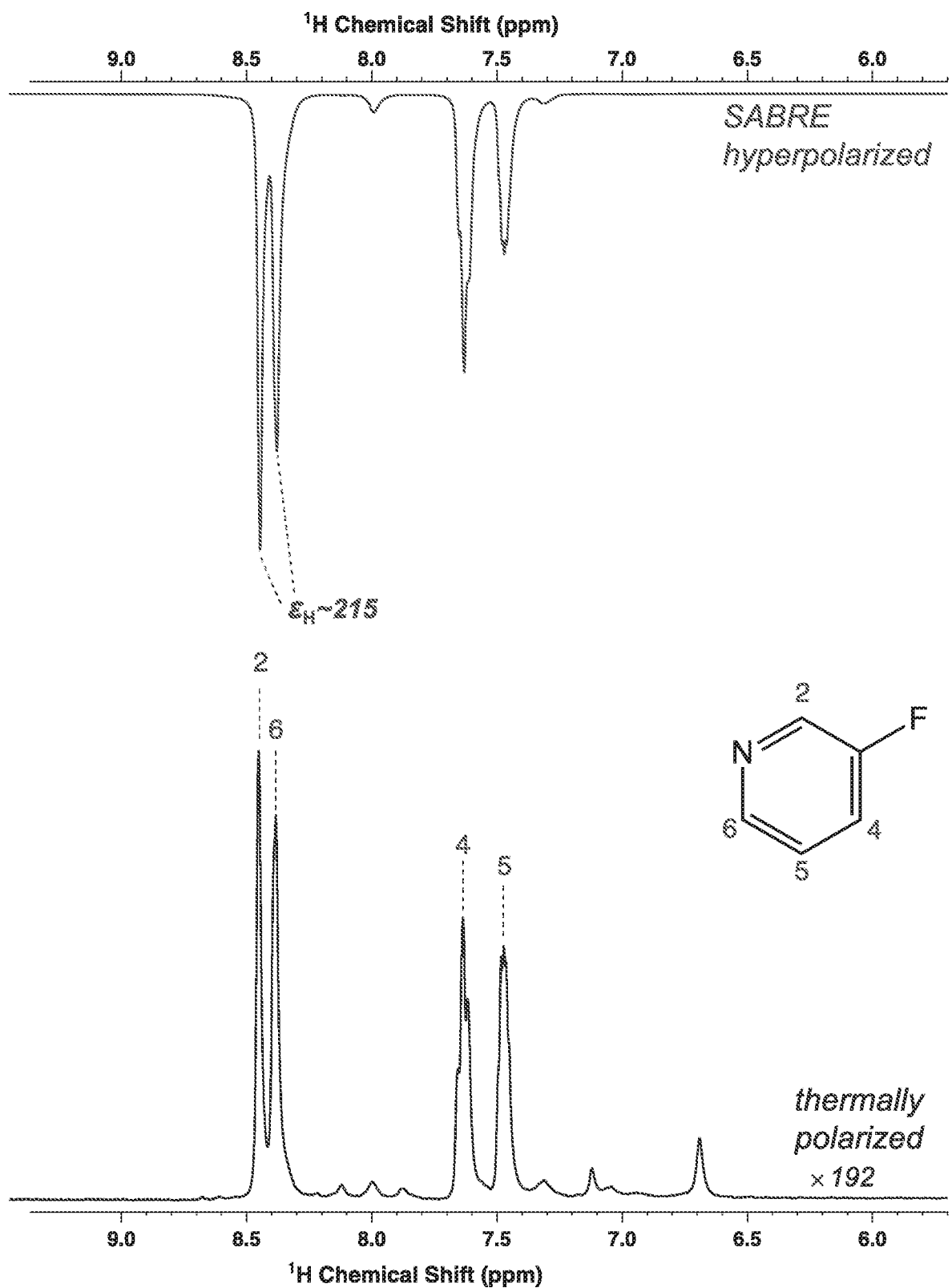
FIG. 10 $^1$H NMR spectra of hyperpolarized (top, red trace) and thermally polarized (bottom, blue trace) 3-$^{19}$F-Py after SABRE catalyst activation. The spectrum of the thermally polarized substrate serves as a signal reference for determining the signal enhancement E. All spectra were acquired in CD$_3$OD with ~100 sccm parahydrogen flow (~50% para-fraction, ~6 atm) using a 9.4 T high-resolution Bruker Avance III NMR spectrometer. For the SABRE hyperpolarized spectrum (top, red trace), the sample was first bubbled at B$_0$ of ~6 mT (magnet fringe field) and then quickly (<4 s) inserted into the bore of the 9.4 T NMR spectrometer for NMR spectrum acquisition.

All experiments were performed using a previously developed SABRE hyperpolarization setup employing a mass-flow-controller (MFC) and medium-wall 5 mm NMR tubes (FIG. 6A) enabling systematic studies at up to 7 atm of para-$H_2$. Samples were prepared with ~5 mM of the pre-activated catalyst [IrCl(cod)(IMes)], where IMes=1,3-bis(2, 4,6-trimethylphenyl)imidazol-2-ylidene; cod=cyclooctadiene] and ~100 mM 3-$^{19}F$-pyridine (3-$^{19}F$-Py) in a $CD_3OD$ solution (~0.6 mL, Isotec-Sigma-Aldrich), FIG. 6. The NMR tube was inserted into ¼ in. OD/³/₁₆ in. ID Teflon tubing, which allowed for convenient connection to a ¼ in. push-to-connect port of the high-pressure setup for para-$H_2$ bubbling via ¹/₁₆ in. OD/¹/₃₂ in. ID tubing inserted all the way to the bottom of the NMR tube. The catalyst activation by para-$H_2$ was monitored by in situ $^1H$ NMR spectroscopy at 400 MHz by detecting the formation of HP intermediate hydride species and the signatures of HP hydride peaks of the hexacoordinate complex shown in FIG. 6B (expected at (−)10-(−)27 ppm range). The corresponding $^1H$ NMR spectra of the activating and fully activated catalyst with this substrate are shown FIGS. 9A and 9B. The formation of this complex was also confirmed by performing SABRE hyperpolarization at ~6 mT, and the maximum signal enhancement CH was found to be ~215-fold, corresponding to $P_H$~0.7% using 50% para-$H_2$ (FIG. 10).

Figure 6A:
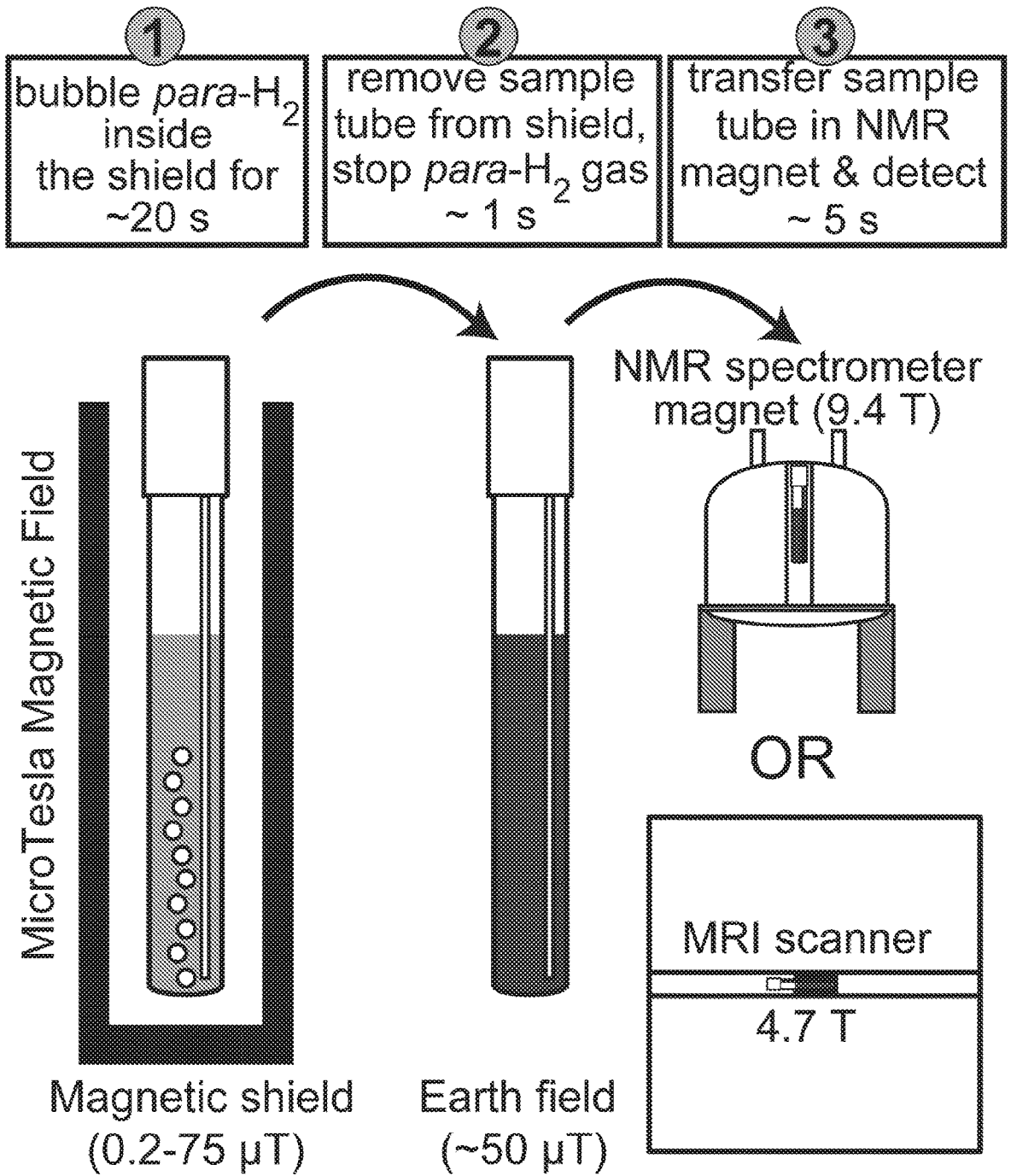
FIG. 6A: Diagram of the $^{19}$F SABRE-SHEATH hyperpolarization process. The solenoid coil inside the mu-metal shield allows creating magnetic fields between 0.2 and 75 µT.
Figure 6B:
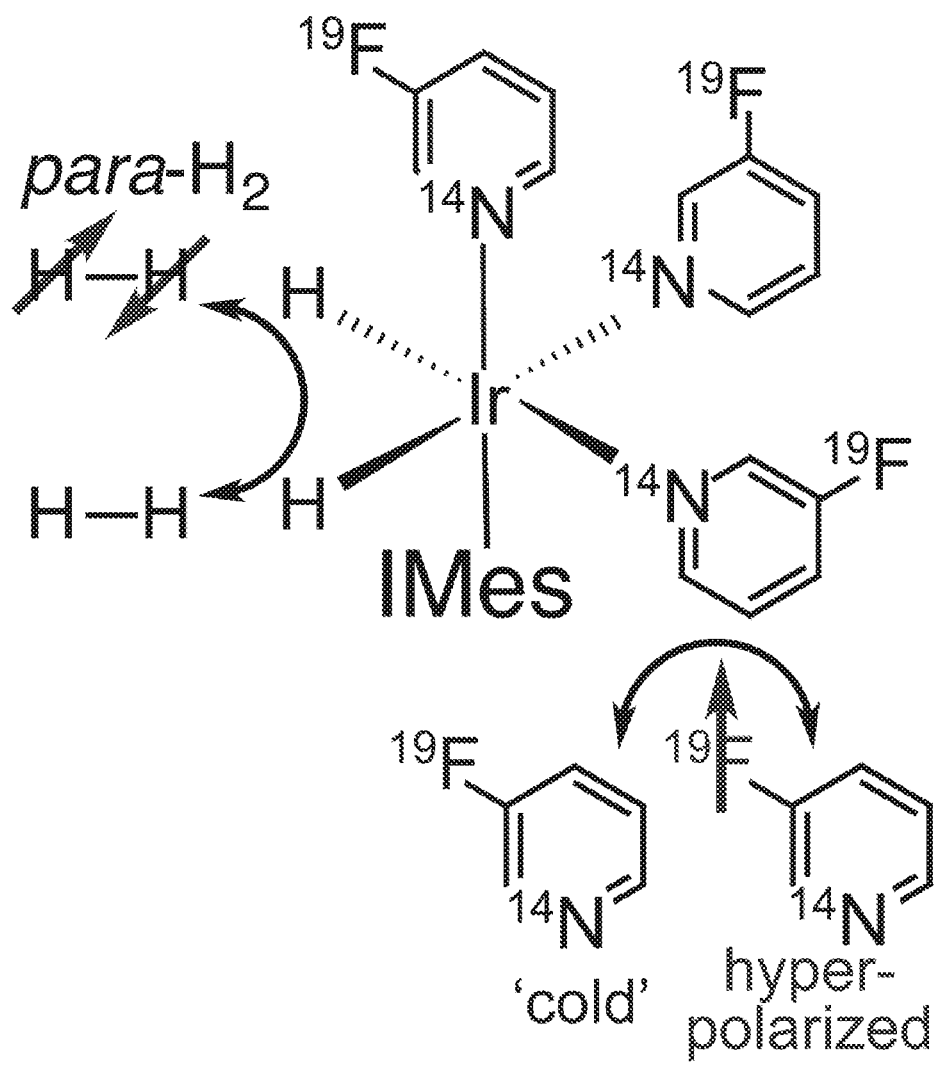
FIG. 6B: diagram showing para-H$_2$ and 3-$^{19}$F-Py exchange between the solvent and the IrIMes hexacoordinate complex, facilitating coherent polarization transfer.
Figure 6C:
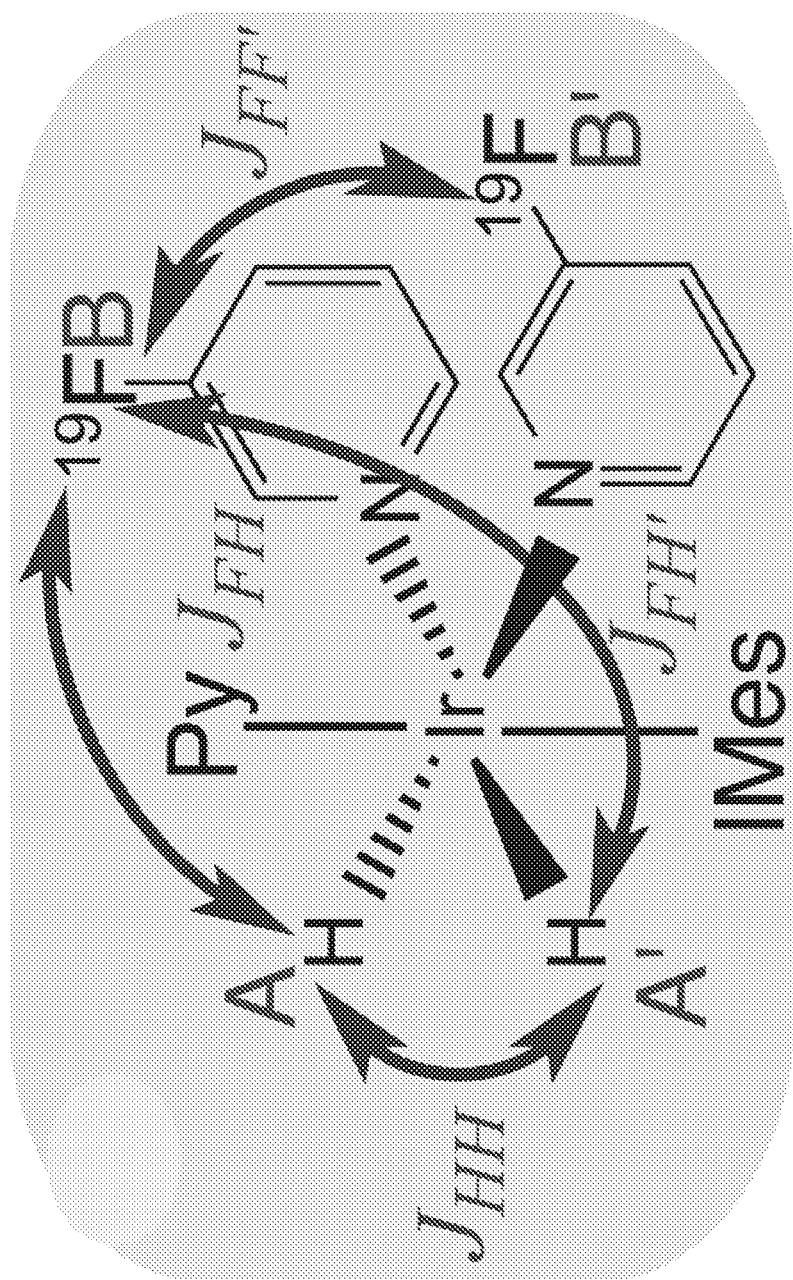
FIG. 6C: the relevant four-spin system (AA'BB') and heteronuclear spin-spin couplings relevant to the SABRE-SHEATH polarization transfer. Axial 3-$^{19}$F-Py spin-spin couplings are neglected because they are significantly weaker.
Figures 7A, 7B:
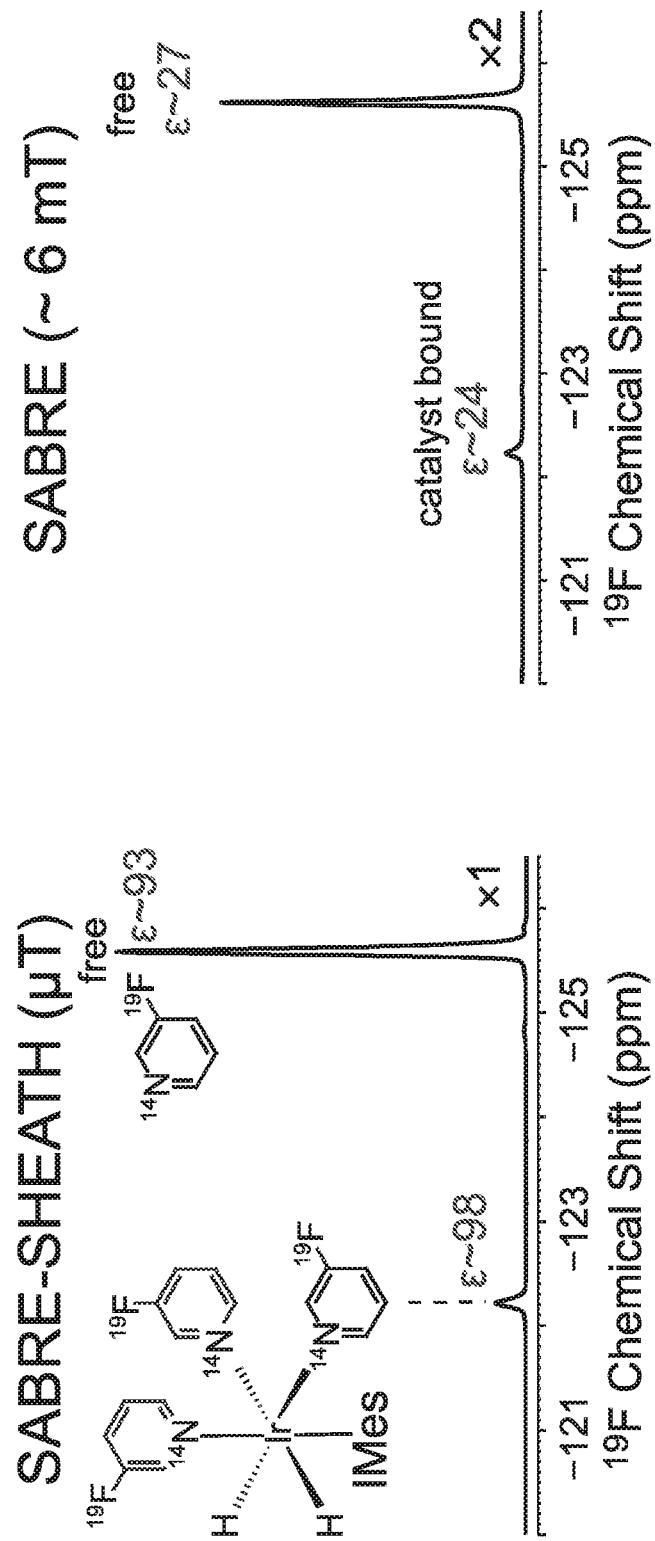
FIG. 7A: $^{19}$F spectrum of ~100 mM hyperpolarized (HP) 3-$^{19}$F-Py produced via SABRE-SHEATH approach at ~5 µT and ~25° C.
FIG. 7B: corresponding $^{19}$F spectrum produced via conventional SABRE at ~6 mT and ~25° C.
Figures 7C, 7D:
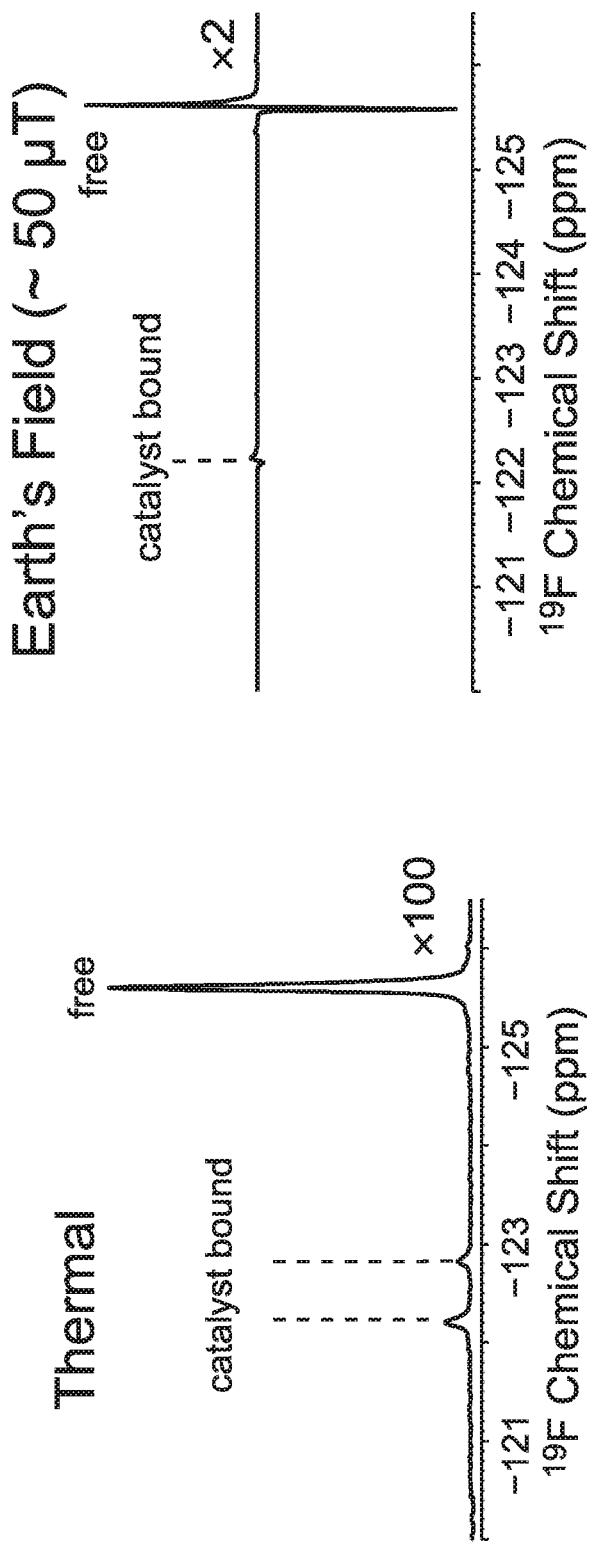
FIG. 7C: corresponding $^{19}$F spectrum obtained with thermally polarized substrate.
FIG. 7D: corresponding $^{19}$F spectrum of 3-$^{19}$F-Py hyperpolarized in the Earth's magnetic field (ca. 50 µT).
Figure 7G:
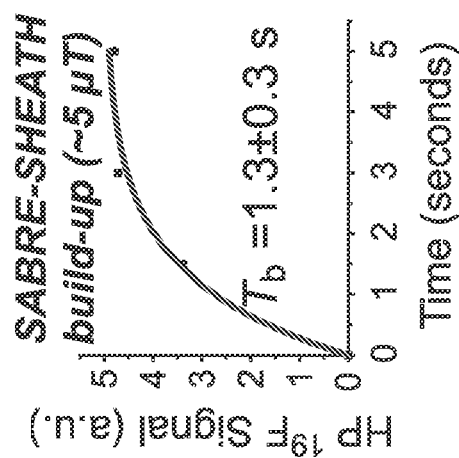
FIG. 7G: Build-up of $^{19}$F polarization at ~5 µT using the SABRE-SHEATH hyperpolarization protocol (FIG. 1).
Figure 7F:
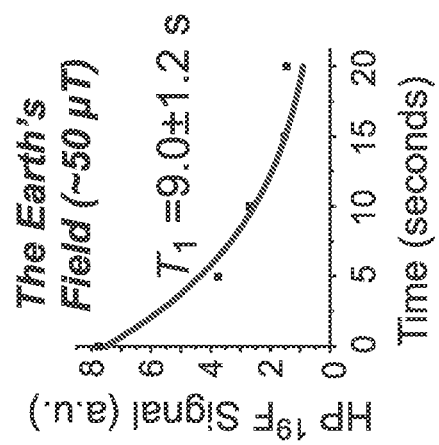
FIG. 7F: corresponding curve reflecting Ti decay of the HP $^{19}$F signal occurring in the Earth's magnetic field (ca. 50 µT).
Figure 7E:
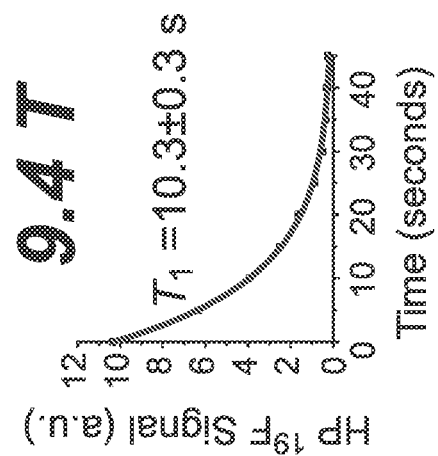
FIG. 7E: Ti decay of HP $^{19}$F signal at 9.4 T.

Once the SABRE catalyst is activated, it forms a hexacoordinate complex corresponding to four-spin system (AA'BB') with heteronuclear spin-spin couplings mediating spontaneous SABRE-SHEATH polarization transfer (FIG. 6). Finally, $^{19}F$ SABRE-SHEATH experiments were performed using a magnetic shield, as outlined in FIG. 6A. FIG. 7A shows a $^{19}F$ NMR spectrum of 3-$^{19}F$-Py hyperpolarized via SABRE-SHEATH. The maximum signal enhancements were $\varepsilon_F$~93-fold and ~98-fold for free and catalyst-bound $^{19}F$ NMR resonances, respectively, corresponding to $^{19}F$ polarization (PF) of ~0.28% using ~50% para-$H_2$. If ~100% para-$H_2$ would be employed the PF would be effectively tripled to ~0.85%. While representing a significant improvement in sensitivity, this number is still several-fold lower than corresponding values achieved via SABRE conducted in the milli-Tesla regime (see above and also previous reports), as well as values previously achieved for $^{15}N$ polarization using the SABRE-SHEATH approach. The likely explanation for this trend is several fold lower $^{19}F$ $T_1$ values at high and low magnetic fields (FIGS. 7E and 7F) under otherwise similar experimental conditions (as will be discussed in greater detail below), which likely resulted in disproportionately greater polarization loss during the ~6 s long sample transfer from the magnetic shield into the 9.4 T NMR spectrometer.

It should be noted that ~(−)122.8 ppm resonance seen in thermal spectrum (FIG. 7C) corresponding to axial 3-$^{19}F$-Py is not significantly hyperpolarized (FIG. 7A), because the corresponding spin-spin coupling between hydride protons and $^{19}F$ are significantly weaker those in equatorial plane.

The $^{19}F$ SABRE-SHEATH build-up time constant Tb (1.3±0.3 s, FIG. 7G) is relatively short compared to Tb of $^1H$ spins in the milli-Tesla regime (21±2 s), likely due to interactions with $^{14}N$ (i.e. within the 3-$^{19}F$-Py framework) acting as an efficient quadrupolar relaxation center in the micro-Tesla regime, i.e., via scalar relaxation of the second kind. Indeed, this explanation is additionally supported by the observing that the SABRE-SHEATH $^{19}F$ signal as a function of the field (FIG. 7H) exhibits no clear maximum compared to the well-defined maximum typically observed in the case of $^{15}N$ SABRE-SHEATH. Moreover, It was recently shown that relaxation problems caused by quadrupolar neighbors could be greatly mitigated for the hyperpolarization of more distant $^{13}C$ spins by replacing $^{14}N$ (I=1) with $^{15}N$ (I=½) in the target substrate—an approach which should improve $^{19}F$ hyperpolarization as well.

Figure 7I:
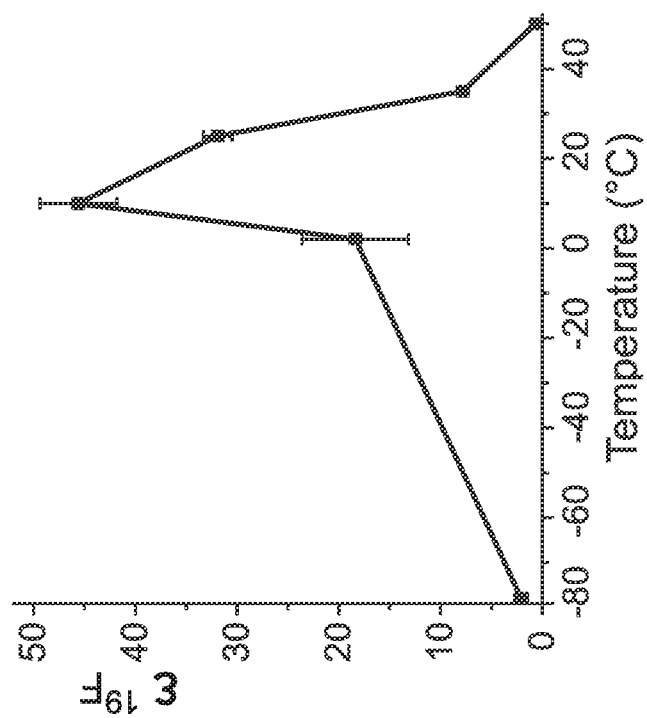
FIG. 7I: $^{19}$F HP signal dependence on temperature during SABRE-SHEATH hyperpolarization at ~5 µT. All spectra are acquired in CD$_3$OD at 9.4 T magnetic field using a Bruker Avance III NMR spectrometer and 50% parahydrogen (para-H$_2$).
Figure 7H:
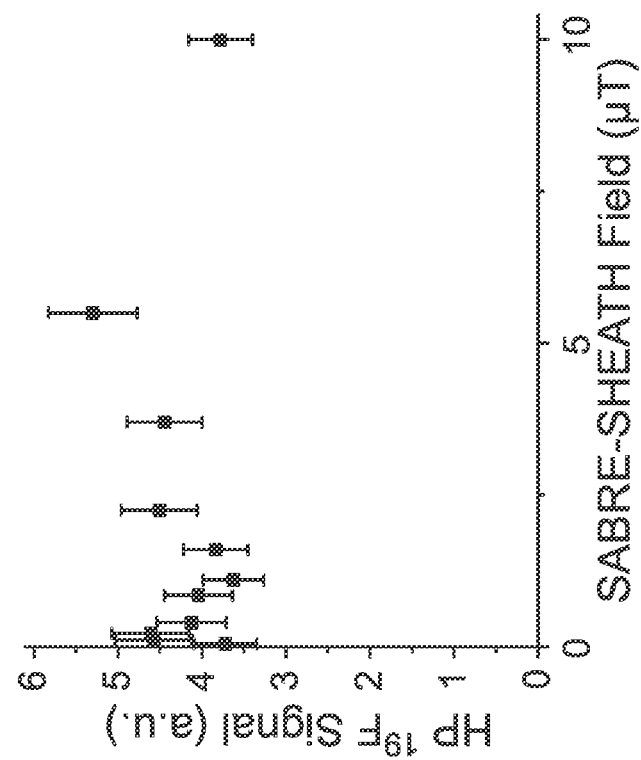
FIG. 7H: $^{19}$F HP signal dependence on magnetic field during SABRE-SHEATH hyperpolarization at ~25° C.

While performing $^{19}F$ SABRE experiments at the Earth's magnetic field (ca. 50-80 μT) yielded expected anti-phase HP lines (FIG. 7D), $^{19}F$ SABRE hyperpolarization in the milli-Tesla range (ca. 6 mT, FIG. 7B) yielded in-phase HP resonances with $\varepsilon_F$~27 fold and $\varepsilon_F$~24 fold for free and catalyst-bound $^{19}F$ NMR resonances, respectively. Not surprisingly, the $^{19}F$ SABRE hyperpolarization efficiency in the milli-Tesla range is significantly lower than that in the micro-Tesla range of SABRE-SHEATH, despite more favorable relaxation properties (e.g. scalar relaxation of the second kind should be suppressed in the milli-Tesla magnetic field regime). Notably, $^{19}F$ HP signals produced in both milli-Tesla and micro-Tesla field regimes are in-phase (i.e. more suitable for MRI), and are absorptive (i.e., they have the same phase as the thermally $^{19}F$ polarized signals, FIG. 7C). Similarly to $^1H$ SABRE and $^{15}N$ SABRE-SHEATH, $^{19}F$ SABRE-SHEATH signals exhibited a clear maximum when measured as a function of temperature (FIG. 7I).

Figure 8B:
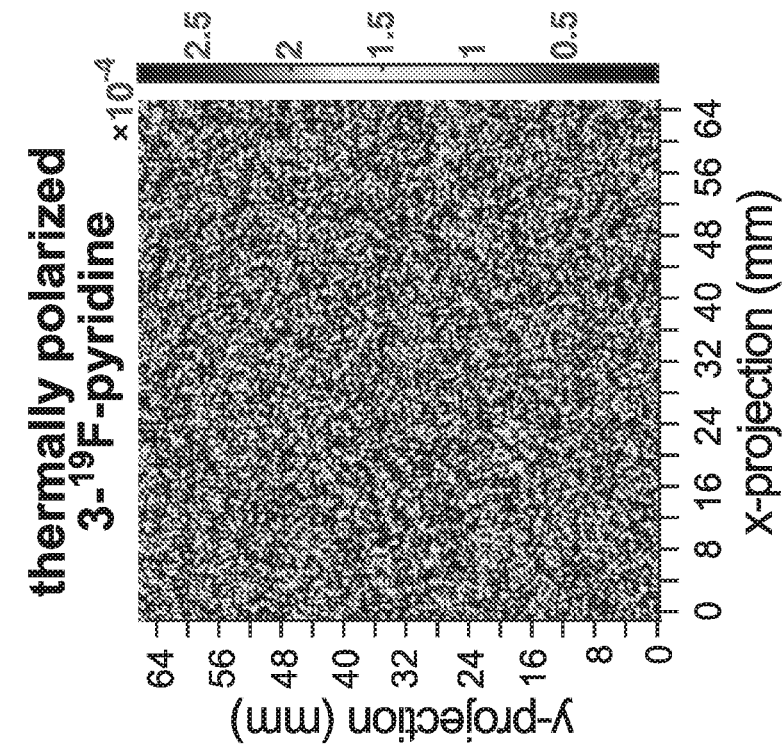
FIGS. 8A-8D show feasibility demonstrations of hyperpolarized $^{19}$F biomedical applications using HP 3-$^{19}$F-Py as a model agent.
Figure 8A:
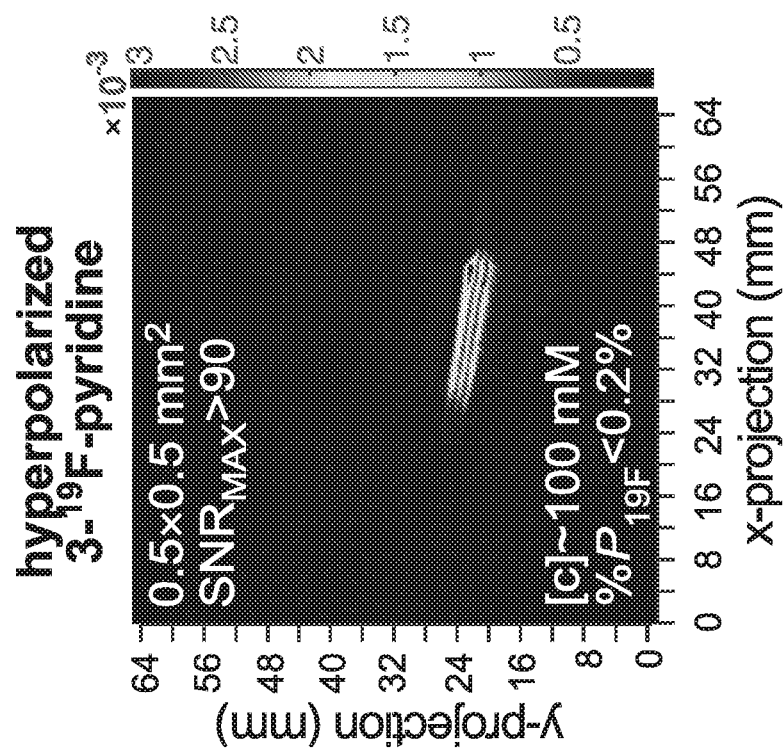

Experiments with 2-$^{19}F$-pyridine and 2,3,4,5,6-$^{19}F$-pyridine did not yield any HP hydride signatures or $^1H/^{19}F$ HP substrate resonances, likely owing to the effects of steric hindrance; therefore, further studies exploring the feasibility of applications were performed with HP 3-$^{19}F$-Py. First, FIG. 8A demonstrates the feasibility of $^{19}F$ HP MRI imaging using SABRE-SHEATH. The obtained HP $^{19}F$ MR image is from a tilted 5 mm NMR tube with 0.5×0.5 mm² in-plane spatial resolution, and was obtained with a $^1$H surface coil (conveniently re-tuned to $^{19}$F resonance frequency) placed underneath the NMR tube containing the HP solution. Note that the tube contains ⅟₃₂ in. ID tubing (⅟₆₄ in. (~0.4 mm) wall thickness) inserted all the way to the bottom of the NMR tube, which is resolved in this image as two narrow bands with depressed signal. The corresponding image from a thermally polarized sample (FIG. 8B) yielded only noise.

Figure 8D:
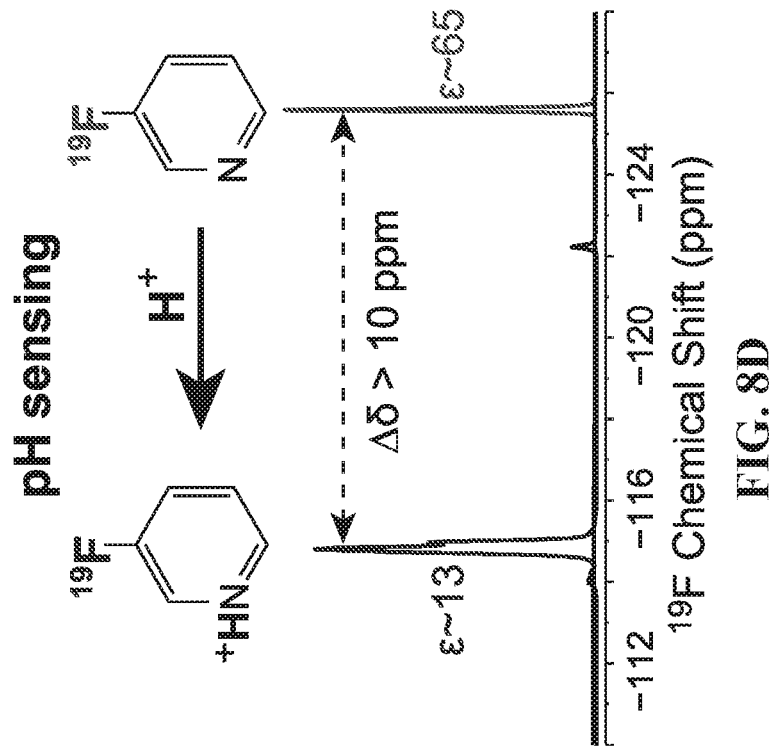
Figure 8C:
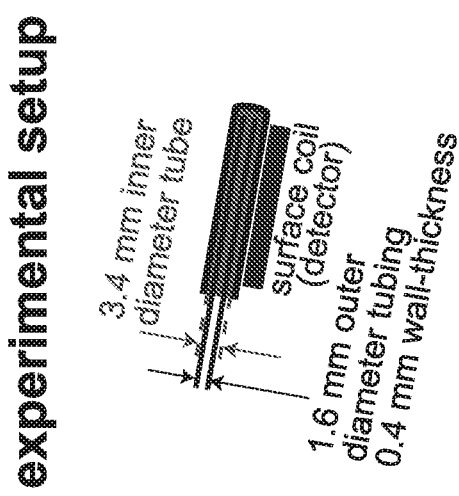

Next, the feasibility of hyperpolarized pH sensing with HP $^{19}$F was also demonstrated (FIG. 8D). First, 3-$^{19}$F-Py was hyperpolarized at pH>>pKa in the deprotonated form (red resonance). The HP solution was then spiked with ~0.3 mL of concentrated HCl, and the corresponding HP NMR signal of the protonated form (blue resonance) was frequency shifted by ~10.5 ppm (note that the level of hyperpolarization of the protonated form is lower than that of the deprotonated form due to polarization relaxation because of an additional >10 s-long sample handling time). While the corresponding frequency shift of $^{15}$N sites is ~90 ppm for pH sensing applications (i.e. appearing to be ~9 times greater on the ppm scale), it is noted that on the Hz frequency scale, these nuclei actually provide near-equal dynamic range, because the $^{19}$F spin has a >9-fold greater gyromagnetic ratio compared to that of $^{15}$N. It is also noted that the absolute spectral sensitivity of $^{19}$F to changes in pH is >30 times greater than that of similar proton sites.

$^{19}$F has negligible natural occurrence in biology, which provides a benefit virtually zero background signal for in vivo $^{19}$F spectroscopic and imaging applications. Naturally, the $^{19}$F SABRE-SHEATH hyperpolarization demonstrated here could be exploited for many biomedical applications, including in vivo pH sensing. Moreover, approximately 20% of drugs contain $^{19}$F in their structures, some of which can be potentially suitable for $^{19}$F SABRE-SHEATH hyperpolarization in the context of theranostic applications (e.g. following biodistribution of 5-fluorouracil in cancer, which has a molecular framework potentially amenable to already-existing SABRE catalysts). Furthermore, because of the relatively high sensitivity of $^{19}$F (endowed by its large gyromagnetic ratio and 100% natural abundance) and strong spectral sensitivity to the molecular environment, combined with the near-zero background signal and the possibility of using the available $^1$H channel in clinical MRI scanners (vs. the need for dedicated X-nucleus channels for $^{13}$C and $^{15}$N imaging), it is speculated that HP $^{19}$F (enabled by SABRE-SHEATH) can potentially become a game-changing technology for molecular imaging. The relatively short $^{19}$F T$_1$ value of the agent employed here is of potential concern in the context of potential biomedical translation, and contrast agents with longer $^{19}$F in vivo T1 need to be developed for future in vivo translation of the presented work. It is noted however that pH sensing using non-hyperpolarized $^{19}$F injectable agents has been shown successful previously.

In summary, the present disclosure demonstrates the feasibility of $^{19}$F hyperpolarization via SABRE-SHEATH, achieving signal enhancements of the order of ~100-fold at 9.4 T (PF ~0.28%). It is likely that the degree of hyperpolarization can be improved through the optimization of conditions, similarly to recent reports of $P_{15N}$>20% and $P_H$>50%. The presented method may also be combined with recent reports of heterogeneous and aqueous SABRE hyperpolarization, likely required for future biomedical translation for pH imaging, theranostics, and other envisioned applications.

Experimental Procedures

3-$^{19}$F-pyridine (0.10 M final concentration) and pre-activated iridium catalyst ([IrCl(COD)(IMes)], 0.005 M final concentration) and methanol-d$_4$ were added to an Eppendorf safe-lock tube. The stock solution was then flushed with Argon and vortexed. In order to achieve lower tracer and catalyst concentration, the stock solution was diluted.

The stock solution was transferred into an Argon-filled medium-walled NMR sample tube (5 mm medium wall precision, 3.43 mm ID, 9 in. long, Wilmad Glass, P/N 503-PS-9) equipped with a Teflon tube extension: 0.25 in. OD, ³⁄₁₆ in. ID. The Teflon extension was approximately 7 cm in length. The tube was connected to the previously described setup using a Wye push-to-connect adapter. The SABRE sample was activated by bubbling parahydrogen at 20-50 sccm for ~20 minutes using ~50% parahydrogen. The parahydrogen flow rate was controlled using a mass flow controller (Sierra Instruments, Monterey, Calif., model number C100L-DD-OV1-SV1-PV2-V1-S0-C0).

The SABRE-SHEATH hyperpolarization procedure was performed using the approach described previously. The sample solution was bubbled with ~50% parahydrogen at 100 sccm for ~30 s (and at ~6 atm) inside the magnetic shield. More specifically, the magnetic field in the lab was attenuated using a three-layered mu-metal shield (6 in. ID & 15 in. in length, part number ZG-206, Magnetic Shield Corp., Bensenville, Ill.); tunability of the residual micro-Tesla magnetic field was attained using a custom-built solenoid coil and a power supply (GPRS series, GW INSTEK) with an in-series variable-resistor bank. After cessation of parahydrogen bubbling, the sample was quickly transferred from the shield to the Earth's magnetic field, followed by rapid sample insertion into the bore of a 9.4 T magnet and immediate acquisition of the $^{19}$F NMR spectrum. Typical sample transfer time (from cessation of para-H$_2$ gas to $^{19}$F detection in the 9.4 T magnet) was approximately 6 seconds. The $^{19}$F NMR signal enhancements were calculated by comparison of the intensity of thermally polarized $^{19}$F NMR spectra and the corresponding hyperpolarized $^{19}$F NMR spectra.

$^{19}$F SABRE and SABRE-SHEATH Enhancement Factor Calculation

The $^{19}$F SABRE-SHEATH signal enhancements were calculated by comparing the integral signal intensities of the $^{19}$F NMR peaks of the spectrum from a given hyperpolarized sample with the corresponding thermally polarized $^{19}$F NMR peaks of the same sample.

$$\varepsilon = S_{HP}/S_{THERMAL},$$

where $S_{HP}$ is the integral calculated for the hyperpolarized signal and $S_{THERMAL}$ is the corresponding integrated signal from the same sample under conditions of equilibrium thermal polarization at 9.4 T.

The $^{19}$F polarization percentage (% P) was calculated as follows (where % $P_{thermal}$=3.0×10$^{-3}$% is the equilibrium thermal $^{19}$F polarization at 9.4 T and room temperature):

$$\% P = \varepsilon \times \% P_{thermal} = 93 \times 3.0 \times 10^{-3}\% \approx 0.3\%$$

Hyperpolarized $^{19}$F NMR Signal Build-Up and Decay Measurements

The $^{19}$F NMR signal build-up curve (FIG. 7G) was measured by varying the parahydrogen bubbling time (for the parahydrogen bubbling through the NMR tube containing the catalyst and substrate solution) in the magnetic shield at ~5 micro-Tesla. The signal (for each timing of hyperpolarization) was recorded inside the 400 MHz NMR spectrometer (i.e. at 9.4 T) after rapid sample transfer, with each experiment corresponding to an individual data point. Following a time period of hyperpolarization, parahydrogen flow was terminated, the HP sample was quickly removed from the magnetic shield chamber and transported into 9.4 T NMR spectrometer for $^{19}$F detection.

The Earth's field $^{19}$F $T_1$ of 3-$^{19}$F-pyridine (FIG. 7F) was measured using the following procedure: Parahydrogen was bubbled through the solution in the mu-metal magnetic shield for approximately 30 s. When parahydrogen flow was stopped, the NMR tube was transferred to the Earth's field, and it was stored there for a variable period of time. Then the sample was quickly (~5 s) transferred to the high magnetic field (9.4 T) for recording the $^{19}$F NMR signal. One data point was acquired for each experiment. The decay data was then plotted as a $^{19}$F signal dependence upon the decay time at the Earth's magnetic field.

The $^{19}$F $T_1$ at high field (400 MHz, FIG. 7E), was measured on a single $^{19}$F hyperpolarized sample by employing a series of $^{19}$F NMR acquisitions using small tipping-angle (<8°) excitation RF pulses after the sample transfer to the high magnetic field of the 9.4 T/400 MHz NMR spectrometer. The decay time constant was not corrected for the minimal polarization losses caused by the RF observation pulses.

Example 3 Spin Relays Enable Efficient
Long-Range Heteronuclear Signal Amplification by
Reversible Exchange A systematic experimental study is reported on the polarization transfer to distant spins, which do not directly bind to the polarization transfer complexes employed in Signal Amplification By Reversible Exchange (SABRE) experiments. Both, long-range transfer to protons and long-range transfer to heteronuclei i.e. $^{13}$C and $^{15}$N are examined. Selective destruction of hyperpolarization on $^1$H, $^{13}$C, and $^{15}$N sites is employed, followed by their re-hyperpolarization from neighboring spins within the molecules of interest (pyridine for $^1$H studies and metronidazole-$^{15}$N$_2$-$^{13}$C$_2$ for $^{13}$C and $^{15}$N studies). It is concluded that long-range sites can be efficiently hyperpolarized when a network of spin-½ nuclei enables relayed polarization transfer (i.e. via short-range interactions between sites). In case of proton SABRE in the milli-Tesla regime, a relay network consisting of protons only is sufficient. However, in case $^{13}$C and $^{15}$N are targeted (i.e. via SABRE in SHield Enables Alignment Transfer to Heteronuclei or SABRE-SHEATH experiment), the presence of a heteronuclear network (e.g. consisting of IN) enables a relay mechanism that is significantly more efficient than the direct transfer of spin order from para-H$_2$-derived hydrides.

Introduction

Hyperpolarization techniques transiently increase nuclear spin polarization (P) by several orders of magnitude, resulting in corresponding gains in NMR signals. These techniques enable new applications including in vivo molecular imaging, which relies on preparation, administration, and MRI of exogenous hyperpolarized (HP) contrast agents. Several technologies have been developed to produce HP states of low-gamma spin ½ nuclei (e.g. $^{13}$C and $^{15}$N), which retain HP state significantly longer than protons in biomolecular motifs.

Figure 11A:
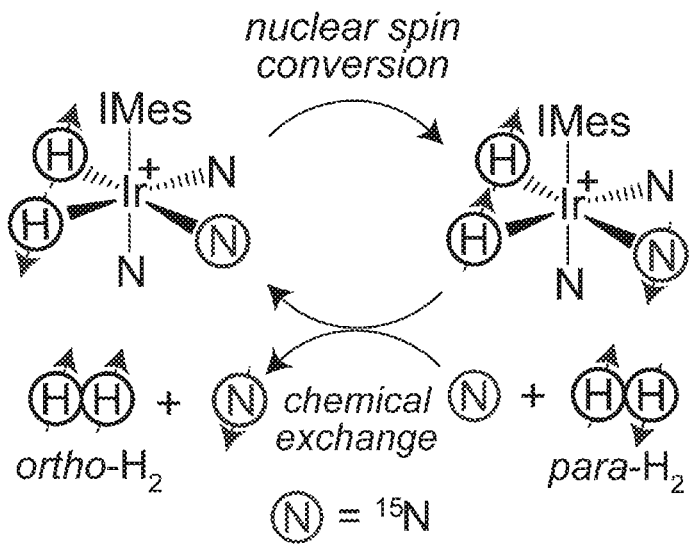
FIG. 11A: The overall schematic of SABRE hyperpolarization of $^{15}$N. Spin order is transferred from para-H$_2$ and mediated by scalar spin-spin couplings within a reversibly-formed Ir-IMes hexacoordinate complex. Direct SABRE of short-range $^{15}$N sites is accomplished via 2-bond couplings between $^{15}$N and hydride protons.

Signal Amplification by Reversible Exchange (SABRE) is the hyperpolarization method, which employs parahydrogen (para-H$_2$) as the source of spin order. SABRE relies on spontaneous polarization transfer from para-H$_2$-derived hydrides to a substrate on polarization transfer catalysts. The SABRE polarization transfer is primarily accomplished via spin-spin interactions (i.e. J-couplings). While other interactions may contribute, they are generally orders of magnitude less efficient. When polarization transfer is performed in milli-Tesla (mT) magnetic fields, the polarization from para-H$_2$-derived hydrides is spontaneously transferred to proton sites in substrates, enabling $^1$H polarization values (% $P_H$) of up to 50%. In this case, proton-proton spin-spin couplings ($J_{H-H}$) enable SABRE polarization transfer. Another variant of this technique dubbed SABRE in SHield Enables Alignment Transfer to Heteronuclei (SABRE-SHEATH) is an efficient process for hyperpolarizing $^{15}$N sites, in one example providing more than 20% polarization in 1 minute. $^{15}$N-hyperpolarization is of particular interest, because it enables long hyperpolarization lifetimes and exponential decay constants. In some cases, $^{15}$N exponential decay constant can exceed 20 minutes. SABRE-SHEATH is accomplished at micro-Tesla (μT) magnetic fields, enabling spontaneous polarization transfer from para-H$_2$-derived hydrides to heteronuclei, as illustrated in FIG. 11A. In case of $^{15}$N SABRE-SHEATH proton-nitrogen-15 spin-spin couplings ($J_{H-15N}$) enable the spontaneous polarization transfer. While polarization transfer between nuclear spins in the same molecule in solution is an extremely well documented area, the case is less clear for SABRE and SABRE-SHEATH, which occur within a complex with finite lifetime, and which involves several changes of the external magnetic field.

Previously, this approach has been bolstered by a series of advancements from proof-of-principle demonstrations in organic solvents (including "neat" substrates) all the way to demonstrations of SABRE-SHEATH enhancement under heterogeneous catalytic conditions and catalysis in aqueous media, which in principle will enable the preparation of pure aqueous $^{15}$N HP compounds for potential in vivo use. Moreover, the scope of amendable bio-structures has been expanded from N-heterocycles to Schiff bases, diazirines, and nitriles.

Figure 11B:
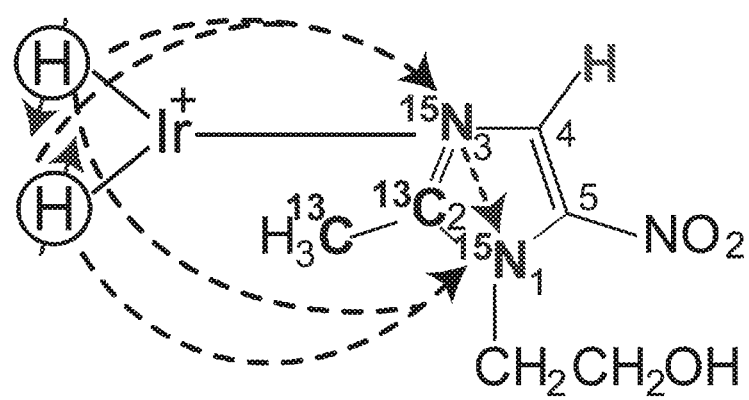
FIG. 11B: the molecular framework (note axial ligand of polarization transfer from hydride protons via short- and long-range spin-spin (J) couplings.

However, despite these successes, to date SABRE-SHEATH has been primarily employed for hyperpolarization of $^{15}$N sites that bind directly to metal centers via two-bond spin-spin couplings (i.e. short-range couplings to substrate $^{15}$N sites directly binding to catalysts like Ir-IMes [IMes=1,3-bis(2,4,6-trimethylphenyl)imidazole-2-ylidene], FIG. 11A). Efforts to hyperpolarize long-range $^{15}$N sites (i.e. more than 2 chemical bonds away from para-H$_2$-hydrides) showed that polarization efficiency is reduced by more than an order of magnitude—presenting a clear obstacle for expanding SABRE hyperpolarization technology to broader classes of substrates. Moreover, recent studies of direct $^{13}$C and $^{19}$F hyperpolarization via SABRE indicated that the problem can be mitigated if the nitrogen sites binding the iridium metal centers are labeled with $^{15}$N nuclei as opposed to naturally occurring quadrupolar spins. However, the obvious question regarding the mechanism of polarization transfer (and more importantly its limitations) was unanswered. Specifically: "Is SABRE of distant heteronuclei accomplished directly via long-range J-couplings, or does it work indirectly via relay through a network of spins (FIG. 11B)?

In some embodiments, disclosed herein is experimental evidence that SABRE of long-range $^{15}$N and $^{13}$C sites is efficient in the presence of a relay network connected by close-range spin-spin couplings. While the data presented does not rule out a direct mechanism via weak long-range J-couplings, the indirect mechanism is significantly more efficient than the direct polarization transfer (i.e., the enhancements observed cannot be fully explained by long-range transfer; although long-range transfer is possible, it leads to weaker enhancements). The presented disclosure enables techniques for efficient SABRE-SHEATH hyperpolarization of remote heteronuclear sites.

Methods

All NMR spectra were recorded using a 9.4 T Bruker Avance III high-resolution NMR spectrometer equipped with a broadband dual-channel NMR probe. All SABRE experiments were performed using ~50% para-H$_2$. All sample manipulations related to the sample transfer between magnetic fields (i.e. the Magnetic Field Cycling (MFC) procedures) were performed manually (FIGS. 12A-12B and FIGS. 13A-13B). The NMR spectra from metronidazole-$^{15}$N$_2$-$^{13}$C$_2$ (Millipore-Sigma P/N 32744-10MG) samples were recorded in medium-wall 5 mm NMR tubes, whereas the spectra from signal reference samples were recorded using standard 5 mm NMR tubes.

Preparation of solutions. Previously synthesized IrIMes catalyst was used for the described studies. Metronidazole-$^{15}$N$_2$-$^{13}$C$_2$ (~20 mM final concentration) and pre-activated iridium catalyst ([IrCl(COD)(IMes)], ~1.0 mM final concentration) and methanol-di were prepared from stock solutions of Metronidazole-$^{15}$N$_2$-$^{13}$C$_2$ (40 mM) and ([IrCl(COD)(IMes)], 2.0 mM). Both solutions were flushed with Argon and vortexed (at least three times) in an Eppendorf safe-lock tube and Duran bottle (10 mL GL25) correspondently. While Metronidazole-$^{15}$N$_2$-$^{13}$C$_2$ solution was used over a period of several days (stored at ~6° C.), ([IrCl(COD)(1Mes)] was prepared fresh each day and stored for <10 hours in a refrigerator (~6° C.). A portion (~0.3 mL) of each stock solutions was transferred into an Argon-filled medium-walled 5 mm NMR sample tube: 9 in.-long, 3.43-mm inner diameter (ID) (17Vilmad Glass, P/N 503-PS-9) equipped with a Teflon tube extension: 0.25 in. outer diameter (OD), 3/16 in. ID. The Teflon extension was approximately 3-in. long. The tube was connected to the previously described setup. The best results were obtained by SABRE sample activation by bubbling para-H2 for ~3 minutes (at 90 sccm & 65 psi) and leaving sample for ~1 hour under para-H$_2$ at 65 psi.

Figure 12A:
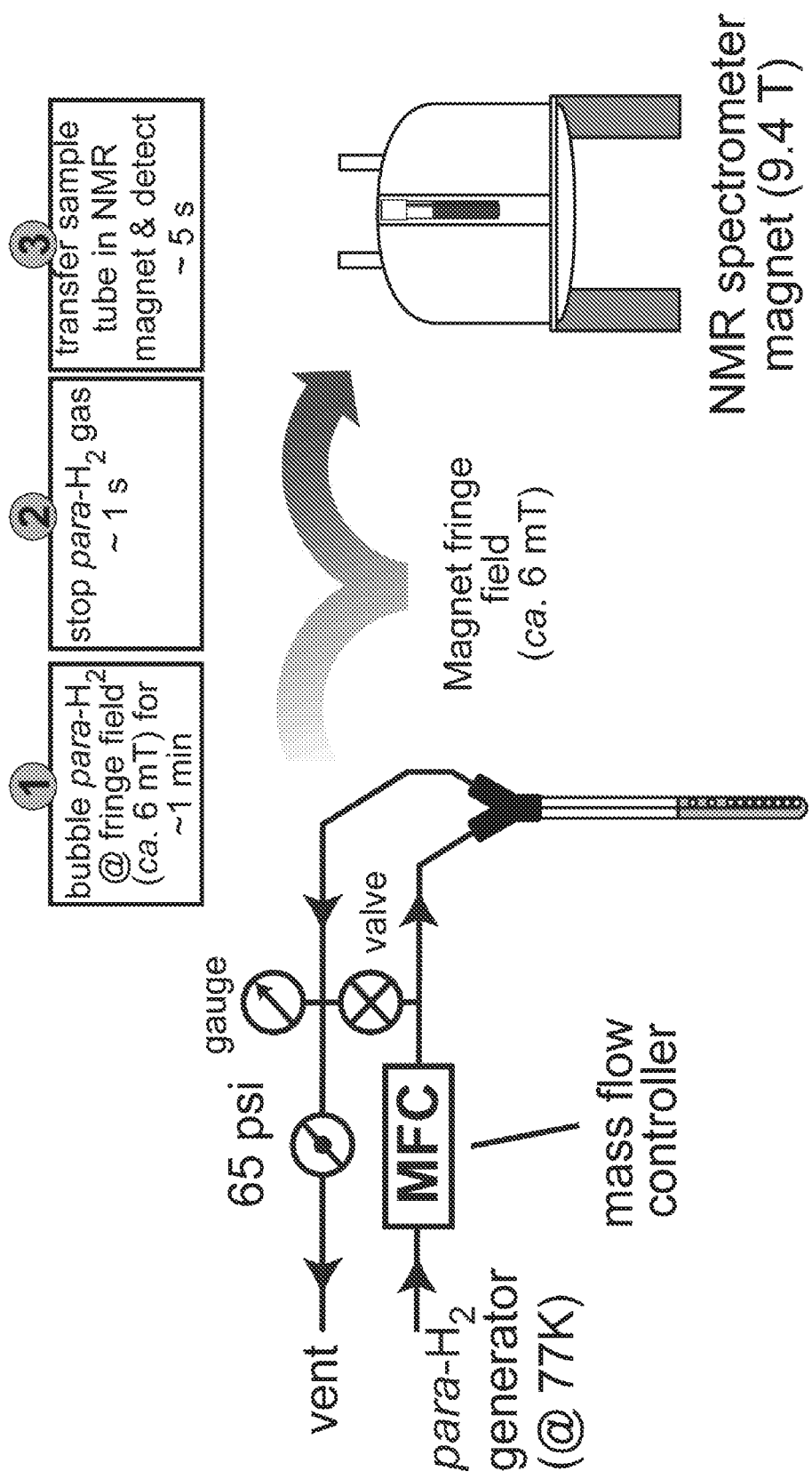
FIG. 12A: the schematic of SABRE polarization experiments for $^1$H hyperpolarization studies.
Figure 12B:
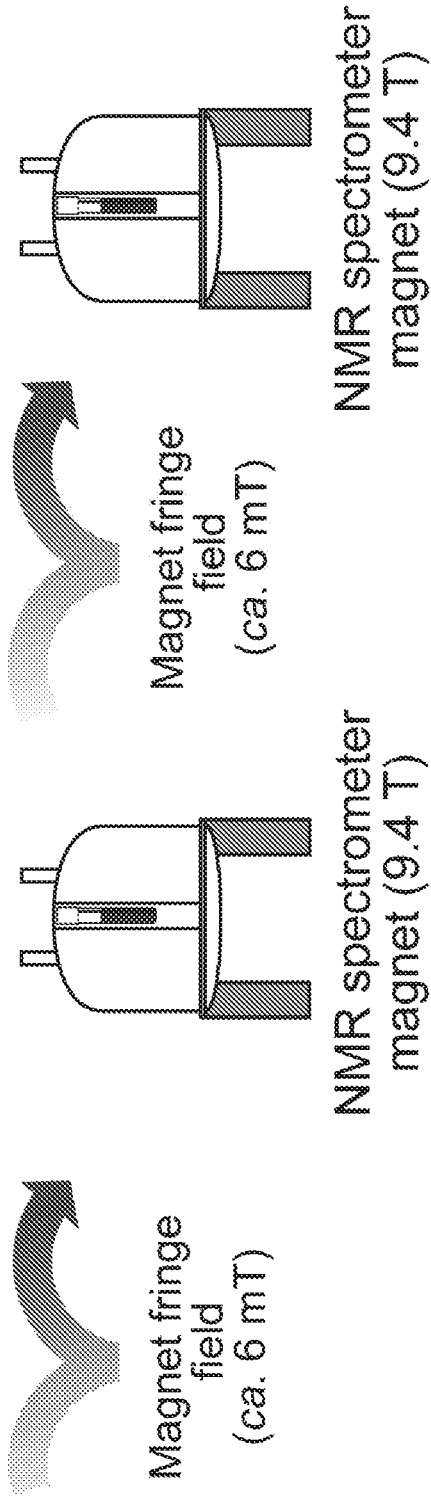
FIG. 12B: the schematic of SABRE re-polarization experiments for $^1$H hyperpolarization studies.
Figure 13A:
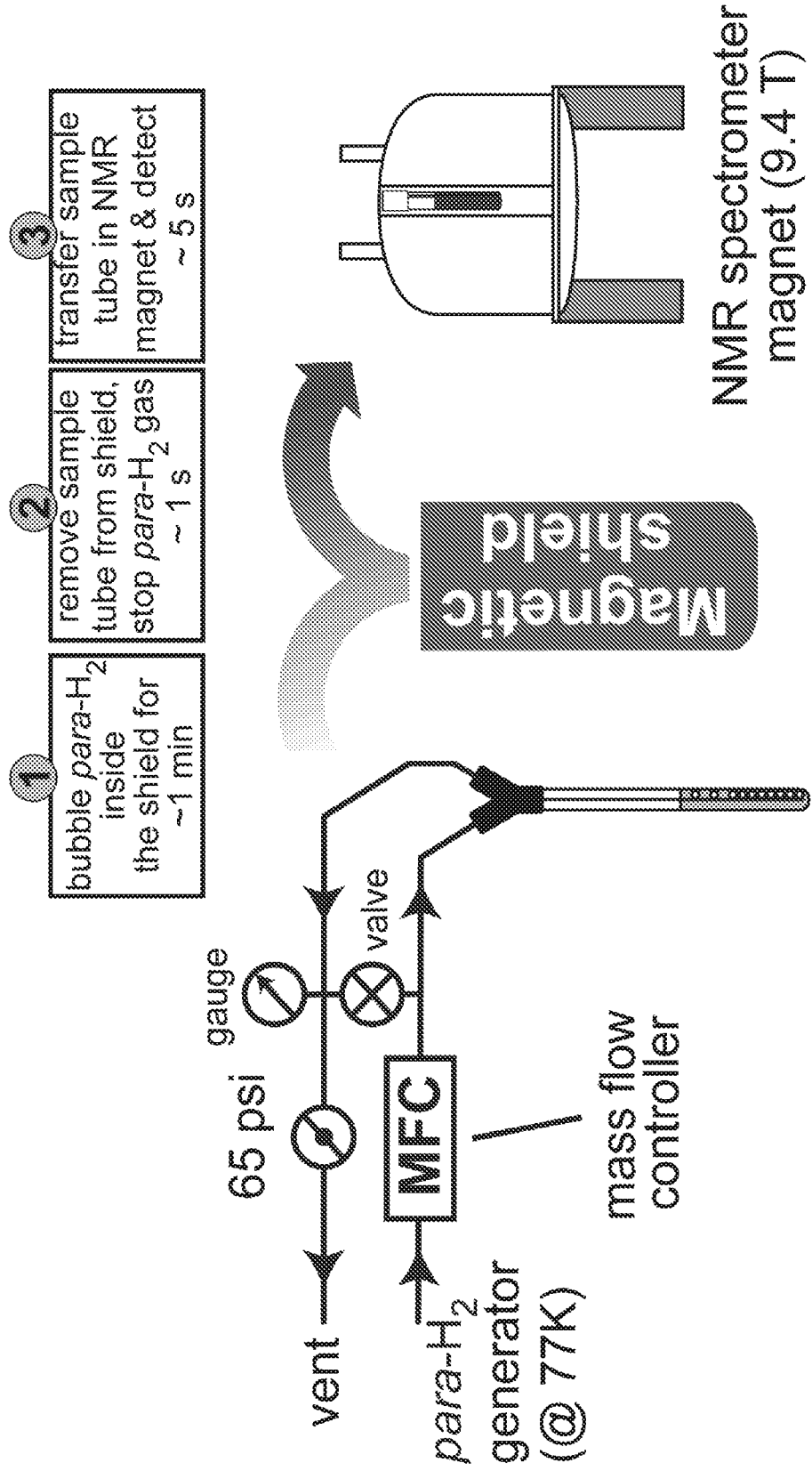
FIG. 13A: the schematic of SABRE-SHEATH polarization experiments for $^{15}$N and $^{13}$C hyperpolarization studies.
Figure 13B:
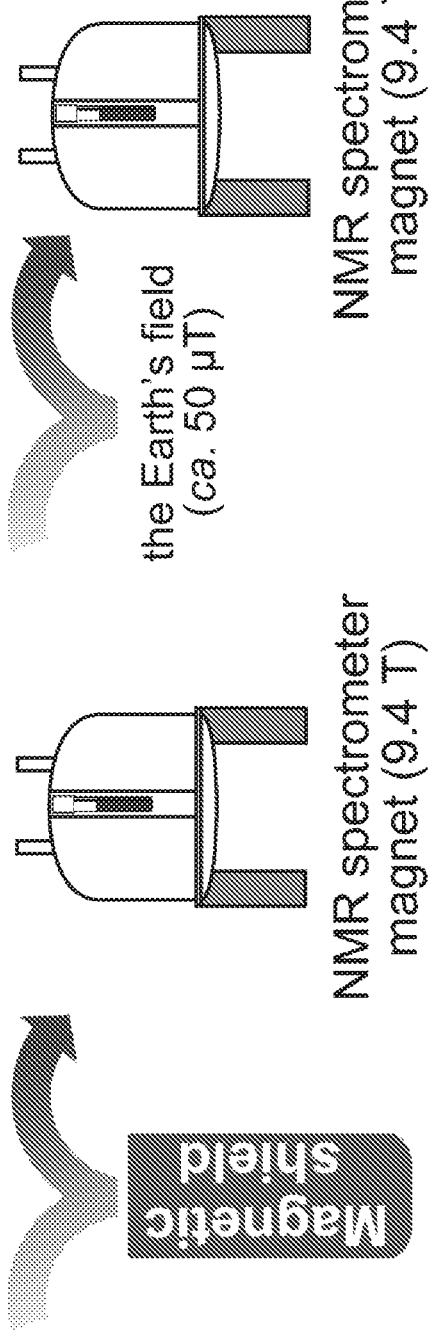
FIG. 13B: the schematic of SABRE-SHEATH re-polarization experiments for $^{15}$N and $^{13}$C hyperpolarization studies.

SABRE hyperpolarization. For SABRE experiments, the para-H$_2$ flow rate (50 sccm, ~1 minute of bubbling) was controlled using a mass flow controller (Sierra Instruments, Monterey, Calif., P/N C100L-DD-OV1-SV1-PV2-V1-S0-C0). The schematic of SABRE experimental setup is shown in FIG. 12A, and the corresponding sequence of the events is shown in FIG. 12B. Micro-Tesla magnetic field was created by attenuating the Earth's magnetic field using a three-layered mu-metal shield (Magnetic Shield Corp., Bensenville, Ill., P/N ZG-206,). The tuning of SABRE-SHEATH magnetic field was achieved by custom-built solenoid coil (>90% homogeneity over >15 cm length) and a power supply (GW INSTEK, GPRS series) with variable-resistor bank connected in series with the magnet coil. When para-H$_2$ bubbling was stopped, the sample was transferred from the shield to the Earth's magnetic field (ca. 50 µT), followed by rapid sample transfer into a 9.4 T magnet of the NMR spectrometer for data acquisition or further manipulations as described in the main text. Typical sample transfer time (from cessation of para-H$_2$ gas to $^{15}$N/$^{13}$C/$^{1}$H signal detection) was 4-7 seconds. The schematic of SABRE-SHEATH experimental setup is shown in FIG. 13A, and the corresponding sequence of the events is shown in FIG. 13B.

In certain embodiments, disclosed is the use of magnetic field cycling (MFC) to the Earth's magnetic field, ca. 50 µT, (SABRE-SHEATH, FIG. 13B) for $^{15}$N re-polarization, whereas $^1$H re-polarization (SABRE, FIG. 12B) employs MFC to the fringe field, ca. 6 mT, due to the difference in the matching conditions for efficient $^{15}$N→$^{15}$N or $^1$H→$^1$H re-polarization respectively.

Computation of NMR signal and nuclear spin polarization enhancements. The signal enhancements were computed as the following. $^1$H enhancements were computed by diving the HP signal magnitude by the magnitude of thermally polarized signals. In case of $^{15}$N and $^{13}$C, the thermally polarized signals were generally very low, and therefore, external signal reference was employed. The enhancements were computed as follows:

$$\varepsilon = \frac{S_{HP}}{S_{REF}} \times \frac{C_{REF}}{C_{HP}} \times \frac{A_{REF}}{A_{HP}} \times \frac{N_{REF}}{N_{HP}}$$

where $S_{HP}$ and $S_{REF}$ are NMR signals for HP state and thermally polarized signal reference samples respectively, $C_{REF}$ and $C_{HP}$ are the effective isotope concentrations of thermally polarized signal reference and HP samples respectively, $A_{REF}$ and $A_{HP}$ are the solution cross-sections in the NMR tube of thermally polarized signal reference and HP samples respectively, and $N_{REF}$ and $H_{HP}$ are the numbers of symmetrical sites per molecule for the thermally polarized signal reference and HP samples respectively ($A_{REF}/A_{HP}$ was ~1.85 as described earlier). Percentage polarization was computed by multiplying signal enhancement c by the equilibrium nuclear spin polarization of a given spin at 9.4 T and 298K: 3.2×10$^{-3}$% ($^1$H), 8.1×10$^{-4}$% ($^{13}$C), 3.3×10$^{-4}$% ($^{15}$N).

Results and Discussion

General Consideration. Briefly, the reader is reminded that in case of traditional SABRE (i.e. hyperpolarization of proton sites), the matching condition for J-coupling ($^1$H-$^1$H) mediated polarization transfer occurs at a few mT magnetic field. In case of SABRE-SHEATH (i.e. hyperpolarization of heteronuclear sites, e.g. $^{15}$N and $^{13}$C), the matching condition for J-coupling (e.g., $^1$H-$^{15}$N) mediated polarization transfer occurs at µT magnetic field. Detailed theory is provided in earlier works of Duckett et al. and Theis at al.

SABRE hyperpolarization of pyridine proton sites. The first reports of SABRE demonstrated that proton sites at least six-bonds away can be efficiently hyperpolarized. The theoretical basis for SABRE indicated that polarization transfer from para-H$_2$-hydrides to substrate protons is accomplished via a networks of proton-proton couplings, although the recent study by Eshuis and co-workers determined the values of these four-, five-, and six-bond spin-spin couplings, and postulated that these long-range couplings may also enable the canonical SABRE effect via the direct transfer of spin order.

Figure 21:
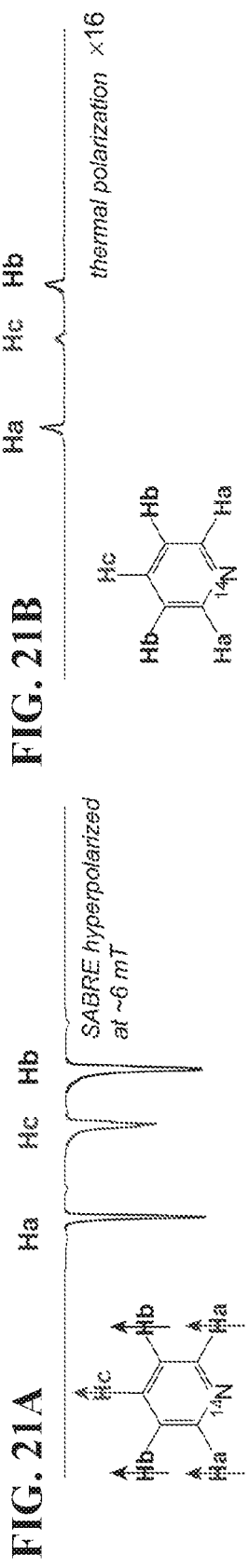
FIG. 21 shows $^1$H NMR spectra of SABRE-hyperpolarized ~100 mM pyridine solutions in methanol-d$_4$.
Figure 21:
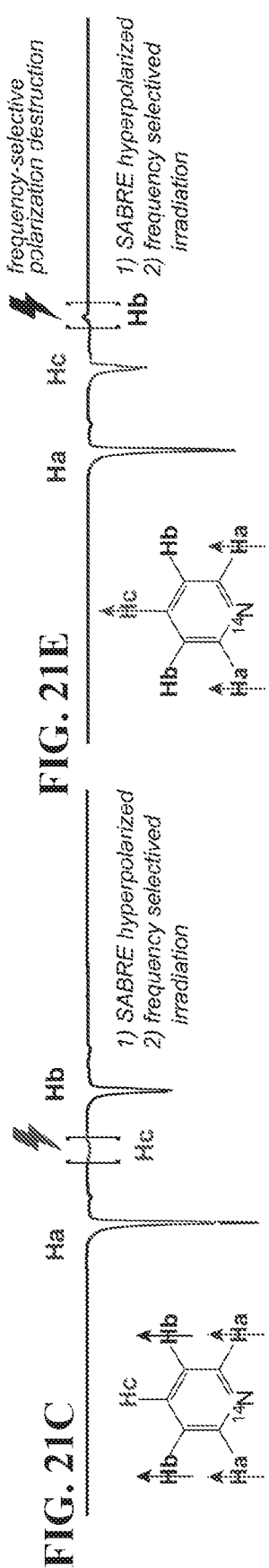
Figure 21:
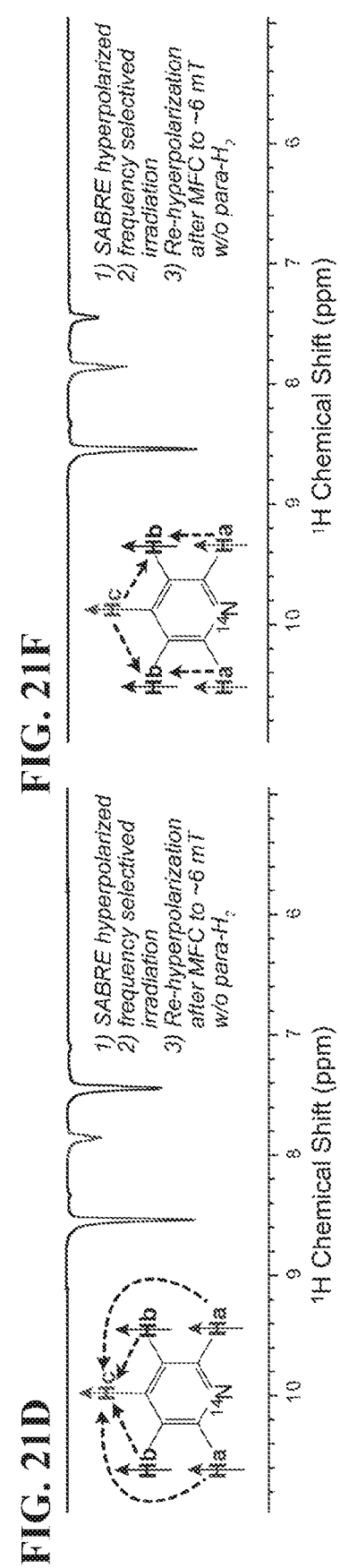

In certain embodiments, disclosed is an approach for studying $^1$H SABRE, which includes selective spin destruction of HP resonances of ortho-pyridine protons (denoted as Ha in FIG. 36A) after the sample is hyperpolarized at magnetic field of ~6 mT and para-H$_2$ bubbling is stopped (FIG. 36B). After destroying the Ha polarization with a frequency-selective pulse (FIG. 14C), the sample was moved back into the ~6 mT field, and finally, the sample was returned to the 9.4 T NMR spectrometer for detection (this procedure effectively represents magnetic field cycling or MFC—the details of the experimental setup and the involved steps are shown in FIGS. 12A-12B of the Methods section). The resulting spectrum shown in FIG. 14D indeed shows that the Ha HP state is successfully re-created using the meta- and para-(Hb and Hc) protons as hyperpolarization reservoirs. Corresponding datasets showing HP state destruction and re-creation for the Hb and Hc protons are shown in FIG. 21.

All-in-all, the experimental results shown in FIGS. 14A, 14B, 14C, 14D and FIG. 21 are clearly consistent with the canonical (i.e. $^1$H) SABRE effect in the mT regime may indeed rely on the network of proton-proton couplings, in agreement with pioneering studies by Duckett and co-workers.

Figure 15:
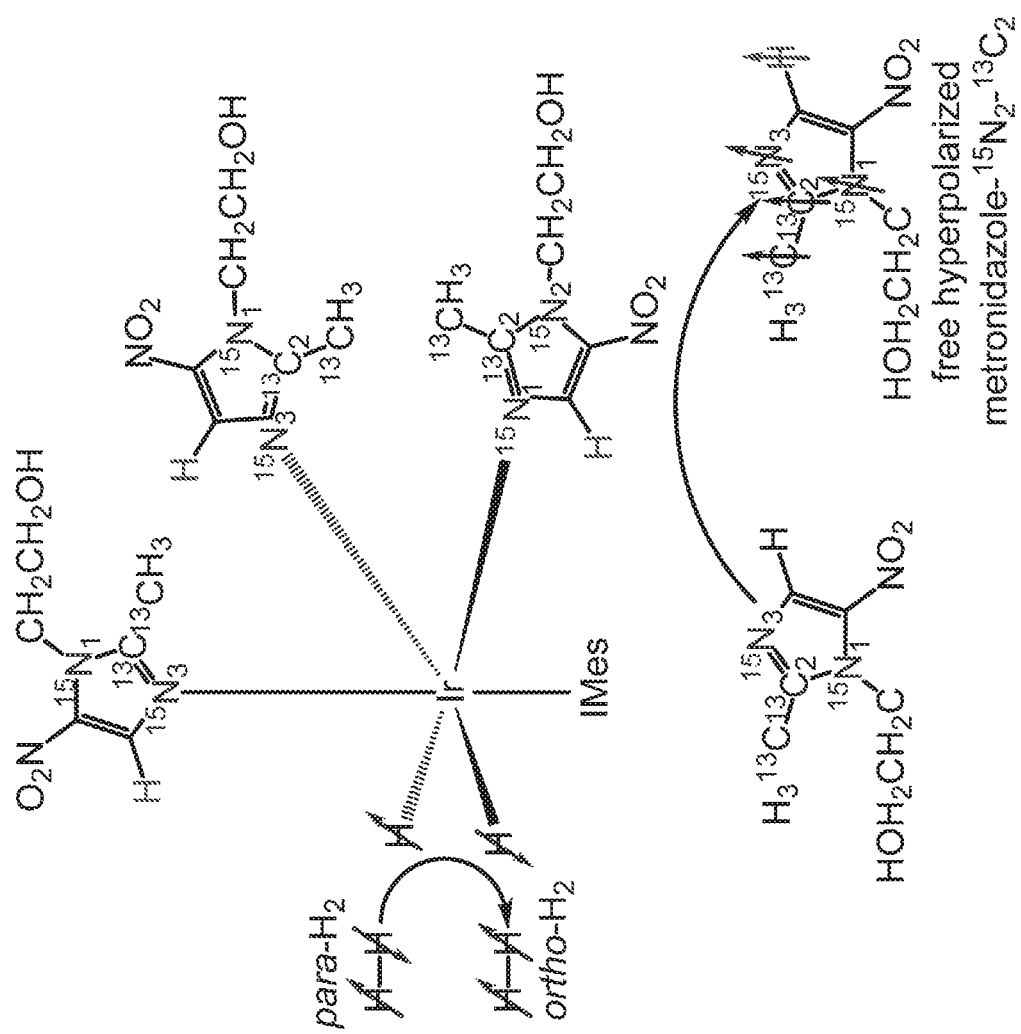
FIG. 15 shows a schematic of the SABRE-SHEATH hyperpolarization process of metronidazole-$^{15}$N$_2$-$^{13}$C$_2$ using transfer of spin order from para-H$_2$ on an Ir-IMes hexacoordinate complex. SABRE-SHEATH is accomplished via spin-spin couplings between para-H$_2$-derived hydride protons and nuclear spins of the equatorial exchangeable ligands. The axial ligands are not exchangeable.

SABRE hyperpolarization of metronidazole-$^{15}$N$_2$-$^{13}$C$_2$ in micro-Tesla (µT) magnetic fields (SABRE-SHEATH). Hyperpolarization in µT magnetic fields was performed using a metal magnetic shield that attenuates the Earth's magnetic field (ca. 50 µT) down to the sub-µT regime (FIG. 13A). The structure of the activated complex and the schematic of SABRE-SHEATH process are shown in FIG. 15. Efficient $^{15}$N and $^{13}$C SABRE-SHEATH hyperpolarization has been demonstrated previously, and no significant effort was made to optimize polarization parameters (e.g., temperature and µT field) for the present study.

Figure 16E:
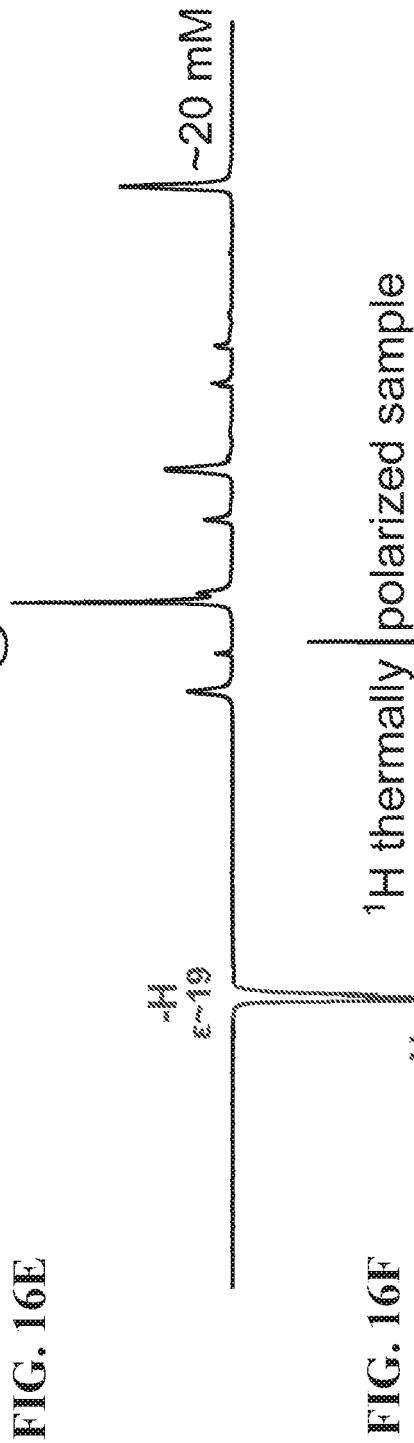
Figure 16F:
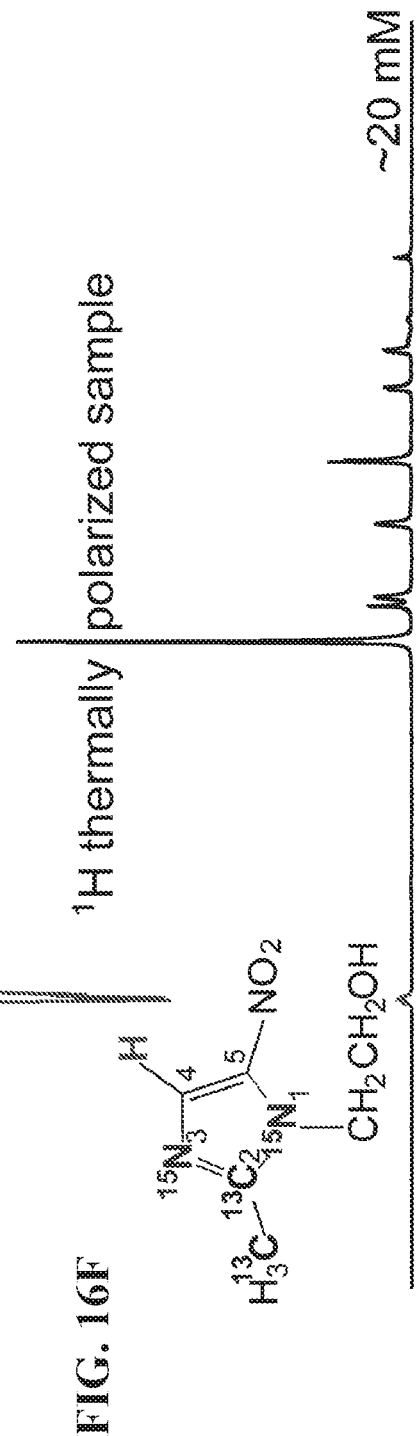
Figure 16G:
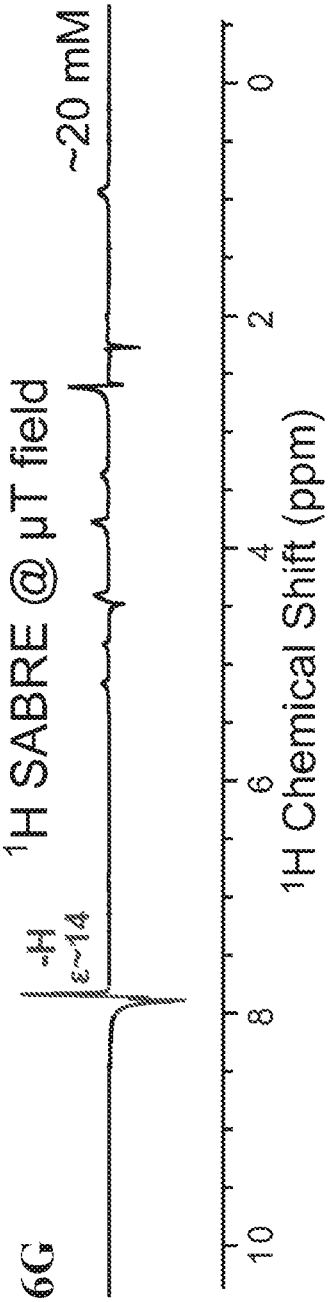

The following polarization levels were achieved for ~20 mM metronidazole-$^{15}$N$_2$-$^{13}$C$_2$ solutions in methanol-d$_4$ using 50% para-H$_2$: $\varepsilon_{15N1}$~4,000 (% P$_{15N1}$~1.3%), $\varepsilon_{15N3}$~4,700 (% P$_{15N1}$~1.5%), FIGS. 16A and 16B, $\varepsilon_{13C2}$~310 (% P$_{13C2}$~0.3%), $\varepsilon_{13CH3}$~230 (% P$_{13CH3}$~0.2%), FIGS. 16C and 16D, $\varepsilon_H$~14 (% P$_H$~0.04%), FIGS. 16E, 16F, and 16G. If near 100% para-H$_2$ were employed, the polarization values would be effectively tripled. % P$_{15N}$ values are within the expected ranges for the employed concentration regime. % P$_{13C}$ values are several times lower than % P$_{15N}$, because initial micro-Tesla field optimization was performed for $^{15}$N spins, and the optimization of polarization efficiency was outside the scope of the presented mechanistic study. % P$_H$ values are significantly lower than % P$_{15N}$ and % P$_{13C}$ values, because µT fields are not optimal for proton SABRE.

Figure 17:
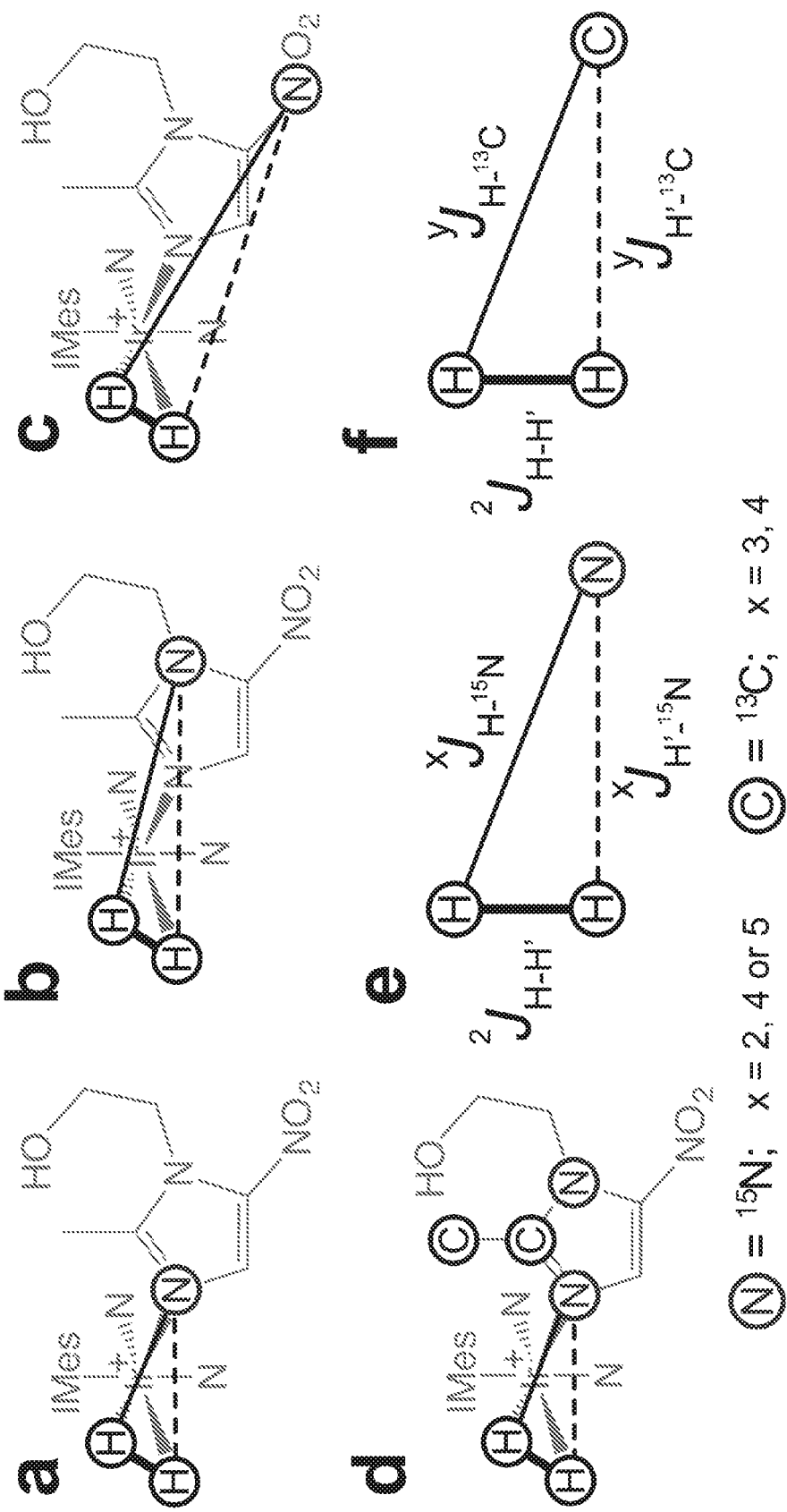
FIG. 17 shows the relevant spin-spin coupling schemes for three $^{15}$N sites at natural abundance of $^{15}$N and $^{13}$C (FIGS. 17A, 17B, and 17C) and the network for labeled metronidazole-$^{15}$N$_2$-$^{13}$C$_2$ (FIG. 17D). Only two-bond heteronuclear couplings are shown in FIG. 17D.

SABRE-SHEATH hyperpolarization of long-range $^{15}$N sites. $^{15}$N hyperpolarization of metronidazole at natural abundance of $^{15}$N (~0.3%) and $^{13}$C (~1.1%) isotopes was recently shown. In that work, the efficiency of SABRE-SHEATH hyperpolarization (gauged as % P$_{15N}$) of $^{15}$N$_1$ and —$^{15}$NO$_2$ sites was significantly lower (by more than an order of magnitude) than that of the $^{15}$N$_3$ site. Low natural $^{13}$C/$^{15}$N abundance results in simplification of the spin system (participating in SABRE-SHEATH), effectively reducing it to a three-spin system (FIG. 17), because the statistical probability of the simultaneous presence of two spins (e.g. $^{15}$N and $^{15}$N or $^{15}$N and $^{13}$C) is two orders of magnitude lower than the statistical probability of the structures shown in FIG. 17A-17C (SABRE relevant spin-spin couplings for direct polarization transfer are shown in FIGS. 17E and 17F).

The $^{15}$N SABRE-SHEATH polarization of metronidazole-$^{15}$N$_2$-$^{13}$C$_2$ shows that polarization efficiency of $^{15}$N$_1$ site is 85% of that of the $^{15}$N$_3$ site (FIG. 16A), which is markedly different from the previously reported corresponding value of 2%. This more than 40-fold improvement of hyperpolarization at $^{15}$N$_1$ can be rationalized by the presence of $^{15}$N$_3$ and $^{13}$C sites in this labeled molecule, which provides a J-coupling network enabling relayed SABRE-SHEATH polarization transfer (instead of direct H→$^{15}$N$_1$ transfer). In the relayed case, two-bond couplings ($^2$J$_{H-15N3}$ and $^2$J$_{H-15N3}$) enable hyperpolarization of the $^{15}$N$_3$ site, and $^{15}$N hyperpolarization is then propagated to other $^{13}$C and $^{15}$N sites via the heteronuclear coupling network.

Figure 19:
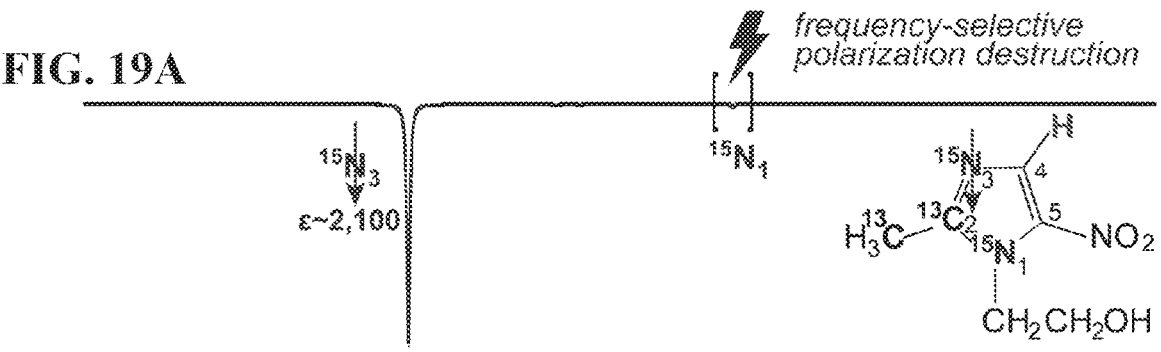
FIG. 19 shows $^{15}$N NMR spectra of HP metronidazole-$^{15}$N$_2$-$^{13}$C$_2$.
Figure 19:
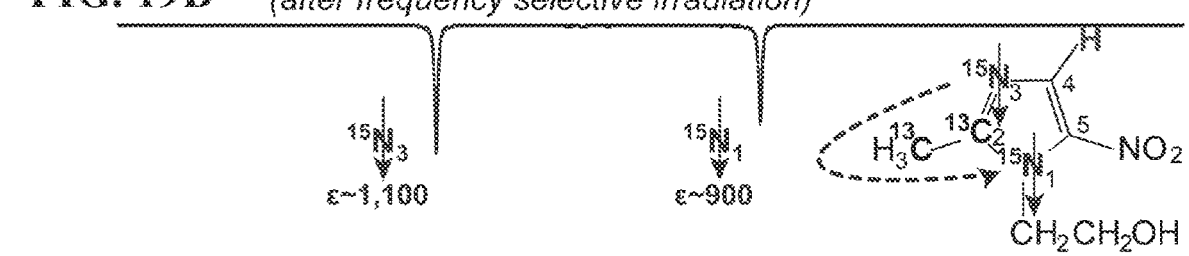
Figure 19:
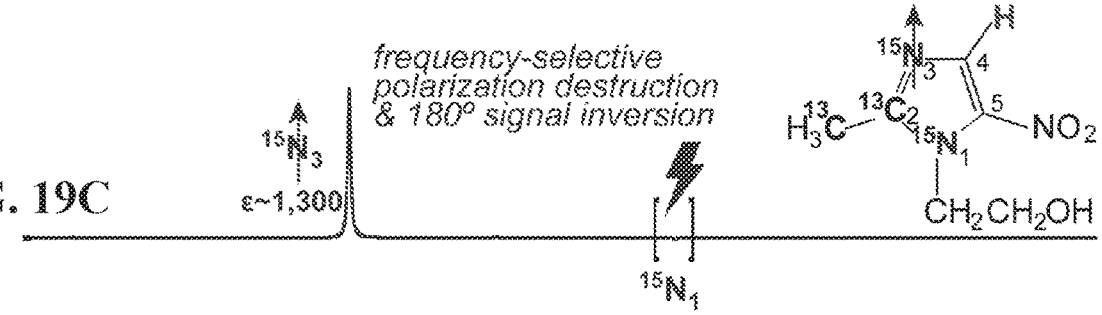
Figure 19:
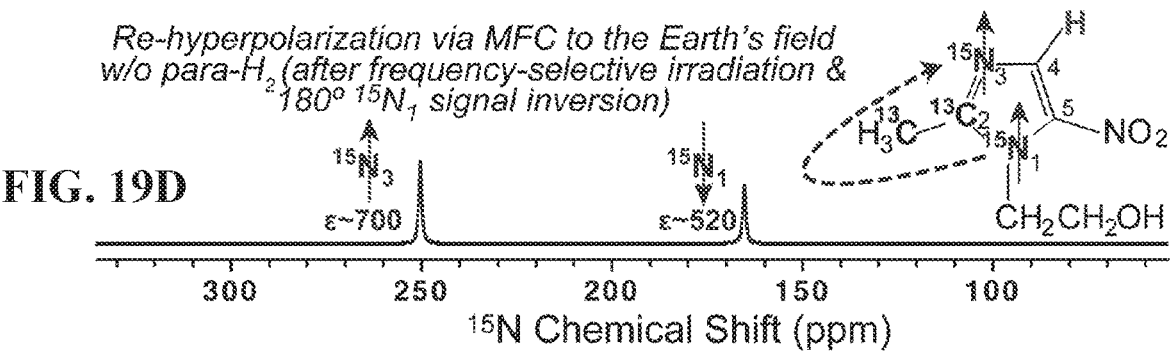

Additional experimental evidence for the relayed nature of such polarization transfer is provided in FIG. 18 and FIG. 19. For these experiments the HP sample was inserted in the 9.4 T NMR spectrometer and the $^{15}$N$_3$ hyperpolarization was destroyed using frequency-selective RF pulses (note that the $^{15}$N$_1$ polarization was preserved in this case, FIG. 18A). The relevant setup and sample manipulation steps are shown in FIG. 13B. Following this selective polarization-destruction procedure, the sample was transferred into the Earth's magnetic field (ca. 50 µT) to enable 're-mixing' of heteronuclear polarization (no bubbling of fresh para-H$_2$ is performed). Lastly, the sample was returned into the NMR spectrometer for read-out. After this magnetic field cycling (MFC), the polarization of $^{15}$N$_3$ is recovered to nearly the same level as the one for the $^{15}$N$_1$ site, as shown in FIG. 18B. It is noted that the T$_1$ of $^{15}$N sites is typically on the order of 1 minute or greater, and a significant fraction of hyperpolarization can be retained after 10-30 seconds of manipulation time required in such experiments. It is also noted that para-H$_2$ bubbling employed in the initial SABRE-SHEATH procedure was stopped before the sample left the magnetic shield for the first time. It is also noted that even when the SABRE hyperpolarization experiment was performed at the (higher) Earth's magnetic field (control experiment), the achieved polarization on $^{15}$N$_1$ and $^{15}$N$_3$ sites (FIG. 18C) was lower than the one achieved in FIG. 18B. When combined, this evidence supports the conclusion that in the MFC procedure, the $^{15}$N$_3$ site was re-hyperpolarized using the hyperpolarization pool of the $^{15}$N$_1$ site. While some polarization transfer from $^{13}$C is also potentially possible, it is less likely because HP $^{13}$C sites depolarize more quickly and the initial polarization levels of $^{13}$C sites were significantly lower than those of $^{15}$N sites (FIG. 16A). Moreover, in a separate experiment, $^{15}$N magnetization of the HP $^{15}$N$_1$ site was inverted (using a 180° RF pulse) (FIG. 18D) prior to the second MFC procedure. As a result of the spin inversion of the $^{15}$N$_1$ site, the resulting polarization on the $^{15}$N$_3$ site followed this inversion (FIG. 18E) after MFC. Furthermore, additional experiments (FIG. 22B) shows that MFC to the fringe field of ~6 mT was not sufficient to achieve this effect, and re-hyperpolarization was less efficient.

The re-hyperpolarization mechanism requires mixing of spin states from $^{15}$N$_3$ and $^{15}$N$_1$ sites. At the Earth's field (ca. 50 µT) the chemical shift difference of the two sites (ca. 100 ppm away) is only ~0.02 Hz, which is significantly less than their J-coupling (which we estimate to be on the order of a Hertz or less). At 6 mT the frequency difference of the two sites is ~2.6 Hz, which is apparently still too large for efficient level anti-crossing. Accordingly, MFC to the Earth's field (ca. 50 µT) is required. It is also noted that performing the MFC procedure from the 9.4 T to the magnetic shield (and therefore passing the Earth's field condition twice) also leads to the $^{15}$N re-polarization (data not shown), but the effect is significantly reduced, which is likely due to additional polarization leaks (e.g. to $^{13}$C and $^1$H sites).

FIG. 19 provides additional experimental evidence for polarization transfer from $^{15}$N$_3$ site to $^{15}$NI site. Instead of applying the frequency-selective irradiation on $^{15}$N$_3$, it was applied to $^{15}$NI (FIG. 19A). Exactly analogous results are obtained. The MFC to Earth's field (ca. 50 µT) enables re-hyperpolarization of $^{15}$N$_1$ using the polarization of HP $^{15}$N$_3$ (FIG. 19B). The corresponding spin inversion experiments (FIGS. 19C and 19D) prove that $^{15}$N$_1$ site was indeed re-hyperpolarized from magnetization of HP $^{15}$N$_3$ site.

While the possibility of polarization transfer between spin V2 nuclei is predictable, e.g. between two $^{15}$N spins as shown here), demonstrating this phenomenon in the context of SABRE/SABRE-SHEATH repolarization is critical for understanding and proving the mechanism of relayed polarization transfer in weak magnetic fields. Taken together, the above evidence supports the model of relayed $^{15}$N SABRE-SHEATH polarization of long range sites, explaining the efficient polarization of a distant $^{15}$N$_1$ site that is four bonds away from the para-H2-derived metal hydrides (FIG. 17D).

SABRE-SHEATH hyperpolarization of long-range $^{13}$C sites. FIG. 16C demonstrates the efficient SABRE-SHEATH hyperpolarization of $^{13}$C sites three and four bonds away from para-H$_2$-derived hydrides. Importantly, the efficiency of $^{13}$C hyperpolarization of the —$^{13}$CH$_3$ group was ~75% of that of $^{13}$C$_2$ site; it is noted however, that—$^{13}$CH$_3$ sites may have lost disproportionately more polarization during sample transfer from μT field to 9.4 T of NMR spectrometer, because the $^{13}$C T$_1$ in methyl groups is typically significantly shorter than T$_1$ values of $^{13}$C sites without directly attached protons (e.g. the $^{13}$C$_2$ site). Therefore, the actual efficiency (at the end of the SABRE-SHEATH procedure prior to the HP sample transfer) might have been better than 75%. It was recently demonstrated that the presence of a $^{15}$N nucleus in pyridine and other similar compounds is essential for efficient polarization (i.e. large % P$_{13C}$ values) of $^{13}$C sites that are three (ortho-position) and four (meta-position, FIG. 14) chemical bonds away from hydride protons (FIG. 11). That previous proof-of-principle work did not address the reasons for low heteronuclear polarization efficiency in the case of $^{14}$N spins that would otherwise be present in such compounds. One part of the explanation is enhanced scalar relaxation of the second kind suffered by the target spins within the micro-Tesla regime, induced by quadrupolar $^{14}$N sites within the scalar coupling network. A second explanation is the absence of a close spin ½ J-coupling network. All-in-all, the data presented in FIG. 20 supports the importance of J-coupling networks for hyperpolarization of $^{13}$C spins too (in addition to the $^{15}$N sites discussed as the primary topic of this work).

In FIG. 20, additional evidence is provided supporting the need for polarization relays in such strongly coupled networks. First, a metronidazole-$^{15}$N$_2$-$^{13}$C$_2$ sample was hyperpolarized via SABRE-SHEATH and para-H$_2$ bubbling was stopped. Next, the sample was rapidly transferred into the 9.4 T NMR spectrometer, and hyperpolarization on the $^{13}$C and $^{1}$H sites was immediately destroyed (by applying a series of 90° RF pulses to $^{13}$C spins and $^{1}$H decoupling to $^{1}$H spins) and a proton-decoupled $^{13}$C spectrum was acquired (FIG. 20A). In a separate experiment (instead of recording $^{13}$C spectrum), the sample was additionally transferred back into the μT field created by the magnetic shield (employed for SABRE-SHEATH polarization in the first step—here employed to re-enable heteronuclear polarization transfer), and $^{13}$C hyperpolarization was indeed re-created (FIG. 20B). Since all $^{13}$C and $^{1}$H sites were depolarized (by broadband irradiation), it is concluded that the only remaining source of polarization for such $^{13}$C re-hyperpolarization is the hyperpolarization pool of $^{15}$N sites. Moreover, the efforts to re-polarize this sample by MFC to the Earth's magnetic field (FIG. 20C) were unsuccessful in comparison to re-hyperpolarization at μT field (FIG. 20B)—further indicating that the source of polarization must be from non-carbon spins.

Broader relevance. Metronidazole is an important potential contrast agent (because high % P$_{15N}$ can be achieved, and it is possible to administer high (~2 g) dose of this potent antibiotic) that can be potentially employed for hypoxia imaging in a manner similar to fluoromisonidazole (FMISO) and other radiolabeled nitroimidazole derivatives used in position emission tomography (PET) imaging. Therefore, this work will certainly be useful for future development and optimization of SABRE-SHEATH hyperpolarization of this and other $^{15}$N and $^{13}$C HP imaging probes.

More generally, the systematic studies presented in this work provide clear experimental evidence that heteronuclear J-coupling spin-½ networks serve as the underlying fundamental basis for efficient relayed polarization transfer from para-H$_2$-derived metal hydrides (FIG. 15) to substrate heteronuclei that do not directly bind to the Iridium complex. Here, we show that efficient hyperpolarization of long-range $^{13}$C and $^{15}$N sites is achieved in SABRE when a network of heteronuclear J-couplings is present. The presence of this network translates to efficient hyperpolarization of many heteronuclei, including $^{13}$C, $^{15}$N, 31P, $^{19}$F, etc. Most importantly, the nitrogen site directly interacting with the iridium hexacoordinate complex should be labeled to create a relay of spin ½ nuclei for efficient polarization transmission deeper within the intramolecular space. Therefore, it is believed that this relayed mechanism opens new opportunities for efficient SABRE hyperpolarization of new biomolecular targets, and informs the rational design of nuclear spin coupling networks in labeled agents for a wide variety of potential biomedical applications. Of note, $^{13}$C labeling did not significantly affect $^{15}$N T$_1$ relaxation: T$_1$($^{15}$N$_3$) is ca. 36 s with (data not shown) and without $^{13}$C spin labeling[14], which is relevant for production of HP contrast agents with long-lived HP states in the context of biomedical applications. As another example, uniformly (or backbone-)$^{13}$C/$^{15}$N labeled peptides and proteins can potentially act as efficient networks of SABRE hyperpolarization, and it may be possible to hyperpolarize isotopically labeled peptides and proteins using this approach. It is also envisioned that isotopically labeled DNA, RNA, and other structures can be hyperpolarized via this SABRE-SHEATH approach. The general concept of relayed polarization transfer through a close J-coupling network will also potentially translate to LIGHT-SABRE and RF-SABRE sequences that create hyperpolarization directly in the magnet and avoid the need for sample transfer.

In the context of SABRE hyperpolarization of proton sites, this work provides experimental evidence in support of relayed polarization transfer. As a result, it would be potentially possible to hyperpolarize long-range proton sites too. While proton-hyperpolarized compounds are rarely used for contrast agents for HP MRI, potential SABRE applications most likely would include analysis of complex mixtures at low concentrations with potential detection of nitrogen- and sulfur-containing heterocycles in oil or refined petroleum products.

Conclusion

Efficient SABRE hyperpolarization of long-range $^{13}$C and $^{15}$N sites was demonstrated in metronidazole-$^{15}$N$_2$-$^{13}$C$_2$ in the μT field regime. The present disclosure shows that long range $^{13}$C and $^{15}$N sites (i.e. three and four chemical bonds away from para-H$_2$-derived hydrides) can be hyperpolarized much more efficiently via a mechanism of relayed spin-polarization transfer than via weak long-range J-couplings. Specifically, the short-range $^{15}$N site, directly bound to Iridium, is hyperpolarized first and hyperpolarization is then transferred/relayed to other intramolecular sites via a network of short-range J-couplings involving further spins. The presented evidence opens new opportunities for SABRE-based hyperpolarization of long range spin-½ nuclei in a wide range of applications ranging from biomedical contrast agents, to analysis of complex mixtures, to structural biology.

Experimental Details

In case of $^{15}$N and $^{13}$C, the thermally polarized signals were generally very low, and therefore, external signal reference was employed. The enhancements were computed as follows:

$$\varepsilon = \frac{S_{HP}}{S_{REF}} \times \frac{C_{REF}}{C_{HP}} \times \frac{A_{REF}}{A_{HP}} \times \frac{N_{REF}}{N_{HP}}$$

where $S_{HP}$ and $S_{REF}$ are NMR signals for HP state and thermally polarized signal reference samples respectively, $C_{REF}$ and $C_{HP}$ are the effective isotope concentrations of thermally polarized signal reference and HP samples respectively, $A_{REF}$ and $A_{HP}$ are the solution cross-section in the NMR tube, and $N_{REF}$ and Hip are the number of symmetrical sites per molecule for the thermally polarized signal reference and HP samples respectively ($A_{REF}/A_{HP}$ was ~1.85 as described earlier). Percentage polarization was computed by multiplying signal enhancement c by the equilibrium nuclear spin polarization of a given spin at 9.4 T and 298K: $3.2 \times 10^{-3}$% ($^1$H), $8.1 \times 10^{-3}$% ($^{13}$C), $3.3 \times 10^{-4}$% ($^{15}$N).

Calculation of SABRE Polarization Enhancement Factors

TABLE 2

Calculations of $^{15}$N signal enhancements and polarization levels (% P). ($N_{REF}/N_{HP} = 2$), ($A_{REF}/A_{HP} = 1.85$)

Figure 14A:
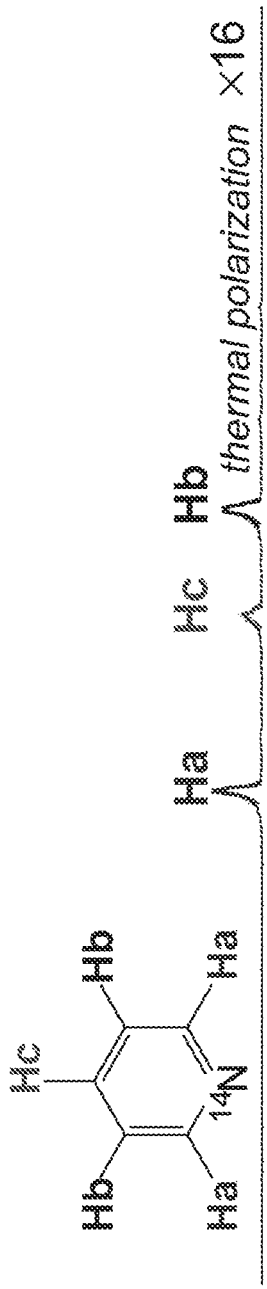
FIGS. 14A-14D: $^1$H NMR spectra of SABRE-hyperpolarized ~100 mM pyridine solutions in methanol-d$_4$. All NMR spectra were recorded using Bruker Avance III 9.4 T NMR spectrometer.

| Imidazole- | FIG. 14A | | |
|---|---|---|---|
| | $^{15}$N$_2$ | $^{15}$N$_3$ (250 ppm) | $^{15}$N$_1$ (165 ppm) |
| Thermal integral | 5488627.17 | | |
| HP integral | | −225970.77 | −4915547.71 |
| Thermal concentration (M) | 8.65 | | |
| HP concentration (M) | | 0.017 | 0.017 |
| Signal enhancement | | 77.5 | 1686.1 |
| % P$_{15N}$ (actual, 50% p-H$_2$) | | ~0.026 | ~0.56 |

TABLE 3

Calculations of $^{15}$N signal enhancements and polarization levels (% P). ($N_{REF}/N_{HP} = 2$), ($A_{REF}/A_{HP} = 1.85$)

Figure 14B:
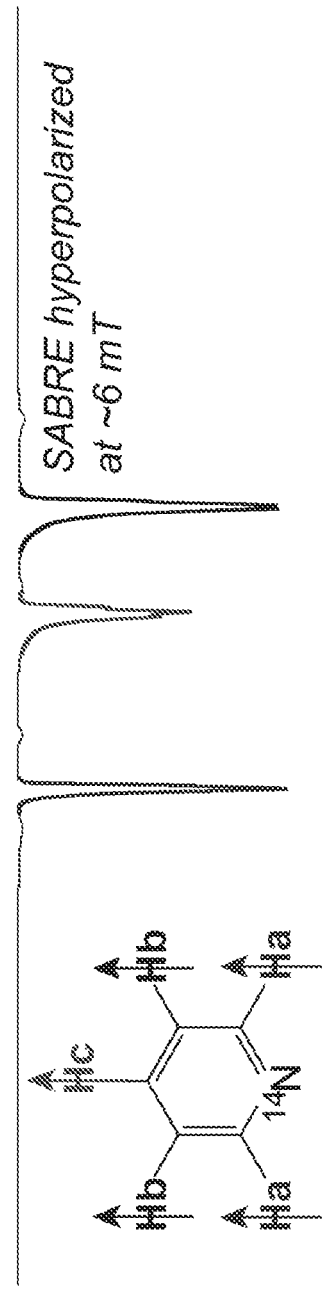

| Imidazole- | FIG. 14B | | |
|---|---|---|---|
| | $^{15}$N$_2$ | $^{15}$N$_3$ (250 ppm) | $^{15}$N$_1$ (165 ppm) |
| Thermal integral | 5488627.17 | | |
| HP integral | | −2355921.23 | −2941133.33 |
| Thermal concentration (M) | 8.65 | | |
| HP concentration (M) | | 0.017 | 0.017 |
| Signal enhancement | | 808.1 | 1008.8 |
| % P$_{15N}$ (actual, 50% p-H$_2$) | | ~0.27 | ~0.33 |

TABLE 4

Calculations of $^{15}$N signal enhancements and polarization levels (% P). ($N_{REF}/N_{HP} = 2$), ($A_{REF}/A_{HP} = 1.85$)

Figure 14C:
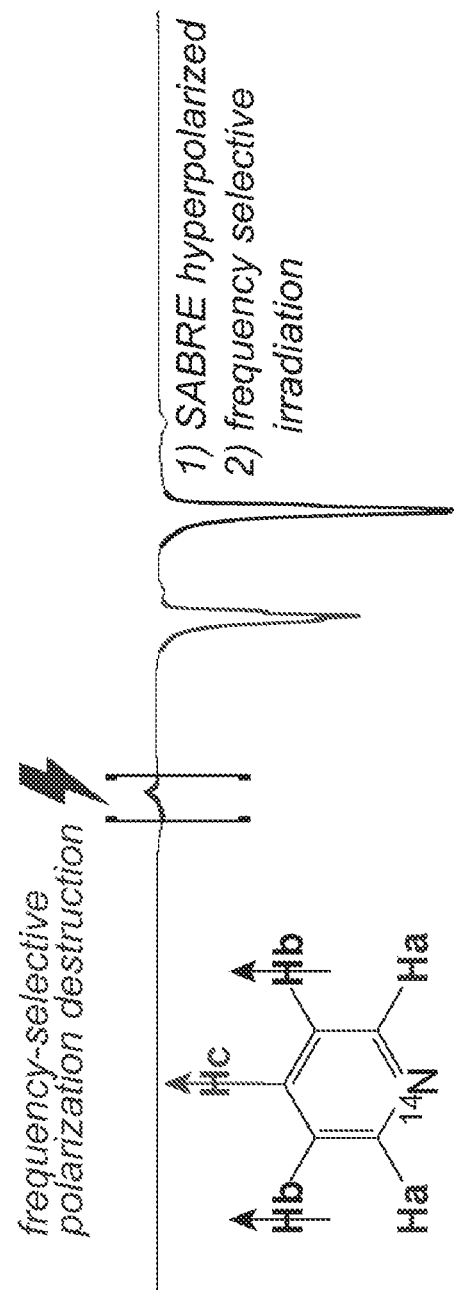

| Imidazole- | FIG. 14C | | |
|---|---|---|---|
| | $^{15}$N$_2$ | $^{15}$N$_3$ (250 ppm) | $^{15}$N$_1$ (165 ppm) |
| Thermal integral | 5488627.17 | | |
| HP integral | | −659067.25 | −437363.88 |
| Thermal concentration (M) | 8.65 | | |
| HP concentration (M) | | 0.017 | 0.017 |
| Signal enhancement | | 226.1 | 150.0 |
| % P$_{15N}$ (actual, 50% p-H$_2$) | | ~0.074 | ~0.049 |

TABLE 5

Calculations of $^{15}$N signal enhancements and polarization levels (% P). ($N_{REF}/N_{HP} = 2$), ($A_{REF}/A_{HP} = 1.85$)

Figure 14D:
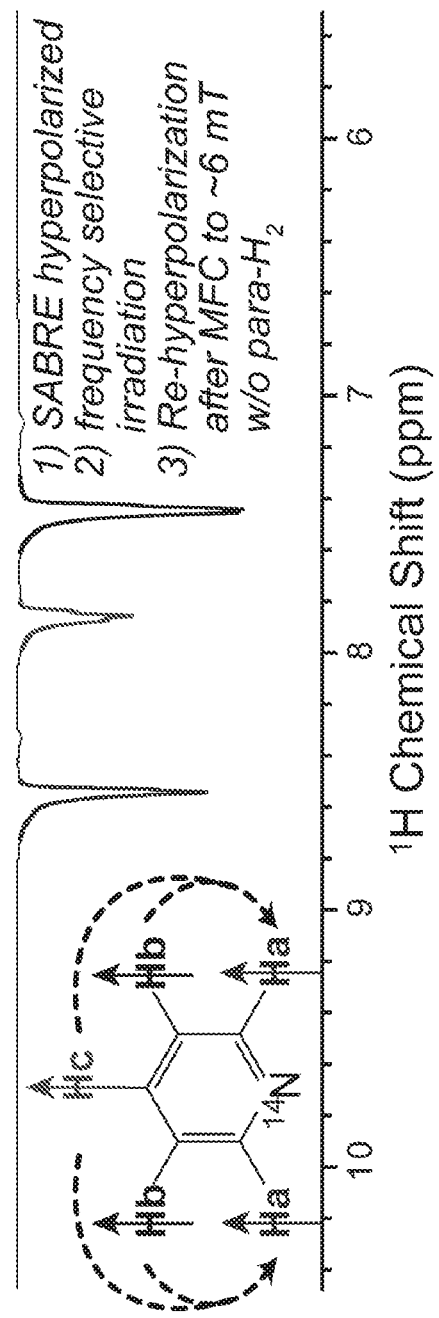

| Imidazole- | FIG. 14D | | |
|---|---|---|---|
| | $^{15}$N$_2$ | $^{15}$N$_3$ (250 ppm) | $^{15}$N$_1$ (165 ppm) |
| Thermal integral | 5488627.17 | | |
| HP integral | | N/A | 3967289.48 |
| Thermal concentration (M) | 8.65 | | |
| HP concentration (M) | | N/A | 0.017 |
| Signal enhancement | | N/A | 1360.8 |
| % P$_{15N}$ (actual, 50% p-H$_2$) | | N/A | ~0.45 |

TABLE 6

Calculations of $^{15}$N signal enhancements and polarization levels (% P). ($N_{REF}/N_{HP} = 2$), ($A_{REF}/A_{HP} = 1.85$)

| Imidazole- | FIG. 14E | | |
|---|---|---|---|
| | $^{15}$N$_2$ | $^{15}$N$_3$ (250 ppm) | $^{15}$N$_1$ (165 ppm) |
| Thermal integral | 5488627.17 | | |
| HP integral | | 1348548.76 | 2050438.36 |
| Thermal concentration (M) | 8.65 | | |
| HP concentration (M) | | 0.017 | 0.017 |
| Signal enhancement | | 462.6 | 703.3 |
| % P$_{15N}$ (actual, 50% p-H$_2$) | | ~0.15 | ~0.23 |

TABLE 7

Calculations of $^{15}$N signal enhancements and polarization levels (% P). ($N_{REF}/N_{HP} = 2$), ($A_{REF}/A_{HP} = 1.85$)

| Imidazole- | FIG. 16A | | |
|---|---|---|---|
| | $^{15}$N$_2$ | $^{15}$N$_3$ (250 ppm) | $^{15}$N$_1$ (165 ppm) |
| Thermal integral | 5488627.17 | | |
| HP integral | | −6084201.09 | −83444.91 |
| Thermal concentration (M) | 8.65 | | |
| HP concentration (M) | | 0.017 | 0.017 |
| Signal enhancement | | 2086.9 | 28.6 |
| % P$_{15N}$ (actual, 50% p-H$_2$) | | ~0.69 | ~0.0095 |

TABLE 8

Calculations of $^{15}$N signal enhancements and polarization levels (% P). ($N_{REF}/N_{HP} = 2$), ($A_{REF}/A_{HP} = 1.85$)

| | Imidazole- | FIG. 16B | |
|---|---|---|---|
| | $^{15}N_2$ | $^{15}N_3$ (250 ppm) | $^{15}N_1$ (165 ppm) |
| Thermal integral | 5488627.17 | | |
| HP integral | | −3249591.01 | −2621929.88 |
| Thermal concentration (M) | 8.65 | | |
| HP concentration (M) | | 0.017 | 0.017 |
| Signal enhancement | | 1114.6 | 899.3 |
| % $P_{15N}$ (actual, 50% p-H$_2$) | | ~0.37 | ~0.30 |

TABLE 9

Calculations of $^{15}$N signal enhancements and polarization levels (% P). ($N_{REF}/N_{HP} = 2$), ($A_{REF}/A_{HP} = 1.85$)

| | Imidazole- | FIG. 16C | |
|---|---|---|---|
| | $^{15}N_2$ | $^{15}N_3$ (250 ppm) | $^{15}N_1$ (165 ppm) |
| Thermal integral | 5488627.17 | | |
| HP integral | | 3767501.13 | N/A |
| Thermal concentration (M) | 8.65 | | |
| HP concentration (M) | | 0.017 | 0.017 |
| Signal enhancement | | 1292.3 | N/A |
| % $P_{15N}$ (actual, 50% p-H$_2$) | | ~0.42 | N/A |

TABLE 10

Calculations of $^{15}$N signal enhancements and polarization levels (% P). ($N_{REF}/N_{HP} = 2$), ($A_{REF}/A_{HP} = 1.85$)

| | Imidazole- | FIG. 16D | |
|---|---|---|---|
| | $^{15}N_2$ | $^{15}N_3$ (250 ppm) | $^{15}N_1$ (165 ppm) |
| Thermal integral | 5488627.17 | | |
| HP integral | | 2055713.90 | 1510532.96 |
| Thermal concentration (M) | 8.65 | | |
| HP concentration (M) | | 0.017 | 0.017 |
| Signal enhancement | | 705.1 | 518.1 |
| % $P_{15N}$ (actual, 50% p-H$_2$) | | ~0.23 | ~0.17 |

TABLE 11

Calculations of $^{13}$C signal enhancements and polarization levels (% P). ($N_{REF}/N_{HP} = 1$), ($A_{REF}/A_{HP} = 1.85$)

| | Sodium | FIG. 18A | |
|---|---|---|---|
| | Acetate-1-$^{13}$C | $^{13}$C (150 ppm) | $^{13}$C (12 ppm) |
| Thermal integral | 68630977.57 | | |
| HP integral | | 142039.83 | 1306385.89 |
| Thermal concentration (M) | 2.03 | | |
| HP concentration (M) | | 0.017 | 0.017 |
| Signal enhancement | | N/A | N/A |
| % $P_{13C}$ (actual, 50% p-H$_2$) | | N/A | N/A |

TABLE 12

Calculations of $^{13}$C signal enhancements and polarization levels (% P). ($N_{REF}/N_{HP} = 1$), ($A_{REF}/A_{HP} = 1.85$)

| | Sodium | FIG. 18B | |
|---|---|---|---|
| | Acetate-1-$^{13}$C | $^{13}$C (150 ppm) | $^{13}$C (12 ppm) |
| Thermal integral | 68630977.57 | | |
| HP integral | | 96323096.62 | 76051902.66 |
| Thermal concentration (M) | 2.03 | | |
| HP concentration (M) | | 0.017 | 0.017 |
| Signal enhancement | | 311.7 | 246.1 |
| % $P_{13C}$ (actual, 50% p-H$_2$) | | ~0.252 | ~0.20 |

TABLE 13

Calculations of $^{13}$C signal enhancements and polarization levels (% P). ($N_{REF}/N_{HP} = 1$), ($A_{REF}/A_{HP} = 1.85$)

| | Sodium | FIG. 18C | |
|---|---|---|---|
| | Acetate-1-$^{13}$C | $^{13}$C (150 ppm) | $^{13}$C (12 ppm) |
| Thermal integral | 68630977.57 | | |
| HP integral | | −4944073.97 | 785712.82 |
| Thermal concentration (M) | 2.03 | | |
| HP concentration (M) | | 0.017 | 0.017 |
| Signal enhancement | | 16.0 | 2.5 |
| % $P_{13C}$ (actual, 50% p-H$_2$) | | ~0.0129 | ~0.0020 |

Example 4 Long-Lived $^{13}C_2$ Nuclear Spin States Hyperpolarized by Parahydrogen in Reversible Exchange at Micro-Tesla Fields Parahydrogen is an inexpensive and readily available source of hyperpolarization used to enhance magnetic resonance signals by up to 4 orders of magnitude above thermal signals obtained at ~10 T. A significant challenge for applications is fast signal decay after hyperpolarization. In some embodiments, parahydrogen based polarization transfer catalysis at micro-Tesla fields (first introduced as SABRE-SHEATH) is used to hyperpolarize $^{13}C_2$ spin pairs and find decay time constants of 12 s for magnetization at 0.3 mT, which are extended to 2 minutes at that same field, when long-lived singlet states are hyperpolarized instead. Enhancements over thermal at 8.5 T are between 30 and 170 fold (0.02% to 0.12% polarization). The present method may include controlling the spin dynamics of polarization transfer by choice of μT field allowing for deliberate hyperpolarization of either magnetization or long-lived singlet states. Density functional theory (DFT) calculations and experimental evidence identify two energetically close mechanisms for polarization transfer: first, a model that involves direct binding of the $^{13}C_2$ pair to the polarization transfer catalyst (PTC), and second, a model transferring polarization through auxiliary protons in substrates.

Nuclear spin hyperpolarization is an intriguing research area, because of its ability to enhance nuclear magnetic resonance (NMR) and magnetic resonance imaging (MRI) signals by multiple orders of magnitude. Hyperpolarization methods are particularly useful if they can enhance signals from heteronuclei such as $^{13}$C or $^{15}$N because they can be installed in a wide range of biomolecules, and they retain hyperpolarization on extended timescales. At the same time, hyperpolarization of protons also has particular advantages, which stem from higher sensitivity and 100% natural abundance. A particularly simple hyperpolarization technique is para-H$_2$ induced polarization (PHIP). Especially, when implemented as Signal Amplification By Reversible Exchange (SABRE) it allows for continuous and rapid hyperpolarization directly in solutions. In the SABRE procedure, para-H$_2$ and the target (i.e. to-be-hyperpolarized) molecules bind reversibly with an iridium-based hexacoordinate catalyst. At specific magnetic fields, polarization will transfer from para-H$_2$ to spins on the target molecule driven by J-coupling interactions, for example ~6.5 mT is ideal to hyperpolarize proton spins. On the other hand, heteronuclei (e.g. $^{15}$N, $^{31}$P, $^{13}$C) are best magnetized in microTesla fields established in magnetically shielded environments, an approach that was coined SABRE-SHEATH (SABRE in Shield Enable Alignment Transfer to Heteronuclei).

However, if the goal is to hyperpolarize long-lived singlet states, the picture changes slightly because the conditions for the transfer of scalar order have a different field dependence. For example, it has been shown that the singlet state of the $^{15}$N$_2$ spin pair of diazirines is hyperpolarized over a relatively wide range of magnetic fields between a few µT to about 100 mT. These hyperpolarized nuclear spin singlet states of $^{15}$N$_2$ diazirines display relaxation time constants of above 20 minutes. Similarly, SABRE was used to hyperpolarize long-lived singlet states on $^1$H$_2$-pairs, where polarization decay time constants of above 4 min were observed. Such long hyperpolarization lifetime promises biomolecular tracking and imaging of low concentration analytes on significantly extended timescales. In this article, we use SABRE-SHEATH, to hyperpolarize magnetization as well as long-lived nuclear singlet states in carbon-13 spin pairs and find lifetime T$_1$ of 12 s for magnetization and T$_S$ of 2 min for long-lived singlet states at 0.3 mT. Here it is important to note, that the current record of a long-lived singlet state is held by a $^{13}$C$_2$ spin pair (hyperpolarized by DNP, not SABRE) with lifetime, T$_S$, of more than one hour.

In some embodiments, for the presented experiments, two molecules with various isotopic labeling schemes are designed. For example, 1,2-(4-pyridyl) acetylene (with symmetric structure) and 1-phenyl-2-(4-pyridyl) acetylene (with asymmetric structure) are synthesized herein. For both, the present method may include isotopomers with naturally abundant $^{13}$C, as well as doubly $^{13}$C labeled substrates at the triple bond. The results presented in FIG. 23 indicate that the acetylene carbon spins as well as the aromatic bridge carbon spins are hyperpolarized. The enhancements are between 30 to 170 fold (0.02% to 0.12% polarization), when compared to thermal signals acquired at 8.45 T. The molecules with $^{13}$C at natural abundance show 2-3 times higher enhancements compared to $^{13}$C enriched sites. This is likely due to faster T$_1$ relaxation in $^{13}$C$_2$ pairs as opposed to T$_1$ of isolated $^{13}$C spins. An additional cause may simply be the higher ratio of polarization source (p-H$_2$) to target spins in the naturally abundant case.

The hyperpolarization transfer from para-H$_2$ to these substrates occurs via iridium based polarization transfer catalysts (PTC's). In some embodiments, the standard precatalyst [IrCl(IMes)(COD)], (IMes=1,3-bis(2,4,6-trimethylphenyl)imidazole-2-ylidene; COD=cyclooctadiene) may be used. The present method may be carried out using substrate concentrations of 30 mM or 160 mM, and catalyst concentrations of 2 mM or 10 mM for the symmetric and asymmetric compounds respectively. The solvent was methanol-d$_4$, and the precatalyst was activated by bubbling para-H$_2$ through the sample for 15 minutes at a pressure of 7 bar and a fractional parahydrogen enrichment of ~85%. Thereafter, hyperpolarization was performed according to the SABRE-SHEATH procedure: the sample is exposed to para-H$_2$ in a magnetically shielded environment outfitted with a small solenoid coil to obtain a controllable µT magnetic field. One minute of exposure to para-H$_2$ is sufficient to equilibrate polarization. Subsequently, the sample is transferred manually as quickly as possible (~8 s) to a Bruker 360 MHz (8.45 T) magnet for read out. The manual transfer time of 8 s is relatively consistent, with variations of ~1 s.

The polarization transfer occurs in catalytically active PTC's. Two possible, energetically low PTC species are depicted in FIG. 24. The ground state energies were determined by density functional theory calculations using the all-electron FHI-aims code. The geometries were optimized using the PBE parameterization of exchange and correlation with a van der Waals correction and the tier 2 basis sets. Scalar relativity was handled in the atomic ZORA approximation. Additional possible configurations and the corresponding PTC-energy landscape are provided. Furthermore, also provided are $^1$H-NMR spectra of the hyperpolarized hydrides bound to the Iridium center demonstrating the presence of at least two catalytic species. In this first study, hyperpolarized $^{13}$C signals from molecules bound to the Iridium molecules were not detected. Therefore, more indirect evidence coupled with ab initio calculations are used to determine likely PTC structures.

In the first PTC model (FIG. 24A), all substrate molecules bind to the Ir center via nitrogen. This is the energetically lowest PTC species identified by us. Here, polarization transfers from para-H$_2$ to the pyridyl protons first and finally arrives at the acetylenic carbons. In the second PTC model (FIG. 24B), the catalyst binds with the triple bond and polarization is transferred directly to $^{13}$C sites.

The spectra displayed in FIG. 23 could quickly lead to the conclusion, that the active PTC must be the directly binding model (FIG. 24B), because hyperpolarization from the ring carbons are not observed, other than from those in the bridge to the acetylene bond. Moreover, hydrogenation is observed, which most certainly requires binding of the triple bond to the iridium center. Hydrogenation rates depend on the ratio of substrate to catalyst: at 3:1 hydrogenation completes in less than 30 minutes, however at above 15:1, hydrogenation takes more than 12 h. In a single SABRE experiment (with 1 min of bubbling) it was estimated that significantly less than 1% hydrogenation at the 15:1 ratio may occur, which was used for most experiments. Hyperpolarized hydrogenation products are observed, which display typical ALTADENA type enhancements due to incorporation of para-Hz (spectra provided in the SI). Still, it is hypothesized that that the spectra displayed in FIG. 23 all result from SABRE as they are uniquely associated with the intact, non-hydrogenated substrates.

Additional observations are made. First, the PTC on of FIG. 24A is energetically lower. Furthermore, all non-detected $^{13}$C spins are directly bound to protons. This leads to much faster $^{13}$C relaxation (a typical T$_1$ relaxation time for aromatic $^{13}$C directly bound to a proton is ~5 s, whereas T$_1$ relaxation constants of the bridge carbons are found to be 11(1) s and T$_1$ of the acetylenic carbons is 12(0.5) s at low fields) with two important consequences. First, the hyperpolarization buildup at these $^{13}$C sites will be much less efficient, and second, a small amount of hyperpolarization may quickly relax during the ~8 s sample transfer from polarization region into the magnet. In addition, SABRE under optimized condition for $^1$H polarization transfer at 6.5 mT was performed, which resulted in strong enhancement of the pyridyl ring protons, while enhancement of $^{13}$C were negligible and $^1$H enhancements on the distant phenyl ring were much smaller. Though bound species were not observed from the $^{13}$C spectra, the hydride peaks were observed. For example, a small chemical shift difference of the hydride peaks was observed (~0.2 ppm, which would be much larger for the binding mode in FIG. 24B based on DFT calculation). Finally, hyperpolarization of diphenyl-$^{13}$C$_2$-acetylene (no ring nitrogens) in the SABRE-SHEATH mode was tested and did not result in measurable enhancements. All these considerations point to a strong contribution of the PTC shown in FIG. 24A.

To investigate this in more detail, a careful characterization of hyperpolarization transfer as function of micro-Tesla field was performed using the doubly $^{13}$C labeled molecules. As depicted in FIG. 25, the magnetic field was varied between −12 and +12 μT, accompanied by simulations of the hyperpolarization transfer process.

Importantly, the present method allows one to directly choose to polarize different states of the $^{13}$C pair: magnetization or singlet, which are easily distinguishable by their spectra. Magnetization is easily detected from both molecules (FIG. 25A panel (1), FIG. 25B panel (1)), whereas singlet-order can only be detected immediately from the asymmetric 1-phenyl-2-(4-pyridyl) acetylene because the acetylenic carbons have a chemical shift difference (FIG. 23C). For this asymmetric compound, the acetylenic carbons are strongly coupled at low fields ($J_{CC}$ is ~185 Hz, whereas their chemical shift difference $\Delta v_C$ is less than 0.5 mHz). Upon transfer to the high field in the magnet (8.45 T) for read out, the chemical shift difference becomes significantly larger than the $J_{CC}$ coupling ($\Delta v_C$~770 Hz), the carbons are now weakly coupled, and the singlet state is no longer an eigenstate. The sample transfer from low to high field transforms $I_1 \cdot I_2$ singlet order into detectable $(I_{1z}-I_{2z})$ which gives antiphase signals in a pulse acquire experiment, as shown in FIG. 25B panel (4). However, for the symmetric molecule, since the two carbons will remain symmetric at high field, the singlet state cannot be accessed immediately. In principle, access to the singlet can be accomplished by specialized pulse sequences such as singlet-to-magnetization (S2M) or SLIC.

In order to understand the polarization transfer dynamics at micro-Tesla fields in detail, resonance conditions dictated by the Hamiltonian of the doubly $^{13}$C labeled molecule are considered. At low fields of <0.6 μT, we encounter a resonance condition to polarize magnetization, given as $$|v_H - v_C| = \pm J_{HH}, \quad (Eq. 1)$$

where $v_H$ and $v_C$ are the frequencies of protons and carbons and $J_{HH}$ is the J-coupling between the two para-H$_2$ derived hydrides on the iridium. When solved for the magnetic field using $v = -\gamma B$ the magnetization transfer field is obtained as $$B_{trans} = J_{HH}/(\gamma_H - \gamma_C), \quad (Eq. 2)$$

where $\gamma_H$=42.577 Hz/μT and $\gamma_C$=10.705 Hz/μT. When the field is increased to a few μT, additional resonance conditions to create magnetization and/or singlet are encountered. The Hamiltonian reveals overlapping conditions to create magnetization and singlet given as $$|v_H - v_C| = \pm (J_{CC} \pm J_{HH}), \quad (Eq. 3)$$

where $J_{CC}$ is the acetylenic $^{13}$C J-coupling. Again, solving for the transfer field the following is obtained:

$$B_{trans} = \pm (J_{CC} \pm J_{HH})/(\gamma_H - \gamma_C) \quad (Eq. 4)$$

Equations (1,2) and (3,4) fully encompass the behavior observed in FIG. 25. In the low field region, maximum magnetization transfer is observed at ~±0.34(0.1) μT, whereas there is negligible singlet buildup. At slightly elevated fields, both magnetization and singlet have local maxima/minima at ~±5.6(0.2) μT and ~±6.4(0.2) μT (see FIG. 25B). These values are consistent with Jim ~10(3) Hz, and $J_{CC}$~190(5) Hz. $J_{CC}$ can also be estimated from the hyperpolarized NMR spectrum of the free form where we find $J_{CC}$=185 Hz (see FIG. 23D).

By numerical simulations of the spin dynamics we confirm that the general behavior is largely independent of the polarization transfer mechanism (direct to $^{13}$C$_2$ (FIG. 24B) vs. indirect via auxiliary protons (FIG. 24A)). However, the numerical value of $J_{CC}$ strongly depends on the exact nature of the PTC. First principles calculations of the relevant J-couplings are performed using the FHI-aims code. The PBE parameterization for exchange and correlation and the fully uncontracted cc-Pv5Z basis sets (tier 2 for iridium) are used. The ab initio calculations predict a $J_{CC}$ of =191 Hz for substrate bound via nitrogen (FIG. 24A) vs. a $J_{CC}$ of 120 Hz for substrate bound directly via the acetylenic bond. Based on the measurements shown in FIG. 25, it is concluded with more confidence that the primary PTC is the energetically favored species shown in FIG. 24A because for the PTC in FIG. 24B we would expect efficient hyperpolarization at significantly lower fields of 3.5±0.3 μT, which is not observed.

Figure 26:
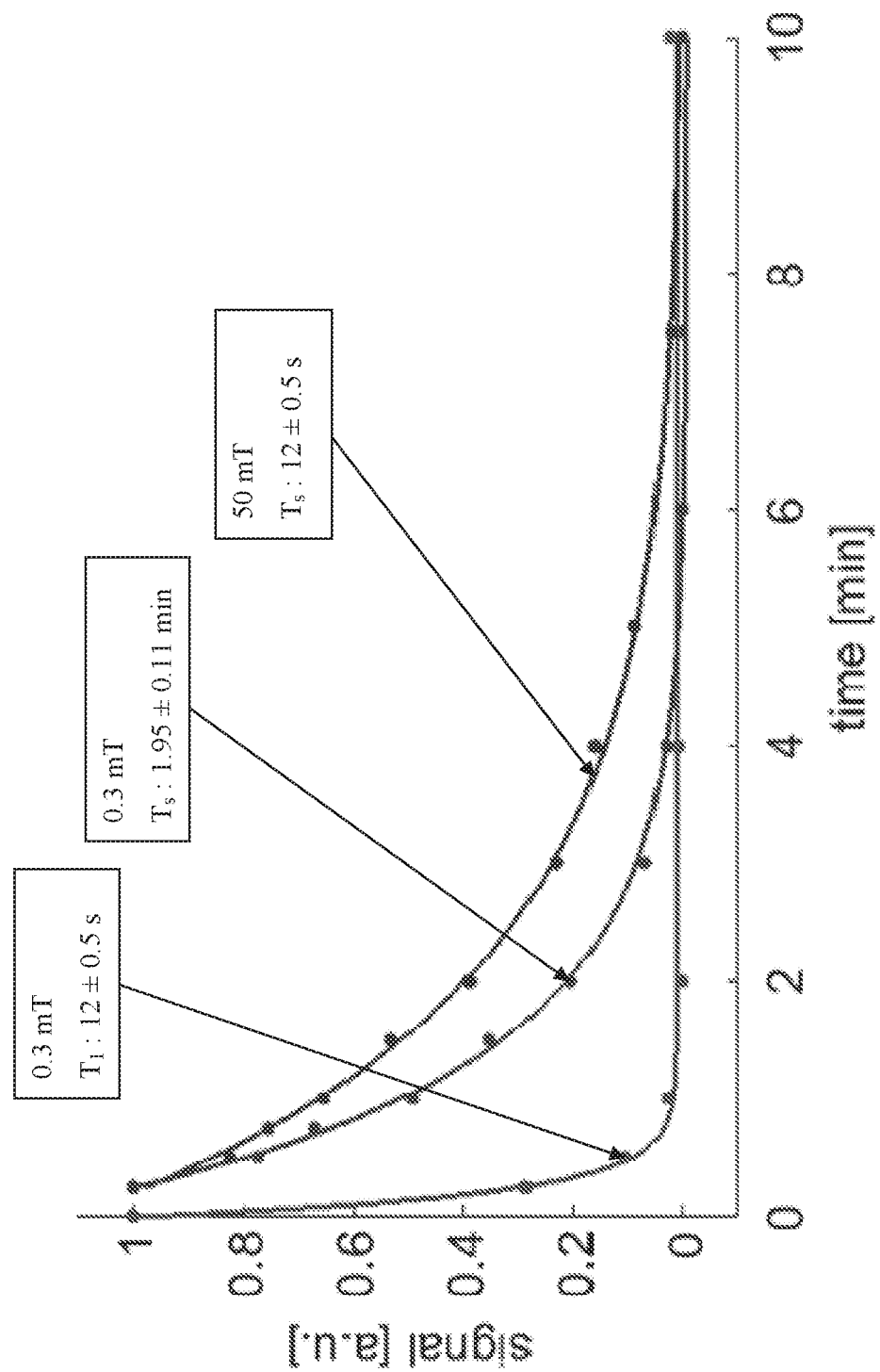
FIG. 26 shows $T_1$ and $T_S$ measurements of 1-phenyl-2-(4-pyridyl) acetylene. For all measurements, the sample was first hyperpolarized in the shield using 0.4 μT (polarize magnetization)/6 μT (polarize singlet order) then positioned at 0.3 mT or 50 mT. After varying delay times the sample was transferred to the magnet quickly to measure the remaining signal. The data points were sampled randomly to eliminate the effect of the slow triple bond hydrogenation, and the lifetime constants were obtained using single exponential fit.

Finally, since the asymmetric molecule allows for easy read out of, both, singlet state and magnetization, their lifetimes $T_S$ or $T_1$ can be measured. As displayed in FIG. 26, $T_S$ is measured at 0.3 mT and 50 mT, and is fit with exponential decay constants of 117(7) s and 69(4) s respectively. For comparison, $T_1$ is measured at the field where it has longer $T_S$ (0.3 mT), and it is found that magnetization decays much more rapidly with exponential decay constant $T_1$ of 12(0.5) s. The $T_1$ lifetime of the $^{13}$C$_2$ pair at 8.45 T is measured as 8(0.4) s.

In conclusion, it is demonstrated that, both magnetization and long-lived singlet order can be induced on $^{13}$C$_2$ using SABRE-SHEATH. Hyperpolarization lifetime is extended to ~2 minutes, or 10 times $T_1$. Furthermore, also disclosed herein is direct hyperpolarization of long-lived singlet order by SABRE-SHEATH when the J-coupling in the targeted spin pair is much larger than the $J_{HH}$ coupling between the hydrides. This is in contrast to the first demonstration, of heteronuclear ($^{15}$N$_2$) long-lived states hyperpolarized by SABRE, where $J_{NN}$ and $J_{HH}$ were comparable in size leading to a resonance condition that is matched at a broad range of fields, raising the question if long-lived states could be hyperpolarized when $J_{NN}$ or $J_{CC}$ are much larger. It has been shown herein that specific μT-fields work in that case. Hyperpolarization levels and enhancements remained relatively low in this first demonstration. It is hypothesized that the quadrupolar $^{14}$N nuclei are the cause of the observed low hyperpolarization level, in view of the finding that quadrupoles act as highly efficient polarization sinks at μT fields. Therefore, hyperpolarization may be boosted, for example, by additional $^{15}$N labeling of the substrates and other strategies detailed in the literature. Overall, the presented results illustrate an avenue towards simple and fast hyperpolarization of long-lived $^{13}$C hyperpolarization with potential applications in biomolecular MRI or the observation of slower processes by hyperpolarized NMR. The presented advances can be translated to biomolecules already shown to be amenable to heteronuclear SABRE hyperpolarization including nicotinamide, in vivo pH sensor imidazole, hypoxia sensor metronidazole and others. While the current work was performed in methanol solutions, recent advances in heterogeneous and water-soluble SABRE catalysis may lead to in vivo translation of the presented approach for fast hyperpolarization of long-lived $^{13}C$ molecular probes.

Experimental Details

Synthesis of the Substrate Molecules

All reactions were performed under a dry argon atmosphere. Tetrahydrofuran (THF) and Diisopropylamine (DIPA) were degassed under reduced pressure. Iodobenzene, Copper iodide, TMS-acetylene-$^{13}C_2$, TMS-acetylene, TBAF 1M in THY were purchased from Sigma Aldrich, Bis(triphenylphosphine)palladium(II) dichloride was purchased from Acros and 4-iodopyridine was purchased from AK Scientific. All purchased chemicals were used without further purification. Reactions were monitored by TLC on silica gel aluminum-backed plates.

Bis(triphenylphosphine)palladium(II) dichloride (14.4 mg, 0.0206 mmol), copper iodide (8.86 mg, 0.0465 mmol) and 4-iodopyridine (0.15490 g, 0.7178 mmol) were added into a 25 mL glass tube and degassed for 1 h under reduced pressure. Then, THP-DIPA (2:1 v/v, 7 mL) was added to dissolve them and TMS-acetylene-$^{13}C_2$ (107.5 μL, 0.7084 mmol) was slowly added. The mixture was stirred at 50° C. for 24 h. After cooling reaction mixture at room temperature, TBAF 1M in THF (1 mL, 1 mmol) was added and stirred at room temperature for 10 min. Next, iodobenzene (0.4 mL, 3.574 mmol) was added and the mixture was stirred at 50° C. for 26 h. The mixture was concentrated and the residue was isolated by extractive work-up with $CH_2Cl_2$-brine. The combined organic phase was dried using anhydrous $Na_2SO_4$ and concentrated. Flash column chromatography was performed using 100% ethyl acetate and yielded 4-(phenylethynyl-1,2-$^{13}C_2$)pyridine (0.1172 g, 0.6468 mmol, 91.3%).

Bis(triphenylphosphine)palladium(II) dichloride (8.62 mg, 0.01228 mmol), copper iodide (11.89 mg, 0.0624 mmol) and 4-iodopyridine (0.4032 g, 1.967 mmol) were added into a 10 mL glass tube and degassed for 1 h under reduced pressure. Then, THP-DIPA (4:1 v/v, 4.5 mL) was added to dissolve them and TMS-acetylene-$^{13}C_2$ (110 μL, 0.7124 mmol) was slowly added. The mixture was stirred at 70° C. for 23 h. After cooling reaction mixture at room temperature, TBAF 1M in THY (1 mL, 1 mmol) was added and the mixture was stirred at 70° C. for 20 h. Extractive work-up ($CH_2Cl_2$-brine) was followed by concentration. The combined organic phase was dried using anhydrous $Na_2SO_4$ and concentrated. Flash column chromatography was performed using 100% ethyl acetate and yielded 1,2-di(pyridin-4-yl)ethyne-1,2-$^{13}C_2$ (0.1054 g, 0.578 mmol, 81.2%).

Polarization of the $^{13}C$ Due to Hydrogenation

Figures 27A, 27B:
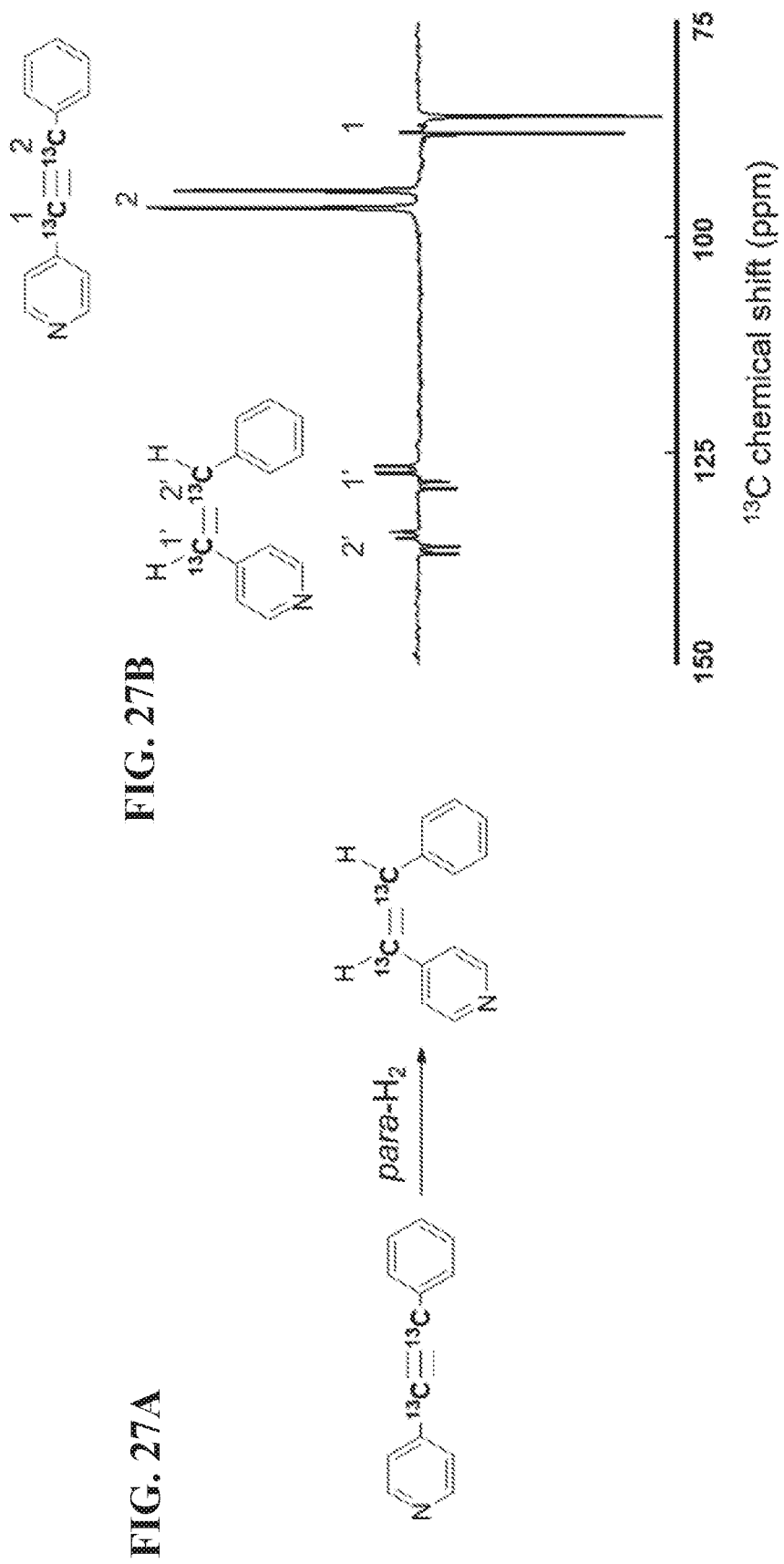
FIGS. 27A and 27B show hydrogenation of the acetylenic triple bond (FIG. 27A) and spectrum of $^{13}C$ hyperpolarization in the shield at 62 mG (FIG. 27B). On the right part of the spectrum around 90 ppm, is the SABRE hyperpolarized singlet of the original substrate. However, a fraction of the substrate (~10%) is hydrogenated and generates the polarization induced by para-$H_2$ addition. Here the ALTADENA effect is observed at the chemical shift of $^{13}C$ around 130 ppm.

Though the substrates are relatively stable during the SABRE-SHEATH experiments, after long time of para-$H_2$ bubbling, hydrogenation happens for the acetylenic triple bond and para-$H_2$ induced polarization (PHIP) is observed. In our case, since the para-$H_2$ is bubbled at a low field in the magnetic shield (62 mG), the hydrogenated $^{13}C$ spin pair will remain in its singlet state until transferred to the magnet for read out. This polarization effect particularly matches the ALTADENA (Adiabatic Longitudinal Transport After Dissociation Engenders Net Alignment) phenomenon, the spectrum is shown FIG. 27.

Thermal and Hyperpolarized $^1H$ Spectra Including the Hydride Region

Figure 28B:
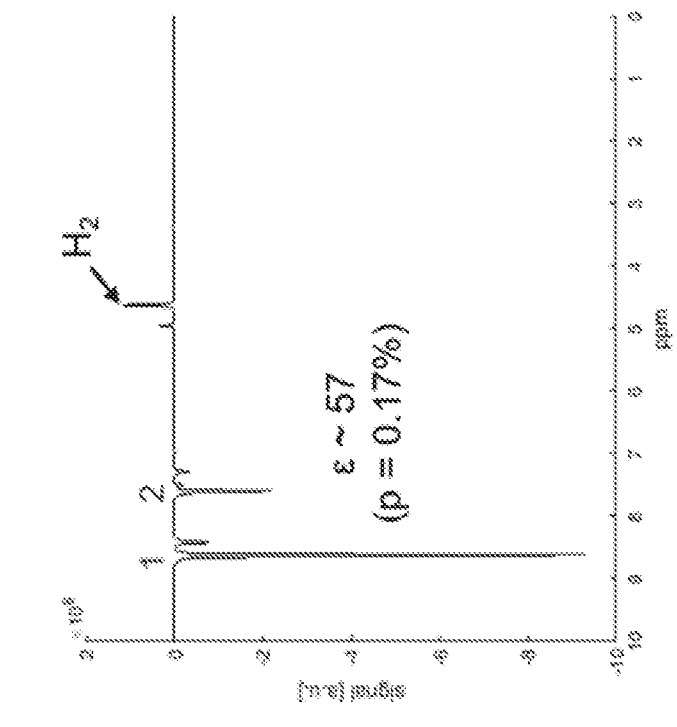
FIG. 28B shows hyperpolarized (SABRE) $^1H$ spectrum. para-$H_2$ is bubbled through the sample at 6.5 mT, a ~57 fold enhancement of positions 1 and 2 protons is obtained. However, positions 3, 4 and 5 are not enhanced.
Figure 28A:
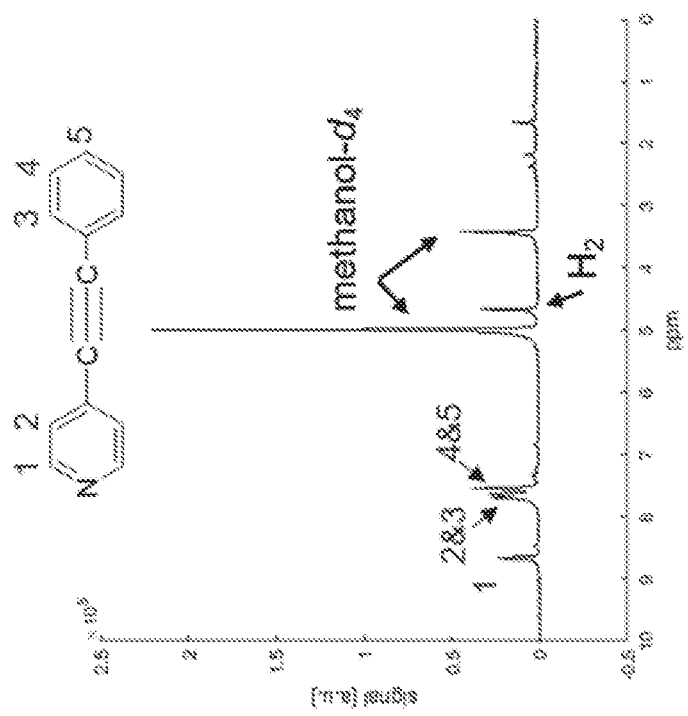
FIG. 28A shows thermal $^1H$ spectrum of the asymmetric molecule and its peak assignment, note that protons on position 2 and 3 overlap. (Position 3 protons have slightly higher chemical shift than protons in position 2).
Figure 28C:
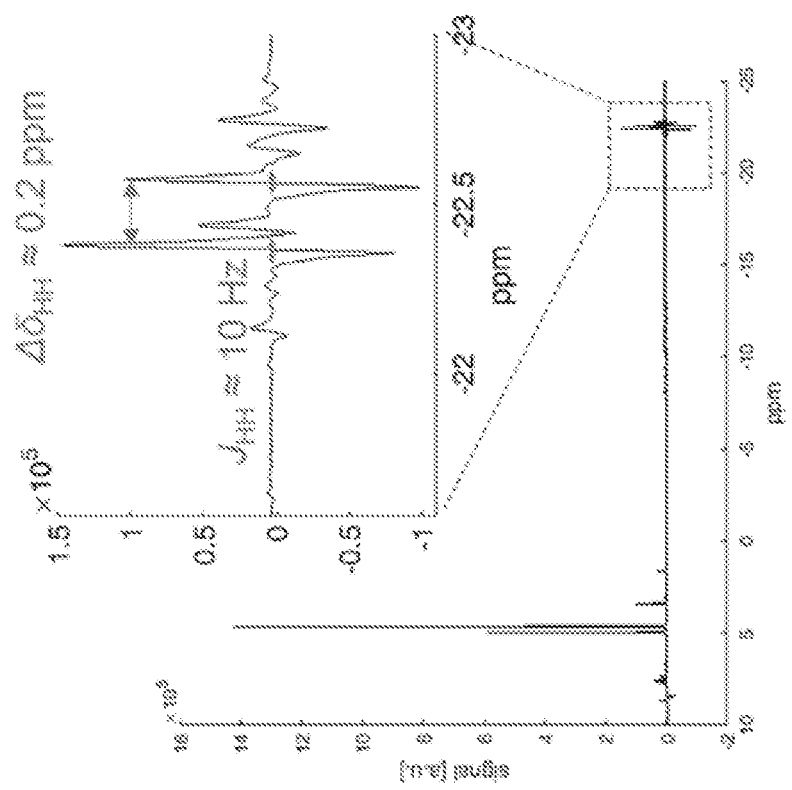
FIG. 28C shows spectrum acquired using 45° pulse immediately after stopping bubbling inside the magnet. The hydrides are observed and there are two major resonances with chemical shift difference around 0.2 ppm, as well as clear indications of minor species.

Thermal and hyperpolarized $^1H$ spectra shown in FIG. 28 were measured to help determine the polarization transfer complex. We used asymmetric substrate with 13C at natural abundance, bubble para-$H_2$ through the hyperpolarization mixture inside the magnet at 8.45 T. A 45° pulse is applied for read out right after stopping the bubbling. The classical PASADENA effect is expected on the hydrides, which is best observed using a 45° pulse.

The $^1H$ spectra assist in the structure determination of the PTC species. As shown in FIG. 28B, only the protons on the pyridyl ring are significantly hyperpolarized with enhanced $^1H$ signal. Clearly identifying a strong contribution of the N-binding model. The hydride region shows that in addition to a principle species, additional complexes exist in solution consistent with the fact that we observe SABRE as well as PHIP via hydrogenation.

Thermal and Hyperpolarized $^{13}C$ Spectra

Figure 29A:
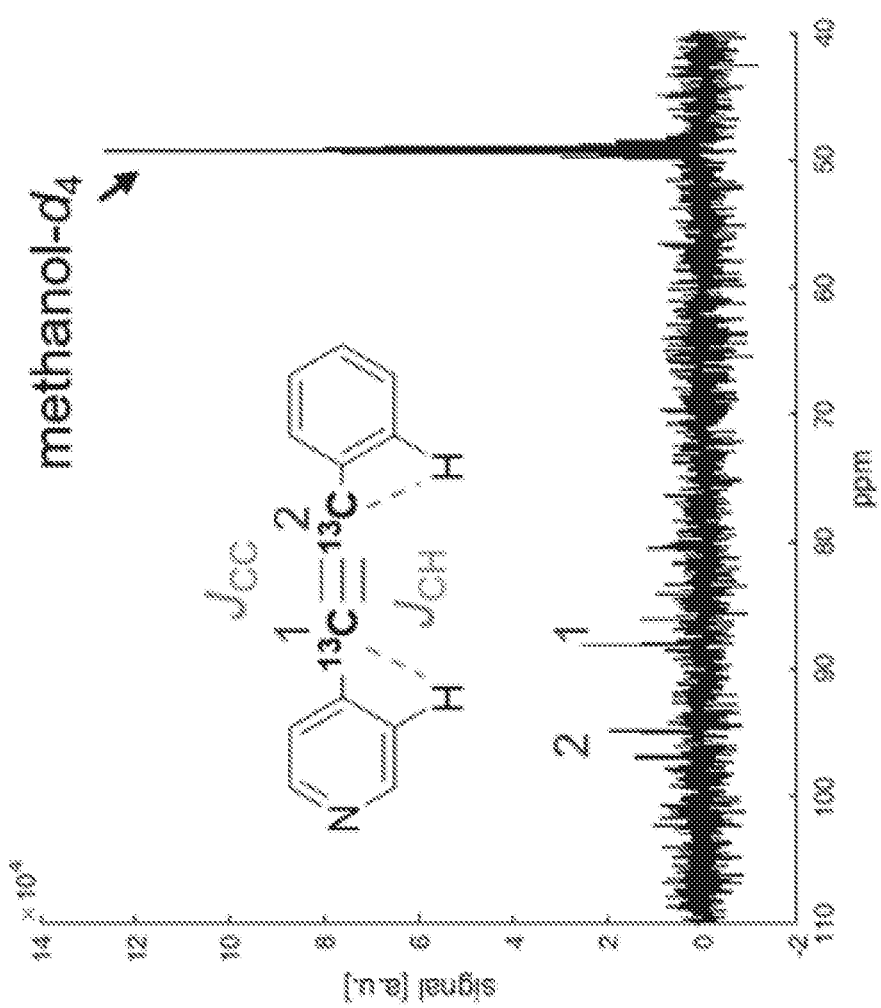
FIG. 29A shows thermal spectrum of the asymmetric molecule with concentration of 160 mM after one scan.
Figures 29B, 29C:
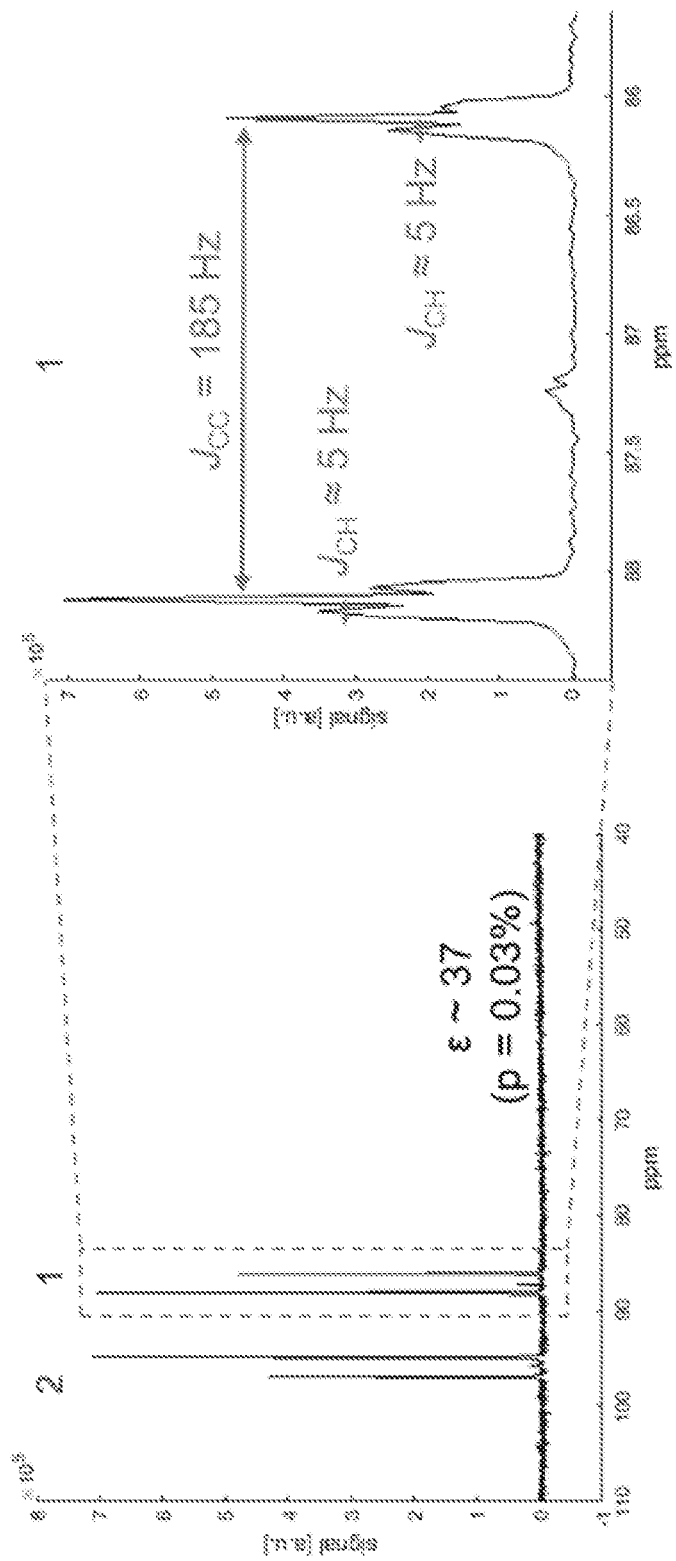
FIG. 29B shows hyperpolarized $^{13}C$ spectrum. para-$H_2$ is bubbled through the sample at 0.28 μT, achieving ~37 fold enhancement of the doubly labeled acetylenic carbons.
FIG. 29C shows the $^{13}C$-$^{13}C$ J-coupling, $J_{CC}$, and the nearby $^{13}C$-$^1H$ J-coupling, could be determined using the hyperpolarized spectrum. The critical parameter for the polarization transfer, $J_{CC}$, is 185 Hz; and $J_{CH}$ is around 5 Hz. By ab-initio calculations $J_{CC}$ values were found that are very close to this experimental value for the free species and for the N-bound substrate. Whereas, in the substrate bound via C≡C triple bond the J-coupling is reduced to ~120 Hz because of the reduction in triple-bond character upon binding. This would result in a strong shift in the magnetic field at which SABRE hyperpolarization occurs, which however was not observed, suggesting that the N-binding species in solution are primarily responsible for the observed SABRE-SHEATH effect.

Thermal and hyperpolarized $^{13}C$ spectra are analyzed to obtain the important parameters such as the $^{13}C$-$^{13}C$ J-coupling, $J_{CC}$. Other J-coupling parameters could also be distinguished from the hyperpolarized spectrum (FIG. 29).

Measurements of the Lifetime

The magnetization is created in the shield with magnetic field of 0.28 μT, then the sample is positioned at 0.3 mT for relaxation, followed by transport to the magnet for read out. By positioning the sample for different time delays at 0.3 mT, its $T_1$ lifetime is measured. A similar procedure is used for singlet lifetime measurement. The singlet states are first created in the shield with 6.2 μT then positioned at 0.3 or 50 mT for varying time delays, after which the sample is transferred to the 8.45 T for read out of the antiphase peaks.

Analysis of the Polarization Transfer

Figure 30:
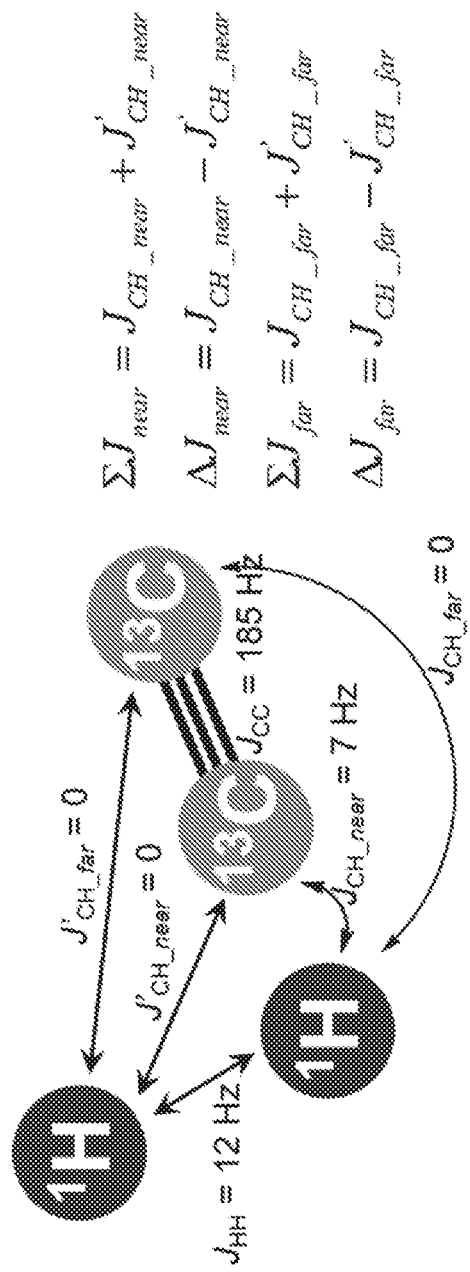
FIG. 30 shows the four-spin system of two $^1H$ and two $^{13}C$ spins, the iridium metal atom in the middle is omitted. On the left is the rearranging terms for $\Delta J_{near}$, $\Delta J_{far}$, $\Sigma J_{near}$ and $\Sigma J_{far}$. Approximation of the J-coupling values (from both calculation and experimental results) are also shown.

First, we consider a four-spin system consisting of two parahydrogen derived hydrides and two $^{13}C$ spins of the acetylenic bond as depicted in FIG. 30. This represents the direct model, where the substrate is bound to Iridium via the acetylenic bond.

Then its Hamiltonian of this system can be expressed as:

$$H = v_H(I_{1Hz} + I_{2Hz}) + v_C(I_{1Cz} + I_{2Cz}) + J_{HH}\vec{I}_{1H}\vec{I}_{2H} + J_{CC}\vec{I}_{1C}\vec{I}_{2C} + \quad (S1)$$
$$J_{CH\_near}\vec{I}_{1H}\vec{I}_{1C} + J'_{CH\_near}\vec{I}_{2H}\vec{I}_{1C} + J_{CH\_far}\vec{I}_{1H}\vec{I}_{2C} + J'_{CH\_far}\vec{I}_{2H}\vec{I}_{2C}$$

Introducing the CH-J-coupling terms (also illustrated in FIG. 28), the sum and the difference of the near and far $J_{CH}$ couplings can be written as:

$$\Sigma J_{near} = J_{CH\_near} + J_{CH\_near}'$$

$$\Delta J_{near} = J_{CH\_near} - J_{CH\_near}'$$

$$\Sigma J_{far} = J_{CH\_far} + J_{CH\_far}'$$

$$\Delta J_{far} = J_{CH\_far} - J_{CH\_far}' \quad (S2)$$

Using these definitions, the Hamiltonian is rearranged as:

$$H = v_H(I_{1Hz} + I_{2Hz}) + v_C(I_{1Cz} + I_{2Cz}) + J_{HH}\vec{I}_{1H}\vec{I}_{2H} + J_{CC}\vec{I}_{1C}\vec{I}_{2C} + \quad (S3)$$
$$\frac{\Sigma J_{near}}{2}(\vec{I}_{1H}\vec{I}_{1C} + \vec{I}_{2H}\vec{I}_{1C}) + \frac{\Delta J_{near}}{2}(\vec{I}_{1H}\vec{I}_{1C} - \vec{I}_{2H}\vec{I}_{1C}) +$$
$$\frac{\Sigma J_{far}}{2}(\vec{I}_{1H}\vec{I}_{2C} + \vec{I}_{2H}\vec{I}_{2C}) + \frac{\Delta J_{far}}{2}(\vec{I}_{1H}\vec{I}_{2C} - \vec{I}_{2H}\vec{I}_{2C})$$

To better understand the Hamiltonian, a matrix representation will be more helpful, which requires to expression the Hamiltonian in the basis that containing its eigenvectors. The most adequate basis at hand is the singlet-triplet basis, which is:

$$S_0 = \frac{1}{\sqrt{2}}(|\alpha\beta\rangle - |\beta\alpha\rangle) \quad \text{(S4)}$$

$$T_+ = |\alpha\alpha\rangle, \ T_0 = \frac{1}{\sqrt{2}}(|\alpha\beta\rangle - |\beta\alpha\rangle), \ T_- = |\beta\beta\rangle$$

Using this singlet-triplet basis for both the hydride (from para-$H_2$) and the $^{13}C$ pair, we can identify all possible 16 combinations of $^1H$ and $^{13}C$ states, which can be sorted in two groups in terms of their symmetry, they are:

10 symmetric states with respect of exchanging $H_1$ with $H_2$ and $C_1$ with $C_2$:

$S_0^H S_0^C, \ T_0^H T_0^C$ $T_+^H T_-^C, \ T_-^H T_+^C$ $T_+^H T_+^C, \ T_-^H T_-^C$ $T_0^H T_+^C, \ T_+^H T_0^C$ $T_0^H T_-^C, \ T_-^H T_0^C$ and 6 antisymmetric states with respect of exchanging $H_1$ with $H_2$ and $C_1$ with $C_2$:

$S_0^H T_0^C, \ T_0^H S_0^C$ $S_0^H T_+^C, \ T_+^H S_0^C$ $S_0^H T_-^C, \ T_-^H S_0^C$

Having represented the Hamiltonian in the matrix form using the singlet-triple basis (the full matrix is listed at the end of this document), we can see that there are no elements in the matrix that connects the groups with different symmetry. However, within the individual groups, the states are connected and the Hamiltonian can drive the hyperpolarization from the hydride singlet ($S_0^H$) to other states that generate either hyperpolarized $^{13}C$-magnetization by affecting population in the $T_+^C$, $T_-^C$ states, or $^{13}C_2$-singlet by affecting the $S_0^C$ population.

The initial state is the para-$H_2$ derived singlet on the hydride proton pair and all other states are close to 0 population, thus the initial states have the following populations:

$$p(S_0^H S_0^C) = p(S_0^H T_+^C) = p(S_0^H T_0^C) = p(S_0^H T_-^C) = 0.25 \quad \text{(S5)}$$

$p$ (other states) = 0

Choosing subsets of the connected states from the full Hamiltonian, we can see that magnetization and singlet are hyperpolarized in the shield with different magnetic field. For example, the $S_0^H T_-^C$ and $T_-^H T_0^C$ states are connected:

|  | $|S_0^H T_-^C\rangle$ | $|T_-^H T_0^C\rangle$ | (S6) |
|---|---|---|---|
| $|S_0^H T_-^C\rangle$ | $-\nu_C - J_{HH}$ | $\frac{-\Delta J_{far} - \Delta J_{near}}{4}$ | |
| $|T_-^H T_0^C\rangle$ | $\frac{-\Delta J_{far} - \Delta J_{near}}{4}$ | $-\nu_H$ | |

At specific magnetic field when the difference of the diagonal elements is made very small, the off-diagonal element will drive the population transferred from $S_0^H T_-^C$ to $T_-^H T_0^C$, thus reducing population in $T_-^C$ state of carbon and creating hyperpolarized $T_+^C$ state. The corresponding resonance condition, obtained by demanding the diagonal elements be equal, is $$\nu_H - \nu_C = J_{HH} \quad \text{(S7)}$$

Since the chemical shift frequency $\nu = \gamma B_0$, the magnetic field to match this resonance condition is:

$$B_0 = \frac{\nu_H - \nu_C}{\gamma_H - \gamma_C} = \frac{J_{HH}}{\gamma_H - \gamma_C} \quad \text{(S8)}$$

Using $J_{HH} \approx 9$ Hz, $\gamma_H = 42.576$ Hz/µT, $\gamma_C = 10.705$ Hz/µT, we can now estimate the magnetic field would be around 3mG, which matches our experimental results.

In addition, magnetization of the $^{13}C$ pair could also be polarized at relatively higher field in the shield, for example, the subset matrix is:

|  | $|S_0^H S_0^C\rangle$ | $|T_+^H T_-^C\rangle$ | $|T_-^H T_+^C\rangle$ | (S9) |
|---|---|---|---|---|
| $|S_0^H S_0^C\rangle$ | $-(J_{CC} + J_{HH})$ | $\frac{\Delta J_{far} - \Delta J_{near}}{4}$ | $\frac{\Delta J_{far} - \Delta J_{near}}{4}$ | |
| $|T_+^H T_-^C\rangle$ | $\frac{\Delta J_{far} - \Delta J_{near}}{4}$ | $\nu_H - \nu_C - \frac{\Sigma J_{near} + \Sigma J_{far}}{4}$ | 0 | |
| $|T_-^H T_+^C\rangle$ | $\frac{\Delta J_{far} - \Delta J_{near}}{4}$ | 0 | $\nu_C - \nu_H + \frac{\Sigma J_{near} + \Sigma J_{far}}{4}$ | |

Changing the magnetic field by adjusting the current in the coil, once again the diagonal elements could be made equal, and the off-diagonal element will drive the population from $|S_0^H S_0^C\rangle$ to either $|T_+^H T_-^C\rangle$ or $|T_-^H T_+^C\rangle$, polarizing the $|T_-^C\rangle$ or $|T_+^C\rangle$ state of the carbons. The corresponding resonance condition is:

$$\nu_H - \nu_C = -(J_{CC} + J_{HH}) + \frac{\Sigma J_{near} + \Sigma J_{far}}{4} \quad \text{or} \quad \text{(S10a)}$$

$$\nu_H - \nu_C = (J_{CC} + J_{HH}) + \frac{\Sigma J_{near} + \Sigma J_{far}}{4} \quad \text{(S10b)}$$

In the spin system, since $$\frac{\Sigma J_{near} + \Sigma J_{far}}{4} \approx \frac{7+0}{4} = 1.75 \text{ Hz},$$

which is much smaller than the $J_{CC} + J_{HH} \approx 185 + 9 = 194$ Hz, the sum of the J-coupling term could be dropped and the resonance condition could be simplified as:

$$\nu_H - \nu_C = \pm(J_{CC} + J_{HH}) \quad \text{(S10)}$$

The negative sign corresponds to turning the magnetic field in the shield to the other direction. Also, since now the matching condition is around 194 Hz, which is much larger than the previous condition, using this number and equation S8 again, the magnetic field is around 60 mG, which is also consistent with our experimental results.

On the other hand, we can establish the singlet polarization condition by examining the Hamiltonian matrix subset that connects the hydride singlet and singlet on carbons, one example is:

$$
\begin{array}{ccc}
 & S_0^H T_+^C & T_+^H S_0^C \\
S_0^H T_+^C & -J_{HH} + v_C & \frac{\Delta J_{near} - \Delta J_{far}}{4} \\
T_+^H S_0^C & \frac{\Delta J_{near} - \Delta J_{far}}{4} & -J_{CC} + v_H
\end{array} \tag{S11}
$$

and the resonance condition to polarize $S_0^C$ state on carbon is:

$$v_H - v_C = J_{CC} - J_{HH} \tag{S12}$$

Accordingly, that is a 176 Hz difference and the matching magnetic field would be around 50 mG, which is similar to the second magnetization polarization condition and matches with experiments.

The direct binding model may only have a small contribution to the observed SABRE spectra and we conclude that the hyperpolarization transfer is more likely through a larger spin system of additional protons in the pyridine rings. In this case, iridium of the catalyst binds with the nitrogen of the pyridyl ring, thus forming an eight-spin system (2 para-$H_2$ protons, 4 pyridyl protons and 2 carbon-13 s). In the following section we find by numerical simulation that the general behavior of the two models is surprisingly similar. At the end, we can use the relative positions of the resonances to distinguish the two models as described in the following.

Spin Dynamics of Low to High Field Sample Transfer

Hyperpolarization of both magnetization and singlet order, which are generated at low field, are detected in the 8.45 T high field inside the magnet. The transfer process of the sample is highly adiabatic, indicating that the population will stay at eigenstates of the system during transfer.

Since magnetization is represented as $I_{1z}+I_{2z}$, which is associated with population difference between the $\alpha\alpha$ and $\beta\beta$ states, they are eigenstates at both low and high fields. Therefore magnetization remains unchanged during the transfer process. When a 90° pulse is applied in the magnet, we will obtain an in-phase spectrum, as shown in the main article in FIG. 25B, panel (1).

The singlet order, however, is only an eigenstate at low magnetic field and is not detectable. It is converted into a detectable state during transfer from low to high field if a chemical shift difference between the two $^{13}$C spins exists. To enable this transformation, we designed the asymmetric molecule 1-phenyl-2-(4-pyridyl) acetylene, with the chemical shift difference of the two acetylenic $^{13}$C spins of 9 ppm. At low magnetic field, e.g. 100 G and below, the chemical shift difference ($\Delta\delta \leq 1$ Hz) is much smaller than their J-coupling ($J_{CC}$=185 Hz), so the system is strongly coupled and the singlet order is eigenstate, that is well protected from coherent evolution and subsequent relaxation.

The singlet will not be an eigenstate at high magnetic fields. We calculated the associated eigenstate as function of magnetic field, (or rather, the frequency difference between the $^{13}$C spins, $\Delta v$, which is proportional the magnetic field):

$$|eigenstate(\Delta v)\rangle = \frac{\sqrt{\Delta v^2 + J_{CC}^2} - \Delta v}{J_{CC}} |\alpha\beta\rangle - |\beta\alpha\rangle \tag{S13}$$

Accordingly, the field dependent density matrix is:

$$\rho(\Delta v) = |eigenstate(\Delta v)\rangle \langle eigenstate(\Delta v)| \tag{S14}$$

The initial density matrix of the singlet when $\Delta v$=0 is:

$$\rho_0 = \tfrac{1}{4}\hat{i} - (I_{1z}I_{2z} + I_{1x}I_{2x} + I_{1y}I_{2y}) \tag{S15}$$

By raising the magnet field this density matrix becomes:

$$\rho(\Delta v) = \frac{1}{4}\hat{I} - I_{1z}I_{2z} - \frac{J_{CC}}{\sqrt{\Delta v^2 + J_{CC}^2}}(I_{1x}I_{2x} + I_{1y}I_{2y}) - \frac{\Delta v}{\sqrt{\Delta v^2 + J_{CC}^2}}\frac{1}{2}(I_{1z} - I_{2z}) \tag{S16}$$

When $\rho(\Delta v)$ is probed with a 90° pulse at 8.45 T ($\Delta v$=815 Hz), only the $I_{1z}-I_{2z}$ component yields signal in two antiphase doublets, and plugging in the numbers we would have 98% singlet detected, compared with a infinite high detection magnetic field case (where $\Delta v=\infty$ and the density matrix corresponds to $\rho(\Delta v)=\tfrac{1}{4}\hat{i} - I_{1z}I_{2z} - \tfrac{1}{2}(I_{1z}-I_{2z})$, which is a pure population of the $\beta\alpha$ state).

Numerical Simulation

Full Range Simulation of the 4 Spin System

Figure 31A:
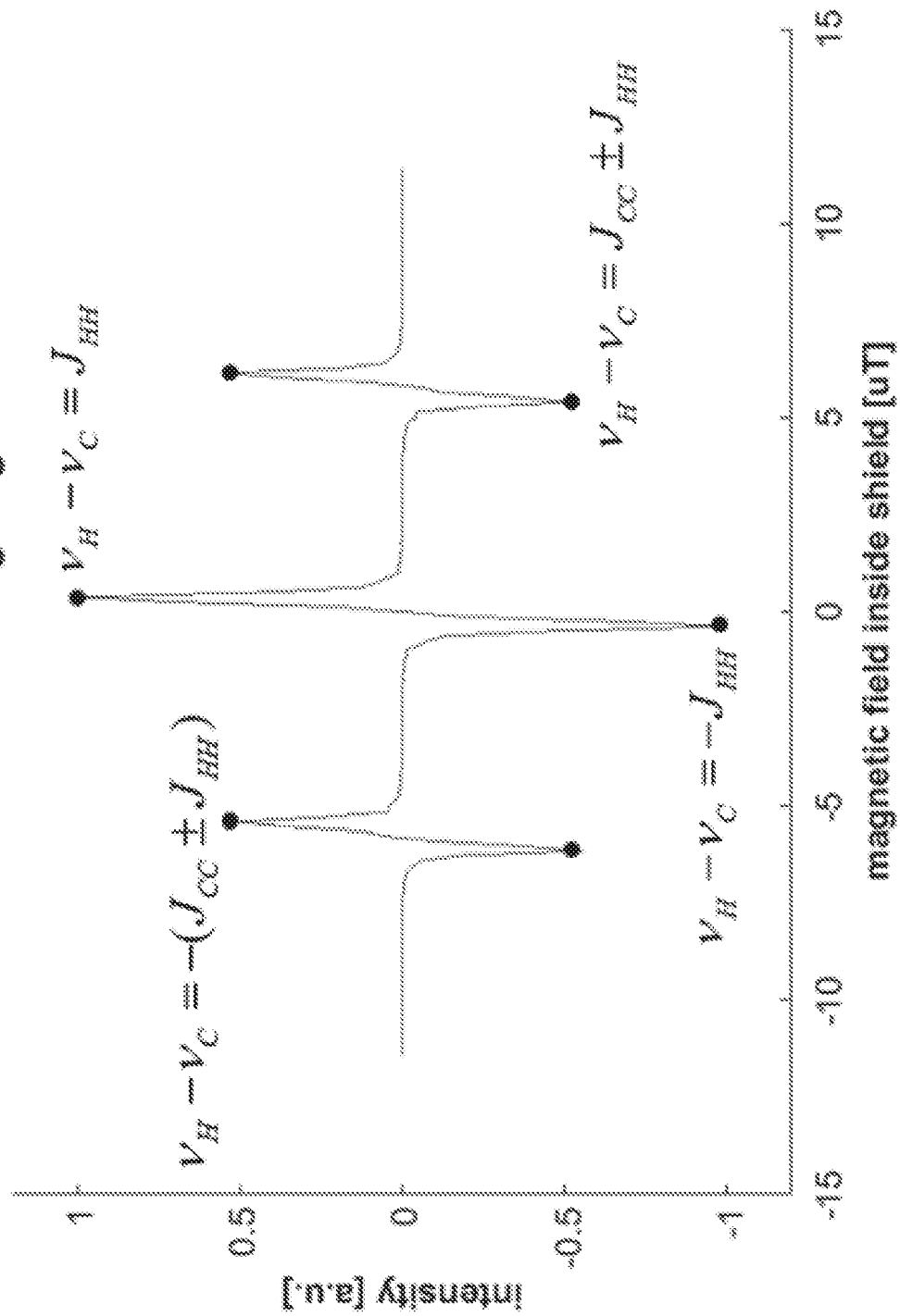
FIGS. 31A and 31B show a simulation of the polarization transfer of magnetization (FIG. 31A) and singlet (FIG. 32B), with the magnetic field ranging from ~12 to 12 μT. Highlighted points are all the resonance conditions where the polarization transfer is maximized.
Figure 31B:
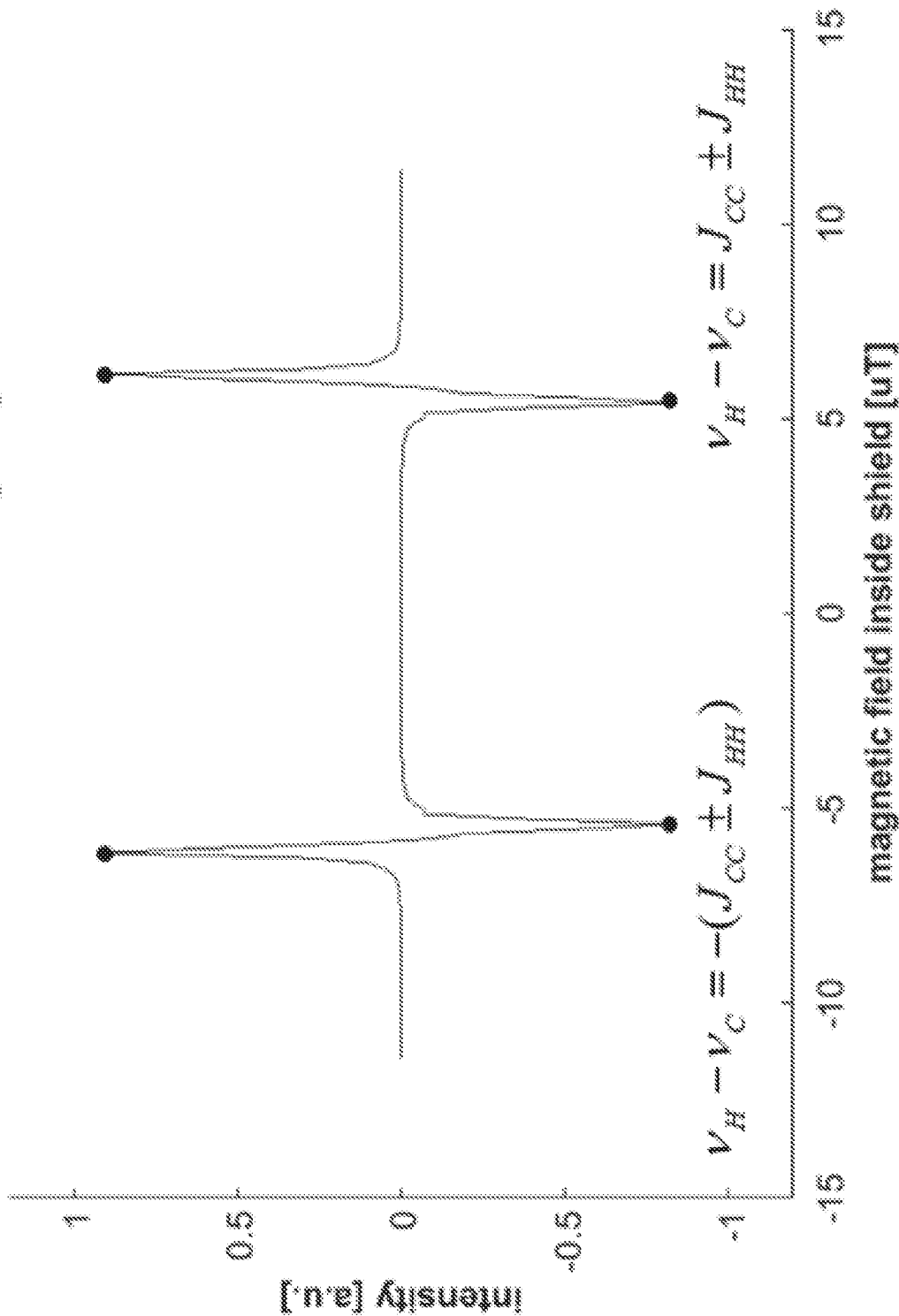

To better illustrate the mechanism of the polarization transfer, we used the Matlab package, Spinach, to simulate the magnetization and singlet polarization of $^{13}$C as a function of the magnetic field. The full range simulation from negative to positive magnetic field, as well as all the resonance conditions are shown in FIG. 31.

For the magnetization simulation, the low field polarization around 0.3 μT matches well with the experiment and our derivation. However, at around 6 μT, there is splitting between the magnetization polarizations of about $2J_{HH}$. The experimental magnetization data also indicates that behavior, however not as clearly as the simulations. We believe that magnetization can be strongly affected by the sample transfer from inside the shield to the magnet. Specifically, crossing strong magnetic field gradients or magnetic field inversion points may cause non-adiabatic evolution of the magnetization, which causes broader features in the experiment.

The singlet simulation shows great consistency with our experiment. There is no singlet polarized at extremely low field. The singlet is only polarized at around 6 μT, and the splitting of around $2J_{HH}$ is clearly observed in the experiment, which could be due to the immunity of singlet to magnetic fields. Furthermore, the polarization level of the singlet is quite high at 6 μT, indicating that polarization of the singlet is efficient; this is also consistent with the experimental results.

Comparison Between the Simulation of Direct and Indirect Polarization Transfer

Figure 32A:
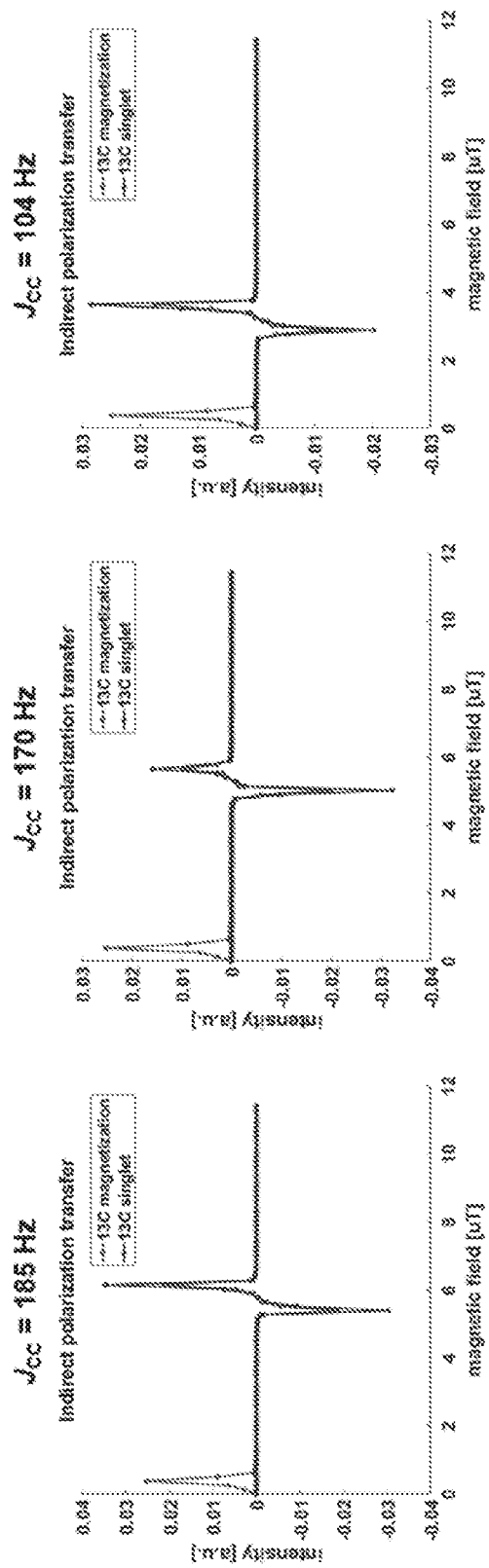
FIGS. 32A and 32B show Matlab simulation using the Spinach package, for the indirect polarization transfer (FIG. 32A, where there are 8 spins in the system) and the direct polarization transfer (FIG. 32B, where there are 4 spins in the system). Simulation shows similar pattern of the magnetization and singlet for indirect or direct polarization transfer. On the other hand, the magnetic field position at which the singlet peak appears is closely related with the $J_{CC}$ coupling: the stronger this coupling is, the further away the singlet peak will appear.
Figure 32B:
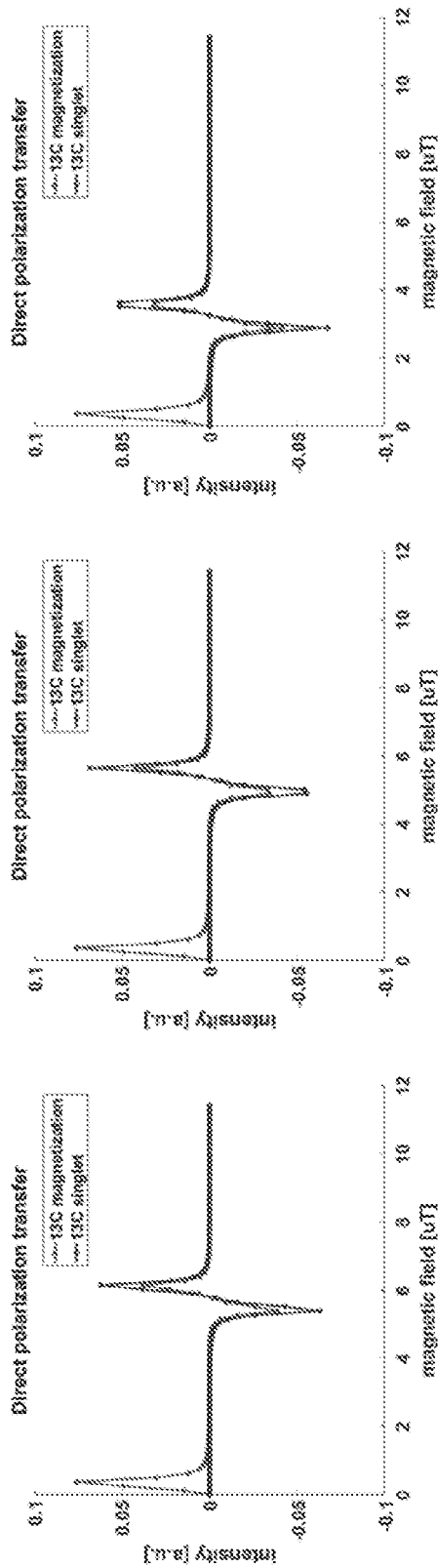

Since the nature of the binding mode in the real system was in question, we use simulation to detect if there are differences of the polarization transfer transitions between the two modes. We simulate the direct and indirect model and vary parameter of the J-coupling terms used in the simulation. As illustrated in FIG. 32, we find that the direct and indirect polarization transfer spin systems tend to give quite similar transfer patterns for comparable J-coupling constants in the source ($J_{HH}$) and the final target ($J_{CC}$).

As apparent from FIG. 32 in combination with the analytical expressions provided in the main manuscript for the resonance conditions, the polarization profile is determined by two critical J-coupling parameters, Jim and $J_{CC}$. Jim determines the position of the first resonance condition for forming magnetization. Jim also controls the distance between the two resonance conditions at higher fields. Finally, $J_{CC}$ dictates the overall position of the higher field resonances. This is true irrespective of the hyperpolarization transfer pathway (direct or indirect).

Simulation at the Optimal $^1$H Hyperpolarization Field (6.5 mT)

In addition to the simulation of the polarization transfer at low field (from −12 to 12 6 μT), simulations at higher field (6.5 mT) where 4-1 hyperpolarization works best are also performed. However, all of the simulations give 0 transfer to $^{13}$C, which is as expected because at such field there is no energy level crossing between $^1$H and $^{13}$C spins. Although polarization transferred to $^1$H, there is still no energy level crossing between the auxiliary $^1$H's and $^{13}$C's. This is also consistent with the experimental results, the $^{13}$C hyperpolarization is negligible when bubbling at 6.5 mT.

DFT Calculation of PTC Complexes.

Figure 33:
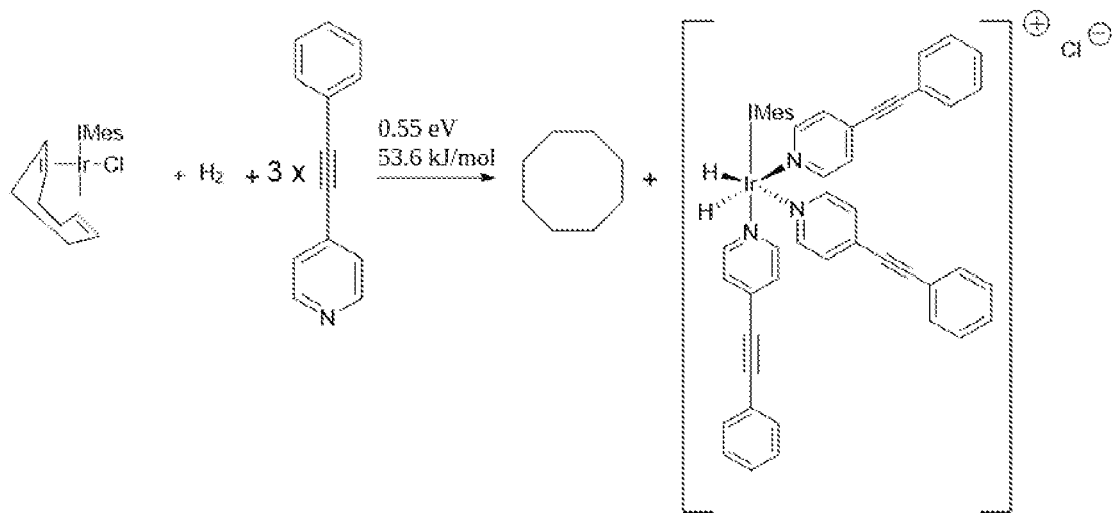
FIG. 33 shows DFT calculation of the activation process and equilibria and energies of interest. During activation, the COD (cyclooctadiene) will disassociate from the iridium core, then $H_2$ and the substrate will bind with the iridium, either with three N or the $^{13}C$ triple bond.
Figure 33:
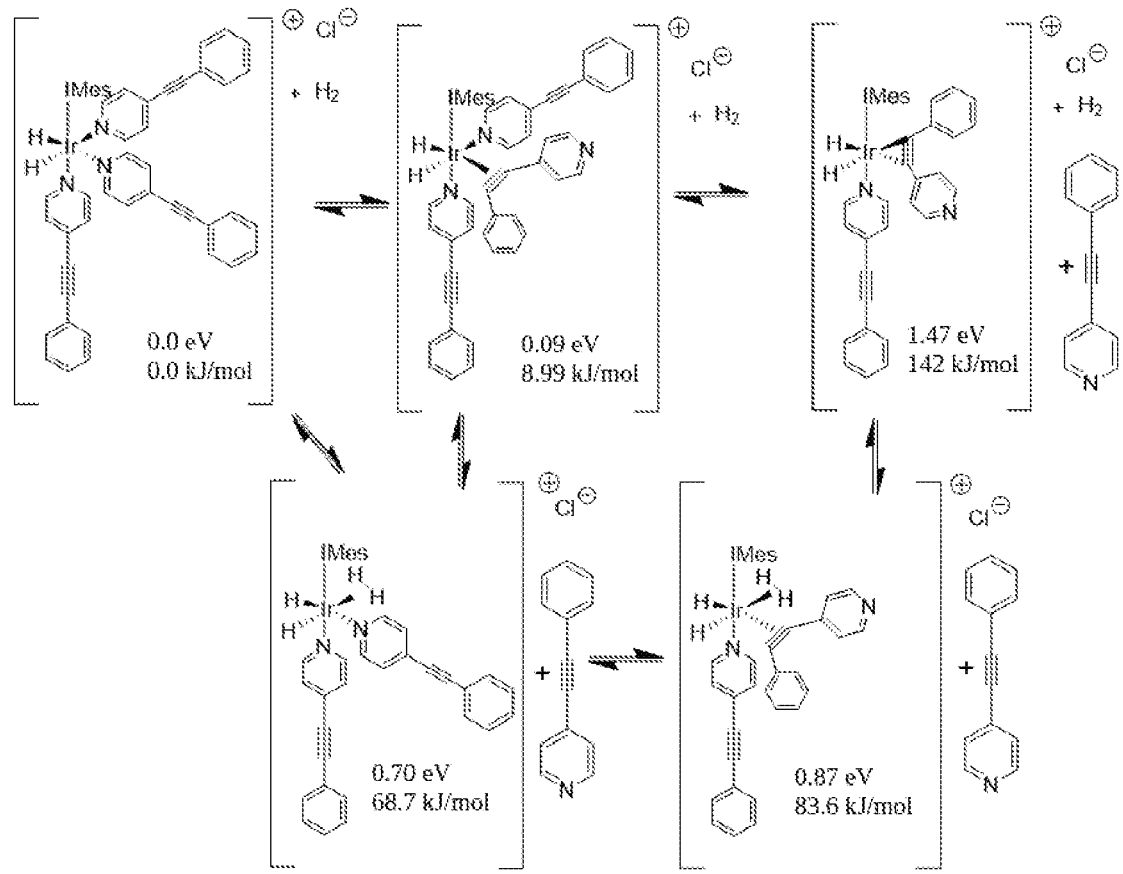

In addition to the spin dynamics simulations, the binding mode was also investigated with DFT calculations using the all-electron FHI-aims code. The tight settings were used for the integration grids and basis sets. We used the PBE exchange-correlation functional plus Tkatchenko-Scheffler vdW correction. In FIG. 33, the total energy of each configuration is taken as a sum of its isolated components (e.g., separate calculations were performed for Cl⁻, H$_2$, etc.). In the article we showed two major binding complexes. Here we displayed the full process of catalyst activation and energy differences of all possible PTC's. The geometries were first built by hand and minimized in Jmol and then relaxed with FHI-aims. No extensive conformational search was performed. The geometries are shown in Table 15. Here we compare the ground state energies only and do not consider other energy contributions (vibrations, solvent effects, etc.). We conclude that the indirect transfer should be the main polarization process. In case the acetylenic bond is complexed to the Iridium, the calculated C—C J-coupling is only 120 Hz, whereas for the substrate bound via nitrogen, $J_{CC}$ is calculated to be on the order of 191 Hz, more in line with the experimental data. The J-couplings were calculated nonrelativistically with FHI-aims. Table 14 presents a basis set convergence study for the J-coupling of the PTC of FIG. 24A. We have taken the Dunning cc-pVnZ basis sets and uncontracted all the s-functions, which we denote u-cc-pVnZ. Uncontraction is necessary since it gives the basis sets extra flexibility in the core region, which is necessary to converge the difficult Fermi contact (FC) contribution of the J-coupling. Using the regular contracted cc-pVnZ basis sets would lead to poor convergence of FC and therefore the total J-coupling. After doing a convergence study with the u-cc-pVnZ for the PTC of FIG. 24A, we used a fully uncontracted cc-pV5Z to calculate the final J-couplings for both PTC. Using u-cc-pV5Z we estimate the basis set error to be within a few percent.

TABLE 14

Basis set convergence study for the PTC of FIG. 24A. u-cc-pVnZ refers to the regular cc-pVnZ basis sets with the s functions uncontracted. A fully uncontracted cc-pV5Z basis set yields 190.7 Hz, showing that the dominant contribution to the J-couplings comes from the core s orbitals.

| | |
|---|---|
| u-cc-pVDZ | 176.8 Hz |
| u-cc-pVTZ | 179.3 Hz |
| u-cc-pVQZ | 187.0 Hz |
| u-cc-pV5Z | 190.8 Hz |

TABLE 15

Geometries of the configurations in the format of FHI-aims geometry files.

PTC 1-0.0 eV:

| | | | | |
|---|---|---|---|---|
| atom | 13.11576225 | 4.94961535 | 7.18532949 | C |
| atom | 10.90718940 | 5.47963132 | 6.85291789 | C |
| atom | 11.47867245 | 6.52825957 | 7.49109625 | C |
| atom | 13.73656820 | 7.13837865 | 8.26564473 | C |
| atom | 14.41196785 | 8.02519222 | 7.41016670 | C |
| atom | 15.28193896 | 8.95307567 | 7.98311527 | C |
| atom | 15.47771165 | 9.02469659 | 9.36751890 | C |
| atom | 14.76147947 | 8.14515954 | 10.18374824 | C |
| atom | 13.87871018 | 7.19330295 | 9.65882410 | C |
| atom | 14.19776584 | 7.98473277 | 5.92222996 | C |
| atom | 14.24930779 | 6.95811679 | 5.53669221 | H |
| atom | 14.95020238 | 8.58894345 | 5.40340215 | H |
| atom | 13.20584477 | 8.37443915 | 5.64943669 | H |
| atom | 16.44951408 | 10.01544547 | 9.94878491 | C |
| atom | 17.46306466 | 9.85240963 | 9.55327997 | H |
| atom | 16.49435821 | 9.94318002 | 11.04180964 | H |
| atom | 16.16969660 | 11.04646569 | 9.69063548 | H |
| atom | 13.10904365 | 6.26970502 | 10.56161419 | C |
| atom | 12.02561003 | 6.44137593 | 10.48541652 | H |
| atom | 13.39811557 | 6.41838943 | 11.60800079 | H |
| atom | 13.28581529 | 5.21809630 | 10.29678203 | H |
| atom | 11.67568783 | 3.32767005 | 5.90964002 | C |
| atom | 11.40460462 | 2.12517189 | 6.57955236 | C |
| atom | 11.28029114 | 0.96645168 | 5.80449083 | C |
| atom | 11.37664748 | 0.99009336 | 4.41018012 | C |
| atom | 11.54856933 | 2.22673153 | 3.78020939 | C |
| atom | 11.68908387 | 3.41072433 | 4.50650871 | C |
| atom | 11.19350971 | 2.08110944 | 8.06831118 | C |
| atom | 12.01192681 | 2.56369192 | 8.61634427 | H |
| atom | 11.10673072 | 1.04571190 | 8.41674333 | H |
| atom | 10.26511343 | 2.60415039 | 8.34254830 | H |
| atom | 11.28763047 | −0.27243964 | 3.59636759 | C |
| atom | 10.40839546 | −0.26094057 | 2.93662754 | H |
| atom | 11.21639643 | −1.16107249 | 4.23443107 | H |
| atom | 12.16935925 | −0.38553156 | 2.94848281 | H |
| atom | 11.79750749 | 4.73018374 | 3.78961395 | C |
| atom | 10.81918011 | 5.23248131 | 3.75122691 | H |
| atom | 12.13090905 | 4.58438764 | 2.75596623 | H |
| atom | 12.48764385 | 5.42493518 | 4.28275111 | H |
| atom | 16.95811952 | 5.99229109 | 6.29031123 | C |
| atom | 17.98024545 | 6.92497578 | 6.34177254 | C |
| atom | 18.46842923 | 7.35540373 | 7.59179129 | C |
| atom | 17.89096363 | 6.75629235 | 8.72910975 | C |
| atom | 16.86627071 | 5.84058229 | 8.58125159 | C |
| atom | 14.93389243 | 1.82651014 | 5.14176875 | C |
| atom | 14.91551377 | 1.24189173 | 3.89027166 | C |
| atom | 14.90897423 | 2.05079145 | 2.73520301 | C |
| atom | 14.95176730 | 3.44360981 | 2.94561313 | C |
| atom | 14.96206111 | 3.94123496 | 4.23704649 | C |
| atom | 16.30377590 | 1.79933763 | 9.04368020 | C |
| atom | 17.31615797 | 0.94878141 | 9.44500898 | C |
| atom | 18.51276774 | 0.87012459 | 8.69927659 | C |
| atom | 18.59222207 | 1.68966833 | 7.55461605 | C |
| atom | 17.53182749 | 2.51318319 | 7.22079698 | C |
| atom | 14.78760665 | 3.87659582 | 7.42070051 | Ir |
| atom | 14.60858277 | 4.21550582 | 8.96247465 | H |
| atom | 13.79560641 | 2.66926846 | 7.62093925 | H |
| atom | 16.36717449 | 5.45894172 | 7.38164240 | N |
| atom | 14.94912183 | 3.16701654 | 5.34394014 | N |

TABLE 15-continued

Geometries of the configurations in the format of FHI-aims geometry files.

| | | | | |
|---|---|---|---|---|
| atom | 16.38737450 | 2.58889230 | 7.94293289 | N |
| atom | 12.81453293 | 6.20219498 | 7.68431021 | N |
| atom | 11.90142723 | 4.53070682 | 6.66395394 | N |
| atom | 9.89418198 | 5.31698638 | 6.51059995 | H |
| atom | 11.07089240 | 7.47246738 | 7.82609062 | H |
| atom | 11.58926603 | 2.27161782 | 2.69022347 | H |
| atom | 11.09481601 | 0.01753499 | 6.31098530 | H |
| atom | 15.82986061 | 9.63406119 | 7.32932181 | H |
| atom | 14.89135110 | 8.19578464 | 11.26633671 | H |
| atom | 14.82203317 | 1.49247192 | 1.44488593 | C |
| atom | 14.59229049 | 0.42063372 | −0.95256762 | C |
| atom | 14.52163586 | −0.98109332 | −1.10178607 | C |
| atom | 14.39624795 | −1.54295173 | −2.36751520 | C |
| atom | 14.33945345 | −0.72402847 | −3.49875070 | C |
| atom | 14.40912916 | 0.66514280 | −3.36132348 | C |
| atom | 14.53467885 | 1.23892698 | −2.10095175 | C |
| atom | 14.93524934 | 5.01600160 | 4.40650229 | H |
| atom | 14.94552207 | 4.12913432 | 2.10074609 | H |
| atom | 14.90337849 | 1.21543978 | 6.04069680 | H |
| atom | 14.87811532 | 0.15829841 | 3.80228655 | H |
| atom | 14.71658881 | 0.99718304 | 0.33349706 | C |
| atom | 14.59026484 | 2.32042353 | −1.98613174 | H |
| atom | 14.24128021 | −1.16890500 | −4.48840612 | H |
| atom | 14.36551022 | 1.30344860 | −4.24314454 | H |
| atom | 14.56779066 | −1.61276333 | −0.21585924 | H |
| atom | 14.34278249 | −2.62583486 | −2.47457130 | H |
| atom | 19.46123099 | 8.34876397 | 7.70725824 | C |
| | #magnetic response | | | |
| atom | 20.29829876 | 9.22970430 | 7.82834190 | C |
| | #magnetic response | | | |
| atom | 21.26462681 | 10.25298674 | 7.97397694 | C |
| atom | 21.67740689 | 10.66490635 | 9.25928735 | C |
| atom | 22.62447716 | 11.67347278 | 9.39864814 | C |
| atom | 23.17333686 | 12.28468615 | 8.26786776 | C |
| atom | 21.82491638 | 10.87604062 | 6.83848026 | C |
| atom | 22.77147643 | 11.88324688 | 6.99080452 | C |
| atom | 19.56805485 | 0.01920746 | 9.08048118 | C |
| atom | 20.48074501 | −0.71872793 | 9.41816032 | C |
| atom | 21.53683251 | −1.57355742 | 9.81208383 | C |
| atom | 21.41260125 | −2.37513308 | 10.96721003 | C |
| atom | 22.45395340 | −3.21290233 | 11.35609034 | C |
| atom | 23.62889782 | −3.26646296 | 10.59553817 | C |
| atom | 23.76140099 | −2.47663601 | 9.44999682 | C |
| atom | 22.72715020 | −1.63483743 | 9.05615344 | C |
| atom | 22.82297921 | −1.01629766 | 8.16506164 | H |
| atom | 24.44212494 | −3.92445254 | 10.90009173 | H |
| atom | 24.67728476 | −2.51846488 | 8.86144919 | H |
| atom | 20.49420771 | −2.32776452 | 11.55042646 | H |
| atom | 22.35061734 | −3.82853529 | 12.24359171 | H |
| atom | 15.37606197 | 1.87734315 | 9.60476810 | H |
| atom | 17.18639962 | 0.34290464 | 10.33918630 | H |
| atom | 19.48378205 | 1.67942524 | 6.93126700 | H |
| atom | 17.58342333 | 3.14781127 | 6.33868523 | H |
| atom | 16.58353244 | 5.65743937 | 5.32595868 | H |
| atom | 18.39417299 | 7.32780198 | 5.41959766 | H |
| atom | 18.22578748 | 7.03337947 | 9.72618201 | H |
| atom | 16.38773286 | 5.39371278 | 9.44866032 | H |
| atom | 21.50729609 | 10.55764463 | 5.84670330 | H |
| atom | 23.91539528 | 13.07419038 | 8.38197572 | H |
| atom | 23.19987151 | 12.35919509 | 6.10937507 | H |
| atom | 21.24651038 | 10.18270892 | 10.13557218 | H |
| atom | 22.93829256 | 11.98560693 | 10.39416959 | H |
| | PTC 2−0.09 eV: | | | |
| atom | 12.61994096 | 4.68725628 | 7.21135120 | C |
| atom | 10.39359377 | 4.97555886 | 6.74583996 | C |
| atom | 10.78144088 | 6.01607156 | 7.51784122 | C |
| atom | 12.83583669 | 6.81681346 | 8.57386436 | C |
| atom | 13.44288772 | 7.88917444 | 7.90028382 | C |
| atom | 14.05440229 | 8.87552444 | 8.67437741 | C |
| atom | 14.05243718 | 8.82495592 | 10.07527131 | C |
| atom | 13.40424405 | 7.75899460 | 10.69996801 | C |
| atom | 12.78026552 | 6.74093539 | 9.97102203 | C |
| atom | 13.40868356 | 7.97821802 | 6.39979965 | C |
| atom | 13.83947757 | 7.08123482 | 5.93456690 | H |

TABLE 15-continued

Geometries of the configurations in the format of FHI-aims geometry files.

| | | | | |
|---|---|---|---|---|
| atom | 13.97364496 | 8.84637643 | 6.04428548 | H |
| atom | 12.37805455 | 8.07080900 | 6.02712158 | H |
| atom | 14.74133759 | 9.89269743 | 10.87904577 | C |
| atom | 15.81377106 | 9.93331279 | 10.64062641 | H |
| atom | 14.64531327 | 9.70981898 | 11.95529194 | H |
| atom | 14.32473420 | 10.88659030 | 10.66330188 | H |
| atom | 12.06440256 | 5.62019575 | 10.67196358 | C |
| atom | 10.97281770 | 5.75088889 | 10.62302095 | H |
| atom | 12.34865838 | 5.58321848 | 11.72924630 | H |
| atom | 12.29198044 | 4.64629636 | 10.22009118 | H |
| atom | 11.44275568 | 2.99647050 | 5.73587139 | C |
| atom | 11.29025601 | 1.73241155 | 6.32274907 | C |
| atom | 11.29126795 | 0.61844294 | 5.47207251 | C |
| atom | 11.39484656 | 0.74071615 | 4.08597318 | C |
| atom | 11.44960872 | 2.02804136 | 3.53833210 | C |
| atom | 11.46457958 | 3.16985416 | 4.33838210 | C |
| atom | 11.06202760 | 1.54001401 | 7.79870911 | C |
| atom | 11.21278879 | 2.45788421 | 8.37368247 | H |
| atom | 11.73214306 | 0.77225863 | 8.20741301 | H |
| atom | 10.03211638 | 1.19519763 | 7.97343446 | H |
| atom | 11.44417092 | −0.46755896 | 3.19149448 | C |
| atom | 10.61016363 | −0.46897796 | 2.47582443 | H |
| atom | 11.39695628 | −1.39987635 | 3.76612068 | H |
| atom | 12.37084801 | −0.47764060 | 2.59837175 | H |
| atom | 11.45724353 | 4.53596677 | 3.70555022 | C |
| atom | 10.43489830 | 4.94104374 | 3.66543324 | H |
| atom | 11.82868829 | 4.48770018 | 2.67578648 | H |
| atom | 12.06274633 | 5.26421815 | 4.25835295 | H |
| atom | 17.63244084 | 8.13245116 | 5.36910657 | C |
| atom | 16.84648593 | 7.49634177 | 6.32435644 | C |
| atom | 16.62623581 | 6.10580573 | 6.23062265 | C |
| atom | 17.24615017 | 5.45023699 | 5.14864348 | C |
| atom | 18.02076134 | 6.18377482 | 4.25307197 | C |
| atom | 14.76027853 | 1.80395007 | 5.13793564 | C |
| atom | 14.86773688 | 1.30923958 | 3.85295780 | C |
| atom | 14.83973729 | 2.19378537 | 2.75453726 | C |
| atom | 14.72602067 | 3.56607058 | 3.05352005 | C |
| atom | 14.61577488 | 3.97562390 | 4.36976072 | C |
| atom | 15.81162127 | 1.41741426 | 8.89350795 | C |
| atom | 16.80971245 | 0.55620968 | 9.30635633 | C |
| atom | 18.13462461 | 0.74217473 | 8.85357451 | C |
| atom | 18.35325099 | 1.83222979 | 7.98701248 | C |
| atom | 17.29734466 | 2.65194180 | 7.62837824 | C |
| atom | 14.38491987 | 3.74329567 | 7.50418597 | Ir |
| atom | 13.90305922 | 3.71752652 | 9.01248981 | H |
| atom | 13.45070663 | 2.45250015 | 7.60140425 | H |
| atom | 18.21854661 | 7.50660444 | 4.33617228 | H |
| atom | 14.62951274 | 3.12176764 | 5.41645769 | N |
| atom | 16.02948900 | 2.46418951 | 8.05913466 | N |
| atom | 12.13001959 | 5.83584502 | 7.79189773 | N |
| atom | 11.50911096 | 4.17323549 | 6.56135053 | N |
| atom | 9.43706758 | 4.72430033 | 6.30840570 | H |
| atom | 10.23854743 | 6.86967233 | 7.90044482 | H |
| atom | 11.49633680 | 2.14658441 | 2.45425491 | H |
| atom | 11.19617266 | −0.37515247 | 5.91453667 | H |
| atom | 14.53368090 | 9.71740958 | 8.17031532 | H |
| atom | 13.39861891 | 7.70134806 | 11.78913432 | H |
| atom | 14.88885620 | 1.72249774 | 1.42888085 | C |
| atom | 14.92848966 | 0.82387972 | −1.04856666 | C |
| atom | 14.99523747 | −0.56275138 | −1.30386690 | C |
| atom | 15.01425955 | −1.03038315 | −2.61300770 | C |
| atom | 14.96799891 | −0.13095562 | −3.68200320 | C |
| atom | 14.90244623 | 1.24400961 | −3.43919109 | C |
| atom | 14.88234483 | 1.72423777 | −2.13461893 | C |
| atom | 14.50725529 | 5.02876321 | 4.61381451 | H |
| atom | 14.70687403 | 4.30620835 | 2.25669847 | H |
| atom | 14.75490597 | 1.13328011 | 5.99330607 | H |
| atom | 14.95095031 | 0.23656974 | 3.69392474 | H |
| atom | 14.90740509 | 1.30557787 | 0.28093844 | C |
| atom | 14.83302476 | 2.79396270 | −1.93694604 | H |
| atom | 14.98402611 | −0.50218937 | −4.70615733 | H |
| atom | 14.86778800 | 1.94430080 | −4.27295435 | H |
| atom | 15.03327243 | −1.25668545 | −0.46542535 | H |
| atom | 15.06658734 | −2.10178030 | −2.80324937 | H |
| atom | 15.84102448 | 5.42795795 | 7.22356969 | C |
| atom | 15.55428896 | 5.28587256 | 8.46018865 | C |
| atom | 15.88855562 | 5.59615530 | 9.82563466 | C |

TABLE 15-continued

Geometries of the configurations in the format of FHI-aims geometry files.

| | | | | |
|---|---|---|---|---|
| atom | 15.46181285 | 4.82346256 | 10.91827859 | C |
| atom | 15.80884505 | 5.17683777 | 12.21893868 | C |
| atom | 16.59862856 | 6.30380250 | 12.45512339 | C |
| atom | 16.70168147 | 6.72206773 | 10.07612374 | C |
| atom | 17.05150811 | 7.06769593 | 11.37593733 | C |
| atom | 19.17908627 | −0.11361373 | 9.25048672 | C |
| atom | 20.08560853 | −0.85371739 | 9.60017671 | C |
| atom | 21.13561007 | −1.70925791 | 10.00662267 | C |
| atom | 20.88030445 | −2.78473960 | 10.88448530 | C |
| atom | 21.91716626 | −3.62125382 | 11.28198087 | C |
| atom | 23.21629921 | −3.40218079 | 10.81493036 | C |
| atom | 23.47894265 | −2.33984396 | 9.94526661 | C |
| atom | 22.45078164 | −1.49608994 | 9.54044734 | C |
| atom | 22.64697922 | −0.66560480 | 8.86401105 | H |
| atom | 24.02557811 | −4.06025754 | 11.12962808 | H |
| atom | 24.49187215 | −2.16947614 | 9.58226372 | H |
| atom | 19.86554912 | −2.94788704 | 11.24429326 | H |
| atom | 21.71347394 | −4.44914709 | 11.96017749 | H |
| atom | 14.78598344 | 1.28842303 | 9.22998770 | H |
| atom | 16.56988543 | −0.26145741 | 9.98251333 | H |
| atom | 19.34943016 | 2.03908604 | 7.60203564 | H |
| atom | 17.46059423 | 3.50880253 | 6.98107374 | H |
| atom | 17.80441723 | 9.20974545 | 5.43521092 | H |
| atom | 16.39471803 | 8.06578446 | 7.13453260 | H |
| atom | 17.13861531 | 4.37668390 | 5.00846607 | H |
| atom | 18.51015561 | 5.67749052 | 3.41711158 | H |
| atom | 17.04587578 | 7.32743164 | 9.23998082 | H |
| atom | 16.86777589 | 6.58119529 | 13.47381825 | H |
| atom | 17.67711122 | 7.94265923 | 11.55114704 | H |
| atom | 14.84575323 | 3.94458950 | 10.73635414 | H |
| atom | 15.46345426 | 4.56794575 | 13.05427574 | H |
| | | PTC 3−1.47 eV: | | |
| atom | 12.35633315 | 4.12024117 | 8.90819667 | C |
| atom | 10.14517555 | 4.37682646 | 8.43677494 | C |
| atom | 10.56868293 | 5.51157837 | 9.04960099 | C |
| atom | 12.76029647 | 6.38398803 | 9.86811730 | C |
| atom | 13.23549059 | 7.37137230 | 8.98809280 | C |
| atom | 14.04863515 | 8.37336650 | 9.51739823 | C |
| atom | 14.39467751 | 8.40625816 | 10.87277780 | C |
| atom | 13.88535560 | 7.41253915 | 11.71357623 | C |
| atom | 13.04970207 | 6.39428988 | 11.24040221 | C |
| atom | 12.88119302 | 7.36037705 | 7.52607807 | C |
| atom | 13.04042342 | 6.37164468 | 7.07521612 | H |
| atom | 13.49138361 | 8.08593807 | 6.97803360 | H |
| atom | 11.82489760 | 7.61960320 | 7.36318588 | H |
| atom | 15.27910108 | 9.49881555 | 11.40756157 | H |
| atom | 16.12612697 | 9.68911248 | 10.73477918 | H |
| atom | 15.67548130 | 9.25052517 | 12.39923092 | H |
| atom | 14.72373981 | 10.44372822 | 11.50016445 | H |
| atom | 12.46577666 | 5.37412180 | 12.17976719 | C |
| atom | 11.37069521 | 5.33337567 | 12.09605662 | H |
| atom | 12.71459979 | 5.61944464 | 13.21801281 | H |
| atom | 12.83857536 | 4.36213479 | 11.97011879 | H |
| atom | 11.31630284 | 2.27817966 | 7.66471106 | C |
| atom | 11.23182910 | 1.07250186 | 8.38335317 | C |
| atom | 11.34553722 | −0.12068298 | 7.65566532 | C |
| atom | 11.48358747 | −0.13570715 | 6.26654492 | C |
| atom | 11.51897362 | 1.09025753 | 5.58808534 | C |
| atom | 11.44559288 | 2.30743793 | 6.26027766 | C |
| atom | 10.93386607 | 1.02331306 | 9.85902430 | C |
| atom | 11.04852612 | 1.99456483 | 10.34810756 | H |
| atom | 11.58753645 | 0.30596372 | 10.37180835 | H |
| atom | 9.89984190 | 0.68422544 | 10.01897579 | H |
| atom | 11.56471082 | −1.42933878 | 5.50463823 | C |
| atom | 10.56660276 | −1.73717785 | 5.15844460 | H |
| atom | 11.95840483 | −2.24231716 | 6.12686322 | H |
| atom | 12.19949304 | −1.33130384 | 4.61513003 | H |
| atom | 11.50629063 | 3.60733996 | 5.50671783 | C |
| atom | 10.54950705 | 4.14717052 | 5.54819748 | H |
| atom | 11.74458474 | 3.42873588 | 4.45314863 | H |
| atom | 12.26931696 | 4.28066551 | 5.92118017 | H |
| atom | 14.73809992 | 1.80385368 | 3.70875348 | C |
| atom | 14.78381356 | 2.77873301 | 4.70106719 | C |
| atom | 14.84209114 | 2.37606845 | 6.04870992 | C |
| atom | 14.86260474 | 0.99420525 | 6.30666412 | C |
| atom | 14.83185791 | 0.10786823 | 5.23448744 | C |
| atom | 15.44649081 | 0.64211332 | 10.20635726 | C |
| atom | 16.41440604 | −0.31199156 | 10.45077032 | C |
| atom | 17.74946615 | −0.08037658 | 10.05017142 | C |
| atom | 18.00840486 | 1.15162605 | 9.41157876 | C |
| atom | 16.97883625 | 2.04755009 | 9.19171269 | C |
| atom | 14.05389040 | 3.12737372 | 9.15012629 | Ir |
| atom | 14.75690559 | 0.48374955 | 3.95068921 | N |
| atom | 15.69805359 | 1.81513086 | 9.56980490 | N |
| atom | 11.92235695 | 5.34690574 | 9.32828722 | N |
| atom | 11.24779535 | 3.53825476 | 8.35484767 | N |
| atom | 9.17408900 | 4.08879463 | 8.05699444 | H |
| atom | 10.04195578 | 6.41825572 | 9.31497651 | H |
| atom | 11.63686460 | 1.09538007 | 4.50370899 | H |
| atom | 11.29315573 | −1.06734744 | 8.19717410 | H |
| atom | 14.44131746 | 9.13779775 | 8.84545961 | H |
| atom | 14.13067112 | 7.43437974 | 12.77677745 | H |
| atom | 14.87962388 | 3.35266334 | 7.09490305 | C |
| atom | 15.25500643 | 4.38037908 | 7.72190176 | C |
| atom | 15.97643829 | 5.59452287 | 7.95454611 | C |
| atom | 16.52946872 | 5.90772866 | 9.21096001 | C |
| atom | 17.28018910 | 7.06578782 | 9.37973811 | C |
| atom | 17.47923976 | 7.93797720 | 8.30801182 | C |
| atom | 16.18365823 | 6.48167843 | 6.87700244 | C |
| atom | 16.92593012 | 7.64306960 | 7.05839204 | C |
| atom | 18.76371129 | −1.02628218 | 10.27908551 | C |
| atom | 19.64129012 | −1.85371196 | 10.47475461 | C |
| atom | 20.65523416 | −2.81194375 | 10.69953318 | C |
| atom | 20.35231001 | −4.03330339 | 11.33985169 | C |
| atom | 21.35370819 | −4.97254511 | 11.55689502 | C |
| atom | 22.66336710 | −4.71261266 | 11.14277571 | C |
| atom | 22.97294850 | −3.50614232 | 10.50808360 | C |
| atom | 21.98085714 | −2.55841672 | 10.28509205 | C |
| atom | 22.21285401 | −1.61606873 | 9.79129012 | H |
| atom | 23.44467900 | −5.45210617 | 11.31513373 | H |
| atom | 23.99406006 | −3.30536487 | 10.18606473 | H |
| atom | 19.32949513 | −4.22720275 | 11.65919677 | H |
| atom | 21.11427349 | −5.91331680 | 12.05119724 | H |
| atom | 14.41652540 | 0.48828508 | 10.52286661 | H |
| atom | 16.14530777 | −1.23549947 | 10.95860617 | H |
| atom | 19.01563898 | 1.39926473 | 9.08380807 | H |
| atom | 17.16663775 | 2.98868785 | 8.68044267 | H |
| atom | 14.68251281 | 2.09777682 | 2.65793746 | H |
| atom | 14.76095533 | 3.83618972 | 4.44229753 | H |
| atom | 14.89886932 | 0.61260107 | 7.32442715 | H |
| atom | 14.85376424 | −0.96862780 | 5.41922165 | H |
| atom | 15.75219535 | 6.24723539 | 5.90474321 | H |
| atom | 18.06469790 | 8.84676437 | 8.44390222 | H |
| atom | 17.07923284 | 8.32097115 | 6.21921467 | H |
| atom | 16.36681725 | 5.23642175 | 10.05280681 | H |
| atom | 17.70376579 | 7.29412723 | 10.35696626 | H |
| atom | 13.38778662 | 2.62388016 | 10.52025122 | H |
| atom | 14.54383564 | 4.23349788 | 10.10570577 | H |
| | | PTC 4−0.70 eV: | | |
| atom | 12.80623943 | 4.96547676 | 7.28498423 | C |
| atom | 10.64235778 | 5.53336666 | 6.81866377 | C |
| atom | 11.16328628 | 6.52756530 | 7.57735259 | C |
| atom | 13.35919616 | 7.01511105 | 8.61689666 | C |
| atom | 14.15522515 | 7.94713822 | 7.93404468 | C |
| atom | 15.01459989 | 8.74722824 | 8.69536514 | C |
| atom | 15.07961099 | 8.64729927 | 10.08706538 | C |
| atom | 14.24901556 | 7.71903332 | 10.72578116 | C |
| atom | 13.37477451 | 6.89320874 | 10.01516525 | C |
| atom | 14.08941989 | 8.08838720 | 6.43689825 | C |
| atom | 14.35976894 | 7.15235400 | 5.92615509 | H |
| atom | 14.77262563 | 8.87170461 | 6.09091739 | H |
| atom | 13.07704228 | 8.34989030 | 6.09769499 | H |
| atom | 15.99240924 | 9.53842426 | 10.88511554 | H |
| atom | 16.80342755 | 9.94300508 | 10.26790152 | H |
| atom | 16.43936695 | 9.00174695 | 11.73169412 | H |
| atom | 15.43718491 | 10.39267292 | 11.30055149 | H |
| atom | 12.48697351 | 5.90880466 | 10.72505988 | C |
| atom | 11.42272590 | 6.13130073 | 10.56150972 | H |
| atom | 12.67101476 | 5.92940201 | 11.80471775 | H |
| atom | 12.65936144 | 4.88451821 | 10.36591340 | H |
| atom | 11.47328622 | 3.44993056 | 5.78413945 | C |
| atom | 11.08691747 | 2.21934915 | 6.33370620 | C |

TABLE 15-continued

Geometries of the configurations in the format of FHI-aims geometry files.

| | | | | |
|---|---:|---:|---:|---|
| atom | 10.94521253 | 1.13636337 | 5.45757688 | C |
| atom | 11.14935895 | 1.26234133 | 4.08053633 | C |
| atom | 11.47750141 | 2.52370515 | 3.57130324 | C |
| atom | 11.63879562 | 3.63443410 | 4.40038156 | C |
| atom | 10.80089237 | 2.06761681 | 7.80229168 | C |
| atom | 11.67467696 | 2.32586479 | 8.41539285 | H |
| atom | 10.50786674 | 1.03808224 | 8.03582720 | H |
| atom | 9.98196635 | 2.72996395 | 8.11792229 | H |
| atom | 11.02399040 | 0.08022528 | 3.15821153 | C |
| atom | 10.17888046 | 0.20454705 | 2.46614085 | H |
| atom | 10.86653583 | −0.85179850 | 3.71353282 | H |
| atom | 11.92647453 | −0.03507440 | 2.54019116 | H |
| atom | 11.95578804 | 4.98450111 | 3.81637661 | C |
| atom | 11.05189869 | 5.60838468 | 3.75086358 | H |
| atom | 12.36016676 | 4.88301827 | 2.80305991 | H |
| atom | 12.67968247 | 5.54172087 | 4.42389749 | H |
| atom | 14.47421073 | 1.78065661 | 5.34549942 | C |
| atom | 14.56243399 | 1.13158738 | 4.12921167 | C |
| atom | 14.88302947 | 1.85929547 | 2.96525996 | C |
| atom | 15.14779355 | 3.23417626 | 3.13513992 | C |
| atom | 15.04365554 | 3.80237823 | 4.39222163 | C |
| atom | 16.28749662 | 1.98947802 | 9.05766710 | C |
| atom | 17.38278706 | 1.22013518 | 9.40278898 | C |
| atom | 18.56173711 | 1.28011651 | 8.62890934 | C |
| atom | 18.53977231 | 2.15107565 | 7.51910657 | C |
| atom | 17.40120297 | 2.88549405 | 7.24208463 | C |
| atom | 14.53234572 | 3.96277520 | 7.51946642 | Ir |
| atom | 14.38640306 | 4.31678052 | 9.06135291 | H |
| atom | 13.64984110 | 2.68838106 | 7.89736121 | H |
| atom | 14.68997982 | 3.10854653 | 5.49837329 | N |
| atom | 16.27305541 | 2.82315964 | 7.98858873 | N |
| atom | 12.47646106 | 6.17531140 | 7.85268146 | N |
| atom | 11.64667518 | 4.59006668 | 6.64367437 | N |
| atom | 14.90471505 | 1.24462579 | 1.69874254 | C |
| atom | 14.86699600 | 0.07215815 | −0.66160020 | C |
| atom | 14.55805231 | −1.30106817 | −0.76794033 | C |
| atom | 14.53458950 | −1.91598497 | −2.01465792 | C |
| atom | 14.81680745 | −1.17868906 | −3.16815543 | C |
| atom | 15.12443865 | 0.18147986 | −3.07289518 | C |
| atom | 15.15095926 | 0.80804683 | −1.83200950 | C |
| atom | 14.88874285 | 0.70246082 | 0.60432307 | C |
| atom | 19.69729607 | 0.51297636 | 8.94929674 | C |
| atom | 20.68053020 | −0.15371342 | 9.23338299 | C |
| atom | 21.81799393 | −0.92575132 | 9.56464149 | C |
| atom | 21.79302799 | −1.78895446 | 10.68127417 | C |
| atom | 22.91443407 | −2.54517635 | 11.00281448 | C |
| atom | 24.07120159 | −2.45474474 | 10.22336930 | C |
| atom | 24.10558668 | −1.60264199 | 9.11584752 | C |
| atom | 22.99071350 | −0.84136407 | 8.78362203 | C |
| atom | 15.53441485 | 5.30606855 | 6.91004032 | H |
| atom | 15.42779518 | 5.42693174 | 7.78492671 | H |
| atom | 9.66138550 | 5.40399010 | 6.38184527 | H |
| atom | 10.73152481 | 7.44659400 | 7.95004657 | H |
| atom | 10.65878005 | 0.16669897 | 5.86866392 | H |
| atom | 11.62766336 | 2.64428905 | 2.49689467 | H |
| atom | 15.64606310 | 9.47401653 | 8.17933407 | H |
| atom | 14.28113286 | 7.63320449 | 11.81340668 | H |
| atom | 15.22833212 | 4.86572014 | 4.53431006 | H |
| atom | 14.19428471 | 1.24091454 | 6.24630742 | H |
| atom | 14.35284855 | 0.06600507 | 4.07122340 | H |
| atom | 15.41846502 | 3.85302517 | 2.28231055 | H |
| atom | 14.34133574 | −1.86891231 | 0.13573243 | H |
| atom | 14.29597499 | −2.97631179 | −2.08954302 | H |
| atom | 14.79760060 | −1.66506383 | −4.14284390 | H |
| atom | 15.34511613 | 0.75521320 | −3.97230429 | H |
| atom | 15.39052811 | 1.86710175 | −1.74932501 | H |
| atom | 17.37400585 | 3.55844169 | 6.38722429 | H |
| atom | 19.41420918 | 2.25014766 | 6.87971334 | H |
| atom | 23.00936971 | −0.17468585 | 7.92282271 | H |
| atom | 20.88814965 | −1.85296089 | 11.28366334 | H |
| atom | 22.88862183 | −3.20918323 | 11.86609884 | H |
| atom | 24.94758506 | −3.04909017 | 10.47975781 | H |
| atom | 25.00779737 | −1.53242908 | 8.50928288 | H |
| atom | 15.37263463 | 1.95816871 | 9.64360375 | H |
| atom | 17.33016679 | 0.57046788 | 10.27367419 | H |

PTC 5–0.87 eV:

| | | | | |
|---|---:|---:|---:|---|
| atom | 12.93849121 | 5.12851276 | 6.81161236 | C |
| atom | 10.71089316 | 5.43359766 | 6.44862987 | C |
| atom | 11.30955558 | 6.64123431 | 6.31055264 | C |
| atom | 13.59984447 | 7.53944211 | 6.55531997 | C |
| atom | 14.31794024 | 7.84292832 | 5.38749011 | C |
| atom | 15.20697936 | 8.92250841 | 5.43956184 | C |
| atom | 15.35433984 | 9.70899486 | 6.58717170 | C |
| atom | 14.58264743 | 9.39451386 | 7.71131999 | C |
| atom | 13.70053763 | 8.31333013 | 7.72479068 | C |
| atom | 14.10826323 | 7.07442927 | 4.10991464 | C |
| atom | 14.17907599 | 5.98767528 | 4.25015913 | H |
| atom | 14.84393748 | 7.37069461 | 3.35418083 | H |
| atom | 13.10868682 | 7.27179677 | 3.69522996 | H |
| atom | 16.30119779 | 10.87667606 | 6.61449609 | C |
| atom | 17.05156069 | 10.80768061 | 5.81790043 | H |
| atom | 16.82231196 | 10.94516868 | 7.57817250 | H |
| atom | 15.75656390 | 11.82194829 | 6.47235737 | H |
| atom | 12.88355474 | 8.00114780 | 8.94859340 | C |
| atom | 11.81379729 | 8.19211845 | 8.78042303 | H |
| atom | 13.20421340 | 8.62205553 | 9.79166938 | H |
| atom | 12.97743953 | 6.94727579 | 9.24354453 | H |
| atom | 11.41603275 | 3.13607803 | 7.03002159 | C |
| atom | 11.02324308 | 2.78455963 | 8.32959310 | C |
| atom | 10.75329083 | 1.43496498 | 8.58093516 | C |
| atom | 10.84626241 | 0.46218208 | 7.58359838 | C |
| atom | 11.20192127 | 0.86823196 | 6.29024987 | C |
| atom | 11.48014778 | 2.20092915 | 5.98206808 | C |
| atom | 10.86687371 | 3.80938109 | 9.41852198 | C |
| atom | 11.26794353 | 4.59567432 | 9.36149963 | H |
| atom | 10.93709270 | 3.34024673 | 10.40610482 | H |
| atom | 9.88548304 | 4.30319435 | 9.35257614 | H |
| atom | 10.54065735 | −0.98175129 | 7.87718368 | C |
| atom | 9.57617739 | −1.27541138 | 7.43762112 | H |
| atom | 10.48293436 | −1.17057779 | 8.95568417 | H |
| atom | 11.30244069 | −1.64879478 | 7.45194067 | H |
| atom | 11.82338565 | 2.61427309 | 4.57865218 | C |
| atom | 11.15390135 | 3.40591359 | 4.21390082 | H |
| atom | 11.74289564 | 1.76341275 | 3.89336876 | H |
| atom | 12.84767303 | 3.00914592 | 4.51484739 | H |
| atom | 16.75778363 | 8.37985554 | 10.59098389 | C |
| atom | 15.99554009 | 7.23537682 | 10.37839762 | C |
| atom | 16.12578739 | 6.53758812 | 9.16076315 | C |
| atom | 17.05680797 | 7.04625068 | 8.23994779 | C |
| atom | 17.78160784 | 8.19966857 | 8.56175683 | C |
| atom | 16.39464852 | 1.66547039 | 6.86676384 | C |
| atom | 17.43304373 | 0.76549883 | 7.00900062 | C |
| atom | 18.62009116 | 1.15399898 | 7.66799729 | C |
| atom | 18.66299450 | 2.47805155 | 8.15288151 | C |
| atom | 17.57576878 | 3.31444846 | 7.97544227 | C |
| atom | 14.71390871 | 4.21470384 | 7.10655977 | Ir |
| atom | 13.82051991 | 2.96507884 | 7.49077963 | H |
| atom | 14.46259162 | 3.53177641 | 5.67461548 | H |
| atom | 17.63975472 | 8.87066325 | 9.70667027 | N |
| atom | 15.81157595 | 5.13071832 | 6.04002480 | N |
| atom | 16.44282233 | 2.93510517 | 7.34045430 | N |
| atom | 12.66460220 | 6.44636963 | 6.54022182 | N |
| atom | 11.70763847 | 4.51966149 | 6.75410820 | N |
| atom | 9.67553857 | 5.13324087 | 6.36216697 | H |
| atom | 10.90937708 | 7.61848663 | 6.07695763 | H |
| atom | 11.25345277 | 0.12551856 | 5.49191592 | H |
| atom | 10.46763991 | 1.14091675 | 9.59202794 | H |
| atom | 15.78686079 | 9.16536469 | 4.54746360 | H |
| atom | 14.68819305 | 9.99548519 | 8.61556482 | H |
| atom | 15.33052516 | 5.36565433 | 8.92675516 | C |
| atom | 14.67281398 | 4.35231802 | 9.31486748 | C |
| atom | 14.14048001 | 3.48234819 | 10.32378711 | C |
| atom | 13.87827544 | 2.12082068 | 10.09214205 | C |
| atom | 13.38198420 | 1.31485675 | 11.11175609 | C |
| atom | 13.12921532 | 1.85145067 | 12.37579907 | C |
| atom | 13.88751888 | 4.01390283 | 11.60736343 | C |
| atom | 13.38409078 | 3.20455666 | 12.61907524 | C |
| atom | 19.69983405 | 0.26782522 | 7.83147509 | C |
| atom | 20.63586806 | −0.50416943 | 7.97404710 | C |
| atom | 21.71864145 | −1.39749007 | 8.13972646 | C |
| atom | 21.63828584 | −2.71552645 | 7.64034384 | C |

TABLE 15-continued

Geometries of the configurations in
the format of FHI-aims geometry files.

| | | | | |
|---|---|---|---|---|
| atom | 22.70645955 | −3.58939863 | 7.80665309 | C |
| atom | 23.86362009 | −3.16785646 | 8.46804048 | C |
| atom | 23.95251611 | −1.86463212 | 8.96584356 | C |
| atom | 22.89139470 | −0.98094372 | 8.80615456 | C |
| atom | 22.95206996 | 0.03603053 | 9.19058480 | H |
| atom | 24.69816220 | −3.85652982 | 8.59562504 | H |
| atom | 24.85508325 | −1.53756914 | 9.48072949 | H |
| atom | 20.73329993 | −3.03524754 | 7.12603138 | H |
| atom | 22.63893391 | −4.60521013 | 7.41896308 | H |
| atom | 15.47643932 | 1.38383459 | 6.35757365 | H |
| atom | 17.33022881 | −0.24110002 | 6.60985590 | H |
| atom | 19.54611021 | 2.84736984 | 8.66948808 | H |
| atom | 17.59815986 | 4.33022356 | 8.36177666 | H |
| atom | 16.65161120 | 8.93904620 | 11.52356957 | H |
| atom | 15.28950267 | 6.89831106 | 11.13487851 | H |
| atom | 17.20732539 | 6.57161609 | 7.27264129 | H |
| atom | 18.50467342 | 8.59303608 | 7.84909655 | H |
| atom | 14.07717110 | 5.06945208 | 11.79548820 | H |
| atom | 12.73460755 | 1.21920961 | 13.17043184 | H |
| atom | 13.18681720 | 3.62998295 | 13.60247479 | H |
| atom | 14.05732367 | 1.70455927 | 9.10293085 | H |
| atom | 13.18393452 | 0.26160612 | 10.91543979 | H |
| atom | 15.36300419 | 5.75453266 | 6.42106671 | H |

Full Matrix of the Hamiltonian

|  | $\lvert S_0^H S_0^C\rangle$ | $\lvert T_0^H T_0^C\rangle$ | $\lvert T_+^H T_-^C\rangle$ | $\lvert T_-^H T_+^C\rangle$ | $\lvert T_+^H T_+^C\rangle$ | $\lvert T_-^H T_-^C\rangle$ | $\lvert T_0^H T_+^C\rangle$ | $\lvert T_+^H T_0^C\rangle$ |
|---|---|---|---|---|---|---|---|---|
| $\lvert S_0^H S_0^C\rangle$ | $-(J_{HH}+J_{CC})$ | $\dfrac{\Delta J_{near}-\Delta J_{far}}{4}$ | $\dfrac{\Delta J_{far}-\Delta J_{near}}{4}$ | $\dfrac{\Delta J_{far}-\Delta J_{near}}{4}$ | 0 | 0 | 0 | 0 |
| $\lvert T_0^H T_0^C\rangle$ | $\dfrac{\Delta J_{far}-\Delta J_{near}}{4}$ | 0 | $\dfrac{\Sigma J_{near}+\Sigma J_{far}}{4}$ | $\dfrac{\Sigma J_{near}+\Sigma J_{far}}{4}$ | 0 | 0 | 0 | 0 |
| $\lvert T_+^H T_-^C\rangle$ | $\dfrac{\Delta J_{far}-\Delta J_{near}}{4}$ | $\dfrac{\Sigma J_{near}+\Sigma J_{far}}{4}$ | $(\nu_H-\nu_C)-\dfrac{\Sigma J_{near}+\Sigma J_{far}}{4}$ | 0 | 0 | 0 | 0 | 0 |
| $\lvert T_-^H T_+^C\rangle$ | $\dfrac{\Delta J_{far}-\Delta J_{near}}{4}$ | $\dfrac{\Sigma J_{near}+\Sigma J_{far}}{4}$ | 0 | $(\nu_C-\nu_H)-\dfrac{\Sigma J_{near}+\Sigma J_{far}}{4}$ | 0 | 0 | 0 | 0 |
| $\lvert T_+^H T_+^C\rangle$ | 0 | 0 | 0 | 0 | $\dfrac{\Sigma J_{near}+\Sigma J_{far}}{4}+\nu_H+\nu_C$ | 0 | 0 | 0 |
| $\lvert T_-^H T_-^C\rangle$ | 0 | 0 | 0 | 0 | 0 | $\dfrac{\Sigma J_{near}+\Sigma J_{far}}{4}-(\nu_H+\nu_C)$ | 0 | 0 |
| $\lvert T_0^H T_+^C\rangle$ | 0 | 0 | 0 | 0 | 0 | 0 | $\nu_C$ | $\dfrac{\Sigma J_{near}+\Sigma J_{far}}{4}$ |
| $\lvert T_+^H T_0^C\rangle$ | 0 | 0 | 0 | 0 | 0 | 0 | $\dfrac{\Sigma J_{near}+\Sigma J_{far}}{4}$ | $\nu_H$ |
| $\lvert T_0^H T_-^C\rangle$ | 0 | 0 | 0 | 0 | 0 | 0 | 0 | 0 |
| $\lvert T_-^H T_0^C\rangle$ | 0 | 0 | 0 | 0 | 0 | 0 | 0 | 0 |
| $\lvert S_0^H T_0^C\rangle$ | 0 | 0 | 0 | 0 | 0 | 0 | 0 | 0 |
| $\lvert S_0^H T_+^C\rangle$ | 0 | 0 | $\dfrac{\Delta J_{far}+\Delta J_{near}}{4}$ | $\dfrac{-\Delta J_{far}-\Delta J_{near}}{4}$ | 0 | 0 | $\dfrac{-\Delta J_{far}-\Delta J_{near}}{4}$ | $\dfrac{\Delta J_{far}+\Delta J_{near}}{4}$ |
| $\lvert S_0^H T_-^C\rangle$ | 0 | 0 | $\dfrac{\Sigma J_{far}-\Sigma J_{near}}{4}$ | $\dfrac{\Sigma J_{near}-\Sigma J_{far}}{4}$ | 0 | 0 | $\dfrac{\Sigma J_{near}-\Sigma J_{far}}{4}$ | $\dfrac{\Sigma J_{far}-\Sigma J_{near}}{4}$ |
| $\lvert T_0^H S_0^C\rangle$ | 0 | 0 | 0 | 0 | 0 | 0 | 0 | 0 |
| $\lvert T_+^H S_0^C\rangle$ | 0 | 0 | 0 | 0 | 0 | 0 | 0 | 0 |
| $\lvert T_-^H S_0^C\rangle$ | 0 | 0 | 0 | 0 | 0 | 0 | 0 | 0 |

$$\begin{array}{c|cccccccc}
 & |T_0^H T_-^C\rangle & |T_-^H T_0^C\rangle & |S_0^H T_0^C\rangle & |T_0^H S_0^C\rangle & |S_0^H T_+^C\rangle & |T_+^H S_0^C\rangle & |S_0^H T_-^C\rangle & |T_-^H S_0^C\rangle \\
\hline
|S_0^H S_0^C\rangle & 0 & 0 & 0 & 0 & 0 & 0 & 0 & 0 \\
|T_0^H T_0^C\rangle & 0 & 0 & 0 & 0 & 0 & 0 & 0 & 0 \\
|T_+^H T_+^C\rangle & 0 & 0 & 0 & 0 & 0 & 0 & 0 & 0 \\
|T_-^H T_-^C\rangle & 0 & 0 & 0 & 0 & 0 & 0 & 0 & 0 \\
|T_+^H T_-^C\rangle & 0 & 0 & 0 & 0 & 0 & 0 & 0 & 0 \\
|T_-^H T_+^C\rangle & 0 & 0 & 0 & 0 & 0 & 0 & 0 & 0 \\
|T_0^H T_+^C\rangle & 0 & \frac{\Sigma J_{near}+\Sigma J_{far}}{4} & 0 & 0 & \frac{-\Delta J_{far}-\Delta J_{near}}{4} & \frac{\Sigma J_{near}-\Sigma J_{far}}{4} & 0 & 0 \\
|T_+^H T_0^C\rangle & -\nu_C & -\nu_H & 0 & 0 & \frac{\Delta J_{far}+\Delta J_{near}}{4} & \frac{\Sigma J_{far}-\Sigma J_{near}}{4} & 0 & 0 \\
|T_0^H T_-^C\rangle & \frac{\Sigma J_{near}+\Sigma J_{far}}{4} & 0 & 0 & 0 & 0 & 0 & \frac{-\Delta J_{far}+\Delta J_{near}}{4} & \frac{\Sigma J_{far}+\Sigma J_{near}}{4} \\
|T_-^H T_0^C\rangle & 0 & 0 & 0 & 0 & 0 & 0 & \frac{\Sigma J_{far}-\Sigma J_{near}}{4} & \frac{\Delta J_{near}-\Delta J_{far}}{4} \\
|S_0^H S_0^C\rangle & 0 & \frac{\Delta J_{far}+\Delta J_{near}}{4} & \frac{\Sigma J_{far}-\Sigma J_{near}}{4} & 0 & 0 & 0 & 0 & 0 \\
|T_0^H S_0^C\rangle & 0 & \frac{-\Delta J_{far}-\Delta J_{near}}{4} & \frac{\Sigma J_{near}-\Sigma J_{far}}{4} & -J_{CC} & 0 & 0 & 0 & 0 \\
|S_0^H T_+^C\rangle & 0 & 0 & -J_{HH} & 0 & 0 & 0 & 0 & 0 \\
|T_+^H S_0^C\rangle & 0 & 0 & \frac{\Delta J_{near}-\Delta J_{far}}{4} & 0 & -J_{CC}+\nu_H & 0 & 0 & 0 \\
|S_0^H T_-^C\rangle & \frac{\Delta J_{far}+\Delta J_{near}}{4} & \frac{-\Delta J_{far}-\Delta J_{near}}{4} & 0 & 0 & 0 & 0 & -\nu_C-J_{HH} & \frac{\Delta J_{near}-\Delta J_{far}}{4} \\
|T_-^H S_0^C\rangle & \frac{\Sigma J_{far}-\Sigma J_{near}}{4} & \frac{\Sigma J_{far}-\Sigma J_{near}}{4} & 0 & 0 & 0 & 0 & \frac{\Delta J_{near}-\Delta J_{far}}{4} & -\nu_H-J_{CC} \\
\end{array}$$

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method of hyperpolarizing heteronuclei, the method comprising:
    (a) combining a plurality of molecules of parahydrogen, a plurality of molecules of a catalyst, and a plurality of molecules of a compound, where the compound includes a heteronucleus and another atom that exists naturally as either a quadrupolar or a non-quadrupolar isotope, where the heteronucleus in at least 50% of the plurality of molecules of the compound is a hyperpolarizable heteronucleus, and where the plurality of molecules of the compound have been modified so as to isotopically enrich the other atom with the non-quadrupolar isotope, and where the parahydrogen, the compound and the catalyst associate to form a complex; and
    (b) applying a magnetic field with a strength of less than 50 µT to the complex, thereby transferring the spin order from the parahydrogen to the hyperpolarizable heteronucleus associated with the complex.

2. The method of claim 1, where the other atom is a nitrogen atom, and the plurality of molecules of the compound have been modified so as to isotopically enrich the nitrogen atom with $^{15}$N.

3. The method of claim 1, where the other atom is a hydrogen atom, and the plurality of molecules of the compound have been modified so as to isotopically enrich the hydrogen atom with $^{1}$H.

4. The method of claim 1, where the hyperpolarizable heteronuclei is $^{13}$C.

5. The method of claim 1, where the hyperpolarizable heteronucleus is $^{19}$F.

6. The method of claim 1, where the hyperpolarizable heteronucleus is $^{15}$N, $^{29}$Si, $^{31}$P, $^{129}$Xe, $^{7}$Li, $^{89}$Y, $^{107}$Ag or $^{109}$Ag.

7. The method of claim 1, where the spin order is transferred during a temporary association of parahydrogen, the compound, and the catalyst while maintaining the chemical identity of the compound.

8. The method of claim 1, where the magnetic field is determined by matching the resonance frequency of parahydrogen with the resonance frequency of at least one hyperpolarizable nucleus of the compound.

9. The method of claim 1, where the magnetic field has a strength of less than 20 µT.

10. The method of claim 1, where the magnetic field has a strength of about 0.1 to about 1 µT.

11. The method of claim 1, where the catalyst is a heterogeneous catalyst.

12. The method of claim 1, where the catalyst is a homogeneous catalyst.

13. The method of claim 1, where the catalyst comprises a transition metal.

14. The method of claim 13, where the transition metal in the complex coordinates with the other atom.

15. The method of claim 13, wherein the transition metal is iridium.

16. The method of claim 1, where the catalyst is activated prior to forming the complex, and the pre-activation catalyst is [IrCl(COD)(IMes)].

17. The method of claim 1, where the catalyst is a homogeneous or heterogeneous catalyst, wherein the catalyst accommodates the simultaneous exchange of para-H$_2$ and heteronuclear spin center(s), and wherein the condition of spin-spin (weak or strong J) coupling between para-H$_2$ derived protons and heteronuclear spin center(s) is maintained.

18. The method of claim 1, where the compound is a contrast agent for an in vivo imaging technique.

19. The method of claim 1, where the heteronucleus is a first heteronucleus and the compound further includes a second heteronucleus, where the second heteronucleus in at least 50% of the plurality of molecules of the compound is a hyperpolarizable heteronucleus, wherein when the first and second heteronuclei are both hyperpolarizable, the first and second heteronuclei are a J-coupled pair;
    wherein upon applying the magnetic field with a strength of less than 50 µT to the complex, the spin order from the parahydrogen is transferred to the J-coupled pair, thereby inducing a hyperpolarized long-lived spin state.

* * * * *